US007928284B2

(12) United States Patent
Ambati

(10) Patent No.: US 7,928,284 B2
(45) Date of Patent: Apr. 19, 2011

(54) METHODS AND ANIMAL MODEL FOR ANALYZING AGE-RELATED MACULAR DEGENERATION

(75) Inventor: Jayakrishna Ambati, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 98 days.

(21) Appl. No.: 12/382,702

(22) Filed: Mar. 23, 2009

(65) Prior Publication Data

US 2009/0260091 A1 Oct. 15, 2009

Related U.S. Application Data

(63) Continuation of application No. 10/685,705, filed on Oct. 16, 2003, now Pat. No. 7,595,430.

(60) Provisional application No. 60/422,096, filed on Oct. 30, 2002.

(51) Int. Cl.
*A01K 67/00* (2006.01)
*A01K 67/027* (2006.01)
*A01K 67/033* (2006.01)
*A61K 49/00* (2006.01)
*G01N 33/00* (2006.01)

(52) U.S. Cl. .................. 800/3; 800/13; 800/14; 800/18; 424/9.1

(58) Field of Classification Search ........................ None
See application file for complete search history.

(56) References Cited

OTHER PUBLICATIONS

Ambati, J. et al. "An animal model of age-related macular degeneration in senescent macrophage recruitment impaired mice." Association for Research in Vision Opthalmology Annual Meeting Abstract Search and Program Planner, 2003.
Grossniklaus, H. et al. "Macrophage and retinal pigment epithelium expression of angiogenic cytokines in choroidal neovascularization." Molecular Vision, 2002, vol. 8, pp. 119-126.
Kuziel, W. et al. "Severe reduction in leukocyte adhesion and monocyte extravasation in mice deficient in CC chemokine receptor 2." Proceedings of the National Academy of Sciences USA, Oct. 1997, vol. 94, pp. 12053-12058.
Lu, B. et al. "Abnormalities in Monocyte Recruitment and Cytokine Expression in Monocyte Chemoattractant Protein 1-deficient Mice." Journal of Experimental Medicine, Feb. 1998, vol. 187, pp. 601-608.
Raisler, B. et al. "Adeno-associated virus type-2 expression of pigmented epithelium-derived factor or Kringles 1-3 of angiostatin reduce retinal neovascularization." PNAS, Jun. 2002, vol. 99, pp. 8909- 8914.
Acland, Gregory, M., et al. "Gene therapy restores vision in canine model of childhood blindness." Nature Genetics, vol. 28, May 2001, pp. 92-95.
Elner, Victor, M., et al. "Cell-Associated Human Retinal Pigment Epithelium Interleukin-8 and Monocyte Chemotactic Protein-1: Immunochemical and In-situ Hybridization Analyses." Experimental Eye Research, Dec. 1997, vol. 65, No. 6, pp. 781-789.
Doetschman, T. (1999) Interpretation of phenotype in genetically engineered mice. Laboratory Animal Science 49(2): 137-143.
Donehower et al. (1995) Effects of genetic background on tumorigenesis in p53-deficient mice. Molecular Carnicogenesis 14: 16-22.
Jacks et al. (1992) Effects of an Rb mutation in the mouse. Nature 359: 295-300.
Jaenisch et al. (1988) Transgenic Animals. Science 240: 1468-1474.
Kuehn et al. (1987) A potential animal model for Lesch-Nyhan syndrome through introduction of HPRT mutations into mice. Nature 326: 295-298.
Petridou et al. (2003) Heterogeneous inducible mammary-specific expression of JAB/SOCS1 in lactating transgenic mice is associated with no obvious phenotype, even at the cellular level. Transgenic Research 12: 693-706.
Sigmund, CD (2000) Viewpoint: Are studies in genetically altered mice out of control? Arterioscler. Thromb. Vasc. Biol. 20: 1425-4129.
C.B. Moens et al., "Defects in heart and lung development in compound heterozygotes for two different targeted mutations at the N-*myc* locus," Development 119, 485-499 (1993).

*Primary Examiner* — Anne-Marie Falk
(74) *Attorney, Agent, or Firm* — McDermott Will & Emery LLP

(57) ABSTRACT

Methods for testing candidate drugs for treatment of age-related macular degeneration are provided. Ccl2-deficient, and Ccr2-deficient mice are used to determine the effect of candidate drugs and treatments on development of age-related macular degeneration. Also provided is a Ccl2-deficient, Ccr2-deficient dual knockout mouse, which is a useful animal model for age-related macular degeneration.

28 Claims, 37 Drawing Sheets
(6 of 37 Drawing Sheet(s) Filed in Color)

migrated macrophages per mm 2
PBS
BSA
C5a
IgG
CCL2

% adherent macrophages
μg/spot
BSA
C5a
IgG

Relative C5-positive RPE and choroidal area
Mφ
CCL2
CCR2

Relative IgG-positive RPE and choroidal area
Mφ
CCL2
CCR2

FIG. 7A
SEQ ID NO: 1 Human Ccl2 gene
Sequence 1:

```
ggaaccgaga ggctgagact aacccagaaa catccaattc tcaaactgaa gctcgcactc      60
tcgcctccag catgaaagtc tctgccgccc ttctgtgcct gctgctcata gcagccacct     120
tcattcccca agggctcgct cagccagatg caatcaatgc cccagtcacc tgctgttata     180
acttcaccaa taggaagatc tcagtgcaga ggctcgcgag ctatagaaga atcaccagca     240
gcaagtgtcc caaagaagct gtgatcttca agaccattgt ggccaaggag atctgtgctg     300
accccaagca gaagtgggtt caggattcca tggaccacct ggacaagcaa acccaaactc     360
cgaagacttg aacactcact ccacaaccca agaatctgca gctaacttat ttcccctag      420
ctttccccag acaccctgtt ttattttatt ataatgaatt ttgtttgttg atgtgaaaca     480
ttatgcctta agtaatgtta attcttattt aagttattga tgttttaagt ttatctttca     540
tggtactagt gtttttttaga tacagagact tggggaaatt gcttttcctc ttgaaccaca    600
gttctacccc tgggatgttt tgagggtctt tgcaagaatc attaatacaa agaatttttt     660
ttaacattcc aatgcattgc taaaatatta ttgtggaaat gaatattttg taactattac     720
accaaataaa tatatttttg tacaaaaaaa aaaaaaa                              757
```

FIG. 7B
SEQ ID NO: 2 Human Ccl2 gene variant
Sequence 2:

```
agactaaccc agaaacatcc aattctcaaa ctgaagctcg cactctcgcc tccagcatga      60
aagtctctgc cgcccttctg tgcctgctgc tcatagcagc caccttcatt ccccaagggc     120
tcgctcagcc agatgcaatc aatgccccag tcacctgctg ttataacttc accaatagga     180
agatctcagt gcagaggctc gcgagctata gaagaatcac cagcagcaag tgtcccaaag     240
aagctgtgat cttcaagacc attgtggcca aggagatctg tgctgacccc aagcagaagt     300
gggttcagga ttccatggac cacctggaca agcaaaccca aactccgaag acttgaacac     360
tcactccaca acccaagaat ctgcagctaa cttattttcc cctagctttc cccagacacc     420
ctgttttatt ttattataat gaattttgtt tgttgatgtg aaacattatg ccttaagtaa     480
tgttaattct tatttaagtt attgatgttt taagtttatc tttcatggta ctagtgtttt     540
ttagatacag agacttgggg aaattgcttt tcctcttgaa ccacagttct acccctggga     600
tgttttgagg gtctttgcaa gaatcattaa tacaaagaat ttttttaac attccaatgc      660
attgctaaaa tattattgtg gaaatgaata ttttgtaact attacaccaa ataaatatat     720
ttttgtacaa aaaaaaaaaa aaa                                             743
```

FIG. 7C
SEQ ID NO: 3 Human Ccl2 promoter region
Sequence 3:

```
ccgagatgtt cccagcacag ccccatgtga gagctccctg gctccgggcc cagtatctgg 60
aatgcaggct ccagccaaat gcattctctt ctacgggatc tgggaacttc caaagctgcc 120
tcctcagagt gggaatttcc actcacttct ctcacgccag cactgacctc ccagcggggg 180
agggcatctt ttcttgacag agcagaagtg ggaggcagac agctgtcact ttccagaaga 240
ctttcttttc tgattcatac ccttcacctt ccctgtgttt actgtctgat atatgcaaag 300
gccaagtcac tttccagaga tgacaactcc ttcctgaagt agagacatgc ttccaacact 360
cagaagccta tgtgaacact cagccagcaa agctgggaag tttttctctg tgaccatggg 420
ctaattggtc tccttctctg gattgtggct ttatcagata aaaacaagtg gtcatgccac 480
aggatgtcta taagcccatt gattctggga ttctatgagt gatgctgata tgactaagcc 540
aggagagact tatttaaaga tctcagcatc tttcagcttg ttaacctaga gaaaacccga 600
agcatgactg gattataaag ggaaattgaa tgcggtccac caagttcatg gtaaaggatg 660
cactaacaga ttagagagag gtttcccctg atatgaggaa aacttcttgg aagatgaggt 720
gagatggcct aggaagaaat tcctacacaa aattgcacag tctctagtcc tggaaacatt 780
ttattcattg gataagaatg gattgaggca tgagcagagg actgagacaa acacagagaa 840
gtttcaacac tggttgggga gaaaaggagt aactagtgag attcaggcag aacaagaata 900
aggctcctca agaggcacaa gcaaagcagg gctcgagttg atttgttctc tcttcatcct 960
gctttttgta attccaccag agtctgaaat gaccactcca tagagtctct gctctgggat 1020
tctccaggaa accaatatcc atcatgagac atcaagtcta gtcccaggaa gaagagattc 1080
tggaatggaa acatcctggg tgggagtctc agcacatcta ctattctgtc tgagttactg 1140
gacaaataac ttcagtttta acctaacgaa agctgggttg gttggaggac tgggcaggca 1200
gcgctggaaa gtatgtcagc accatacctg actccctgaa tgcactcaac aatgccatta 1260
ctgaccactt actagaaata aaacagtcat ttgttgaata caacccgttt ctttttacaa 1320
gtgtagtgaa aagtgttttc tttcaagaaa ccccatgcat ttatagacat tgcctcagtg 1380
accctttatg aaagaagtca ctagtctttg tatgcccatt gggcaagggc accgcaaggc 1440
tcagaaggag gaggcagtgg gctaggagaa tggagagatc agaattttaa actcagccca 1500
gccattaaca tgcctcaagt actcctatca tatttgtaag agacaacagt tcactgaaat 1560
gaattctaag gtctttgggt ttttatcagt gtgcttctgt agtttctgag gaaatctaag 1620
gcacaactga ggaatgaagt caggctttcc aattcccgaa atactcctcc actgcttact 1680
catgtccctt ggaaattaag aaggaagcca ggagaatagc tgccataacc agggatgaac 1740
ttcttgtcca ctgctgcctg ctatgctagc aacagcctcc taactcataa tgacttagcc 1800
```

FIG. 7C (continued)
SEQ ID NO: 3 Human Ccl2 promoter region
Sequence 3:

```
atgaggaatg tttctagatt ctcctttagc tgtctgccca tttggaagat gctgaggaca   1860
gagagaggac ccaagcaggc aactagttgg aggacttgta cacgtttcct tccagcagta   1920
tgtcagagag gtgagcagcc cactggggac agggctgcct gggttctgtg ctcgagggga   1980
ccttgagcag gctatttaac ccttctgtgc ctcagttgcc tgatctataa catgaaaatt   2040
agcaatcccct actagataaa gttggggaat ttacagagtt aatatttgta aaggtctgag   2100
aatattcctg gcagagtaag cactctgtga gtatgacact ggcatttctt ctgcagcact   2160
acatgctgtc tatgcctttg tccaagtctg aaaccctaga actcttagaa ttcagttcaa   2220
tgtttacaca atcctacagt tctgctaggc ttctatgatg ctactattct gcatttgaat   2280
gagcaaatgg atttaatgca ttgtcaggga gccggccaaa gcttgagagc tccttcctgg   2340
ctgggaggcc ccttggaatg tggcctgaag gtaagctggc agcgagcctg acatgctttc   2400
atctagtttc ctcgcttcct tccttttctg cagttttcgc ttcacagaaa gcagaatcct   2460
taaaaataac cctcttagtt cacatctgtg gtcagtctgg gcttaatggc accccatcct   2520
ccccatttgc tcatttggtc tcagcagtga atggaaaaag tgtctcgtcc tgaccccctg   2580
cttccctttc ctacttcctg gaaatccaca ggatgctgca tttgctcagc agatttaaca   2640
gcccacttat cactcatgga agatccctcc tcctgcttga ctccgccctc tctccctctg   2700
cccgctttca ataagaggca gagacagcag ccagaggaac cgagaggctg agactaaccc   2760
agaaacatcc aattctcaaa ctgaagctcg cactctcgcc tccagcatga aagtctctgc   2820
cgccccttctg tgcctgctgc tcatagcagc caccttcatt ccccaagggc tcgctcagcc   2880
aggtaaggcc ccctcttctt ctccttgaac cacattgtct tctctctgag ttatcatgga   2940
ccatccaagc agacgtggta cccacagtct tgctttaacg ctacttttcc aagataaggt   3000
gactcagaaa aggacaaggg gtgagcccaa ccacacagct gctgctcggc agagcctgaa   3060
ctagaattcc agctgtgaac cccaaatcca gctccttcca ggattccagc tctgggaaca   3120
cactcagcgc agttactccc ccagctgctt ccagcagagt ttggggatca gggtaatcaa   3180
agagagggtg ggtgtgtagg ctgtttccag acacgctgga g                        3221
```

FIG. 7D
SEQ ID NO: 4 Human Ccl2 gene and enhancer region
Sequence 4:

```
ggtacctcct ccagccttgg ccacagtgtc atccttgggc cccctaggtt tcagcctctt     60
gagtttgcac ttgcaggttt ggctgttgct ctcaaagcag gactattgca tcaacatggc    120
aggtgcagag gtcttcccgc ctcaatcgtc acccactgat ttctctgcca tggccttgaa    180
ctcaggcgac caatccagtt ggaacctccc cacactctcc gtggctaata attttggact    240
cagaagaaaa agcctcaatt tctctcctct caggaggtct cttggtcctt gagcaaatgt    300
atccatttct tctcctatct ccagtctttg ggcccccaaa ggtttttttc tccctttctc    360
caggacaatg agtgcctatt tacaagtgcc tgtttctact tgaataaggt ttctataaac    420
taagaagtgt tccttaggga cacaagtaac tggcactcct gttggaaaat gctaagatct    480
aggtcacgcg cacttccccc aacagacaca tacacacatt cacacacaca cacacacaca    540
cacacacaca cacacacaca cacacataca gcttgtctgc actctagcac tggcactgac    600
gctaacgcta taatcctggg caactttatt tccccatctt acattaagca gtggtgcagg    660
gattttcaac tctgggatct ctatcacacc tcccagctct gattgcttcc taatttacat    720
atttattgag catctgatgc taggtcctca tgctggtgat gcaggagtaa actagacaga    780
caaaagtccg tgccccacat tgtctgacac ctacacacct gctgttcgga ctccattaca    840
aacagctcca aggggaacag tgcacttgta aagtttctct cattaccatg gccacatccg    900
tgagcaataa ataagttgca tagttgaatt atttgataat gctttgtttt taactccctg    960
cacttaagtc agagatgtgt gtgctttgga aaactatttc tcctgactca ttagacaaat   1020
actatttgca tttttattca gcttccttcc tcagactcta atttacagta aaggcaagag   1080
gatttttgaa tggagccagt gctttgcaat gtggggctcc accagctagc cgactgaaat   1140
cattaataaa gaagcctttt taagtggctg aagtttcccc tttttggcat gcaacatttt   1200
gcaaccaagc ggaagaaaca tcatccgcaa agaagaatcc atgtggcccc tgaaaatcac   1260
tctctctgct acaggctccc cactccccag tgctcccctt agccctgcca ctatctctcc   1320
tccagatgga aaaagtgagg aactcaggga accaaaagtc ttgcttcttt actaatttcc   1380
```

FIG. 7D (continued)
SEQ ID NO: 4 Human Ccl2 gene and enhancer region
Sequence 4:

ctgtctgaca ttaaatcatc ctacagttca gatatctggg ggaagtgact agagattctt 1440
gaactgttaa taattaattt aaatgatatt tgttaagaac ctacgacatg gaagatactg 1500
taccaggtgc tggggtccag catgggcaaa ggcctcaagg tggaatggag ctatggtgtg 1560
ttctggaagc agagagtggg gctgagggtg acatgaggtg aggagacagg agagggcctg 1620
gcagggtggg accttctggt gagagctggc tgctgtgtga ggagctgagg ccctggcttg 1680
attctggggt tacttctttg accttcagct ttttgtcatg ggcagacaga atggggatga 1740
aaaaaagctt aggaaatgga aacctcccta tgcattatat aataaaaatg gccaacacat 1800
tttcatagca agaaatcaca gcagaagctt gtactgggca tcaggactgt aggcatccaa 1860
tgcccagaaa ctggcatgtg ccctgggaca tcccctgaga aggcatgcca cgagccctca 1920
gactgacaca gctctttaca agttgcttac agagcactct tggtttatta attcatacaa 1980
gtctcatgac aatgtcagaa gcagctgtct tactaatccc ctttgacaga agaggcccag 2040
agaggtcaag ggacttgctc aaggccacac agctagaaag aggcagagcc aggcctttgg 2100
ccctggtgtt ctgacaccac ctggggctcc ttctgttatt ccatgctacc tcttctttct 2160
cttccgtatt cccttctcgt tcccttcctt cttgtgtctt gcttcttatc tgcctgtact 2220
tattcctgtt ggtgcctccc agctcagcca gcatagctct gtcttcaaat accccatgct 2280
tcattctggg gtcccataca cagtctgaca atcatctgag gggctgtgg gaggacatag 2340 aaaaaataca gctttacata gaaaaaaatg caaattgtag ccaggcgcag tggctcatgc 2400
ctgtaacccc agcactttgg gaggccgagg caggtggatc acctgaggtc aggagtctga 2460
gaccagcctg gccaatgtag taaaactcct tctctactaa aaatataaaa attagccagg 2520
cgtgatgtca tgtgcctgta gtcccagcta ctcgggaggc tgaggcagga gaacctcttg 2580
aatccaggag gcgcaggttg cagtgagcag agatagtgcc actgcactcc agcctgggtg 2640
acagagtgag actctgtctc aaaaaaataa aataaaataa aaaatgcaga ctgtgattca 2700
gcaggtctgg gttgaagccc agaactctct gataaattca atggcactta actacttgga 2760
ggtcatggat gcctttgcta atctaataga agctactgac cctctctcca gaaaaatgca 2820

FIG. 7D (continued)
SEQ ID NO: 4 Human Ccl2 gene and enhancer region
Sequence 4:

caaaaacata aatgtggaag acaactcctg atggatctgg gagcctatcc aagggccaca 2880
gacaagagtc ctggtctgga caaaatgagc tgctcagtat tttcccacct ggccagcatt 2940
tcctatccaa agacaaatgt taaagttgtt ctagcagagc catgcaccag cagcagtatc 3000
atcacctggg aaccggttag caatgcagaa ccgcaggccc accccaaacc tacagtcaga 3060
atctctactt tagcaagatc ctaaggagat gggtaagcac attacaattt gcaacctttg 3120
taagtttgcc caaaatgtga cccctccttc acccaccgat cgccaaggtt caaaaatctg 3180
cccaaccctt gagcccatct taaatgtacc atcacgagcc ttccctgggc ccctcagctg 3240
ggactctcac cgctctgtat ctttctggtt aatgcaatta ttctgttccc ttagatgacc 3300
ccagcacagg tgctaaagga gtcaacaaaa ggctattgtc aaaaaagtgt ttctgtctcc 3360
actccatctg atctctgttt ccctaagacc tgcccatccc cctctcccag ttcggcacct 3420
tgaccccctc atcacactgc tcaggccacc ttgtacaatg caagccccaa atgaggaaag 3480
cattttctcc cccaatgtgt aacacgaaag tgctgtagag tggctcacgc tgcctttagc 3540
ctaagaattt atttaactct tacccccaac ccacatcagt ctcctccctc tagggctcag 3600
gtgctaatct gtgagggctg gctcagaaga caatctaaag aacaagcctc ttgcttcctc 3660
aggcatcact actcctcacc accatcaccc ccacccacca actcaggcca ctactctttc 3720
tgttctcata tgctatgccc atcgccaccc ctattcccat gctcaggagt attcttggct 3780
actgcatgca attagacctg gggcagatcc aatccagaaa gcaagaaatc ttagatgctg 3840
gaagcttggg gtaagtactg atcagattta ttcctaaatt cagtcctact ttccatggat 3900
tcttacttta gcatctcttc tgaaaaggaa gcatcatgtc taattcactt ctccctccct 3960
gtgcagtcct ctacctggtg ctctgcacag ggtatgtgct aattgtatga atgttataat 4020
aaagagatag tgcagtagat gacaaagggc actacattga gagcccagaa ataagcaaac 4080
cagcacaaat gtagccattc gtcttctatc tcaccttgag cctgtcacta acctgttcat 4140
ggcctcagtc tccccatcag agaaacaggt agatggtctc taaggtctcg ttcattttct 4200
gacattctgt gaaaaattaa ggaaagattt tcatccttga caggaaaggg attgcagagt 4260

FIG. 7D (continued)
SEQ ID NO: 4 Human Ccl2 gene and enhancer region
Sequence 4:

agcggccctg ggaaaatggg ctctattcta cctggagcta gcctggagga gaggccttga 4320
gtgggggttg tctagaaagg acatggtgag tgcagagcta cggtgcatct ctcttgaagg 4380
ctgagtgaag ggagcaccag caagggagcc tgcactaggt ggggagggac aagtgaaccg 4440
cagaagttgg tgggagccca ggcagtggct tcagatcttt ccagagagct cacttttact 4500
tcctcttttt ttcacccctg acactgagtg ggagtctgca gcgatgacca aggttcatgc 4560
agaggatctt agtggtgggg tcagaccccg ggaggaatga agaaagcatt attcaccaag 4620
aggagctttt ccattcttta tctatgagtt gatagagagg aggccccggg gtaactgagg 4680
attctggaca gcatcagagc attgaccctc attttcccca tagcccctct gggggccttt 4740
cccttgtgtg tccccaagcg agagtccaac caaggtttgt gccagagcct aacccaggct 4800
tgtgccgaga tgttcccagc acagccccat gtgagagctc cctggctccg ggcccagtat 4860
ctggaatgca ggctccagcc aaatgcattc tcttctacgg gatctgggaa cttccaaagc 4920
tgcctcctca gagtgggaat ttccactcac ttctctcacg ccagcactga cctcccagcg 4980
ggggagggca tcttttcttg acagagcaga agtgggaggc agacagctgt cactttccag 5040
aagactttct tttctgattc atacccttca ccttccctgt gtttactgtc tgatatatgc 5100
aaaggccaag tcactttcca gagatgacaa ctccttcctg aagtagagac atgcttccaa 5160
cactcagaag cctatgtgaa cactcagcca gcaaagctgg gaagtttttc tctgtgacca 5220
tgggctaatt ggtctccttc tctggattgt ggctttatca gataaaaaca agtggtcatg 5280
ccacaggatg tctataagcc cattgattct gggattctat gagtgatgct gatatgacta 5340
agccaggaga gacttattta aagatctcag catctttcag cttgttaacc tagagaaaac 5400
ccgaagcatg actggattat aaagggaaat tgaatgcggt ccaccaagtt catggtaaag 5460
gatgcactaa cagattagag agaggtttcc cctgatatga ggaaaacttc ttggaagatg 5520
aggtgagatg gcctaggaag aaattcctac acaaagttgc acagtctcta gtcctggaaa 5580
cattttattc attggataag aatggattga ggcatgagca gaggactgag acaaacacag 5640
agaagtttca acactggttg gggagaaaag gagtaactag tgagattcag gcagaacaag 5700

FIG. 7D (continued)
SEQ ID NO: 4 Human Ccl2 gene and enhancer region
Sequence 4:

aataaggctc ctcaagaggc acaagcaaag cagggctcga gttgatttgt tctctcttca 5760
tcctgctttt tgtaattcca ccagagtctg aaatggccac tccatagagt ctctgctctg 5820
ggattctcca ggaaaccaat atccatcatg agacatcaag tctagtccca ggaagaagag 5880
attctggaat ggaaacatcc tgggtgggag tctcagcaca tctactattc tgtctgagtt 5940
actggacaaa taacttcagt tttaacctaa cgaaagctgg gttggttgga ggactgggca 6000
ggcagcgctg gaaagtatgt cagcaccata cctgactccc tgaatgcact caacaatgcc 6060
attactgacc acttactaga aataaaacag tcatttgttg aatacaaccc gtttcttttt 6120
acaagtgtag tgaaaagtgt tttctttcaa gaaaccccat gcatttatag acattgcctc 6180
agtgaccctt tatgaaagaa gtcactagtc tttgtatgcc cattgggcaa gggcaccgca 6240
aggctcagaa ggaggaggca gtgggctagg agaatcgaga gatcagaatt ttaaactcag 6300
cccagccatt aacatgcctc aagtactcct atcatatttg taagagacaa cagttcactg 6360
aaatgaattc taaggtcttt gggtttttat cagtgtgctt ctgtagtttc tgaggaaatc 6420
taaggcacaa ctgaggaatg aagtcaggct ttccaattcc cgaaatactc ctccactgct 6480
tactcatgtc ccatggaaat taagaaggaa gccaggagaa tagctgccat aaccagggat 6540
gaacttcttg tccactgctg cctgctatgc tagcaacagc ctcctaactc ataatgactt 6600
agccatgagg aatgtttcta gattctcctt tagctgtctg cccatttgga agatgctgag 6660
gacagagaga ggacccaagc aggcaactag ttggaggact tgtacacgtt tccttccagc 6720
agtatgtcag agaggtggca gcccactggg gacagggctg cctgggttct gtgctcgagg 6780
ggaccttgag caggctattt aacccttctg tgcctcagtt gcctgatcta taacatgaaa 6840
attagcaatc cctactagat aaagttgggg aatttacaga gttaatattt gtaaaggtct 6900
gagaatattc ctggcagagt aagcactctg tgagtatgac actggcattt cttctgcagc 6960
actacatgct gtctatgcct ttgtccaagt ctgaaaccct agaactctta gaattcagtt 7020
caatgtttac acaatcctac agttctgcta ggcttctatg atgctactat tctgcatttg 7080
aatgagcaaa tggatttaat gcattgtcag ggagccggcc aaagcttgag agctccttcc 7140

FIG. 7D (continued)
SEQ ID NO: 4 Human Ccl2 gene and enhancer region
Sequence 4:

tggctgggag gccccttgga atgtggcctg aaggtaagct ggcagcgagc ctgacatgct 7200
ttcatctagt ttcctcgctt ccttcctttt ctgcagtttt cgcttcacag aaagcagaat 7260
ccttaaaaat aaccctctta gttcacatct gtggtcagtc tgggcttaat ggcaccccat 7320
cctccccatt tgctcatttg gtctcagcag tgaatggaaa aagtgtctcg tcctgacccc 7380
ctgcttccct ttcctacttc ctggaaatcc acaggatgct gcatttgctc agcagattta 7440
acagcccact tatcactcat ggaagatccc tcctcctgct tgactccgcc ctctctccct 7500
ctgcccgctt tcaataagag gcagagacag cagccagagg aaccgagagg ctgagactaa 7560
cccagaaaca tccaattctc aaactgaagc tcgcactctc gcctccagca tgaaagtctc 7620
tgccgccctt ctgtgcctgc tgctcatagc agccaccttc attccccaag ggctcgctca 7680
gccaggtaag gcccccctctt cttctccttg aaccacattg tcttctctct gagttatcat 7740
ggaccatcca agcagacgtg gtacccacag tcttgcttta acgctacttt tccaagataa 7800
ggtgactcag aaaaggacaa ggggtgagcc caaccacaca gctgctgctc ggcagagcct 7860
gaactagaat tccagctgtg aaccccaaat ccagctcctt ccaggattcc agctctggga 7920
acacactcag cgcagttact cccccagctg cttccagcag agtttgggga tcagggtaat 7980
caaagagagg gtgggtgtgt aggctgtttc cagacacgct ggagacccag aatctggtct 8040
gtgcttcatt caccttagct tccagagacg gtgactctgc agaggtaatg agtatcaggg 8100
aaactcatga ccaggcatag cctattcaga gtctaaaagg aggctcatag tggggctccc 8160
cagctgatct tccctggtgc tgatcatctg gattattggt ccgtcttaat gacacttgta 8220
ggcattatct agctttaact ctgtccatta tcaatgttat atacccattt tacagcatag 8280
gaaactgagt cattgggtca aagatcacat tctagctctg aggtataggc agaagcactg 8340
ggatttaatg agctctttct cttctcctgc ctgccttttg ctttttcctc atgactcttt 8400
tctgctctta agatcagaat aatccagttc atcctaaaat gctttttctt tgtggtttat 8460
tttccagatg caatcaatgc cccagtcacc tgctgctata acttcaccaa taggaagatc 8520
tcagtgcaga ggctcgcgag ctatagaaga atcaccagca gcaagtgtcc caaagaagct 8580

FIG. 7D (continued)
SEQ ID NO: 4 Human Ccl2 gene and enhancer region
Sequence 4:

gtgatgtgag ttcagcacac caaccttccc tggcctgaag ttcttccttg tggagcaagg 8640
gacaagcctc ataaacctag agtcagagag tgcactattt aacttaatgt acaaaggttc 8700
ccaatgggaa aactgaggca ccaagggaaa aagtgaaccc caacatcact ctccacctgg 8760
gtgcctattc agaacacccc aatttcttta gcttgaagtc aggatggctc cacctggaca 8820
cctataggag cagtttgccc tgggttccct ccttccacct gcgttcctcc tctagctccc 8880
atggcagccc tttggtgcag aatgggctgc acttctagac caaaactgca aaggaacttc 8940
atctaactct gtcctccctc cccacagctt caagaccatt gtggccaagg agatctgtgc 9000
tgaccccaag cagaagtggg ttcaggattc catggaccac ctggacaagc aaacccaaac 9060
tccgaagact tgaacactca ctccacaacc caagaatctg cagctaactt attttcccct 9120
agctttcccc agacaccttg ttttatttta ttataatgaa ttttgtttgt tgatgtgaaa 9180
cattatgcct taagtaatgt taattcttat ttaagttatt gatgttttaa gtttatcttt 9240
catggtacta gtgtttttta gatacagaga cttggggaaa ttgcttttcc tcttgaacca 9300
cagttctacc cctgggatgt tttgagggtc tttgcaagaa tcattaatac aaagaatttt 9360
ttttaacatt ccaatgcatt gctaaaatat tattgtggaa atgaatattt tgtaactatt 9420
acaccaaata aatatatttt tgtacaaaac ctgacttcca gtgttttctt gaaggaaatt 9480
acaaagctga gagtatgagc ttggtggtga caaaggaaca tgatttcaga gggtggggct 9540
tacattttga aggaatggga aagtggattg gccccggtct tctccactgg gtggtctcct 9600
ctgagtctcc gtagaagaat ctttatggca ggccagttag gcattaaagc accacccttc 9660
cagtcttcaa cataagcagc ccagagtcca atgaccctgg tcacccattt agcaagagcc 9720
caacccccat tccttttctc acagaccctg acccctgcat gcaattcttc ccttaacata 9780
ttgcaactgc cccctaactg ggctacccac cccccaatct gtacctctcc aattaatacc 9840
ccaacctgga gtaatacaga cactgccagt attaggaaat aaggaaagag ttaatcacca 9900
tagataagat gattagattg aagtttcata gagatgatga gacctgaact tattatttat 9960
gaatgaagaa ggcttttcta ggaaaattat aggatcatta agaaaggaga aggaagagtg 10020

FIG. 7D (continued)
SEQ ID NO: 4 Human Ccl2 gene and enhancer region
Sequence 4:

ggagcaaata cctggaggta gaaatggtga tgatgtgtac atcaagcagg gagaaaacca 10080
atgaaccaga tgcgaattcg ggcccacacc aatgtcaagg gatgacaatt agaaaggaag 10140
gttgagtcaa gggatttgaa tgttagggtg aaaagttact actcaactct gtaggttaaa 10200
aggaaacgtt gagaatcttc agtccaatga ggagggatgt gccatgttta gagattcaga 10260
gataagtttc aggaaatgta acttatagat tttatacata cacagagaaa tacggactag 10320
tgagaagcta ttgccatggt ccaagcaaga gatgatgaag gcctaaatat ggagccaaag 10380
aggcagcaat gaagaatgag ccatgcaggg tgaaatgctg catgttgtaa atggaggaga 10440
aagacctgtg acttcagata tgaaaacctc atcttcaacc cacattttaa gggggcagct 10500
tccctgaaac cagaatgtgt ttccctccat tactataccc ccatcccaat ctcaggcacc 10560
tggaatcatc catttaaaca gatgagcctt ctattcctaa atagccacct gaagtgtgta 10620
ttcctttgca tgatatttgt cccacctaaa gcattcgacc tgcctgggca cccacaccac 10680
gccaacactc aggaaagcag atgtcttgct ctgttgaata aactgcatgg ttcttaactt 10740
cccagtctgg tggggaaatg accactgtgt caacctagag caggcagtgc ttttggcagc 10800
atgaggtgct ggggacaact ttgactggca agaagcacac tcaggttctc accccgcatc 10860
cagcgctgac tcgctttgtc agtcaagaca ggtcagatat tctgagccta catcgatcat 10920
acaggtatga taatgtgtta caaataggaa cccagaggaa aggttccctt tcggatctgg 10980
gagcacatct gttggaaaac ttccatttct actaactgga gttgcagagg gagagaaggg 11040
attctgcttc tacattcctg agccagtcca gggtccctga atcagactac cgaatccctt 11100
caaagctcca agtaccctga tatatcagtc agcagacaat ttattgacag ctatttagaa 11160
aactcactga ccctcactcc aggtcaagca gcgtcccctg cctctcctct acccctacat 11220
tccctggcct tgatcaccag tcaggagtga aatctcaaat tgcagtagat gccaagaggc 11280
aaaaagagaa tagaatgcaa acaaatgaga cctcatcata tggcttccga gcagcaacct 11340
tttgacgcca ggcagatttg aggcagacag tctgggagga gaggaggcag agaaaggggg 11400
gatccacatg ctcaaacccc aaattaatct gcttacattc cccttgcagg ccacatctct 11460

FIG. 7D (continued)
SEQ ID NO: 4 Human Ccl2 gene and enhancer region
Sequence 4:

tcattttcag gaagtcttga ctccatactg ttttccaccc aagcatggaa ttcctttcat 11520
gatgaaactg aacacagggc attggcagtg gtgagactct gttttagaag aaagtgccaa 11580
gtgcaatgca ttcatttcct gttgctgcca acaatcagtt ccaggaaatc taggcttttt 11640
atgtcatgct caaaattctt ccagcctatg ctcattattc aaatccaaag ccacatccac 11700
atctgtaggt gttagttaca gaagcaccat atttccaggt accaaaatct gtattagttt 11760
cttattgtta ctgtaacaaa ttcccataag ctt 11793

FIG. 8A
SEQ ID NO: 5 Human Ccr2 gene variant A
Sequence 5:

```
caggactgcc tgagacaagc cacaagctga acagagaaag tggattgaac aaggacgcat     60
ttccccagta catccacaac atgctgtcca catctcgttc tcggtttatc agaaatacca    120
acgagagcgg tgaagaagtc accacctttt ttgattatga ttacggtgct ccctgtcata    180
aatttgacgt gaagcaaatt ggggcccaac tcctgcctcc gctctactcg ctggtgttca    240
tctttggttt tgtgggcaac atgctggtcg tcctcatctt aataaactgc aaaaagctga    300
agtgcttgac tgacatttac ctgctcaacc tggccatctc tgatctgctt tttcttatta    360
ctctcccatt gtgggctcac tctgctgcaa atgagtgggt ctttgggaat gcaatgtgca    420
aattattcac agggctgtat cacatcggtt attttggcgg aatcttcttc atcatcctcc    480
tgacaatcga tagatacctg gctattgtcc atgctgtgtt tgctttaaaa gccaggacgg    540
tcacctttgg ggtggtgaca agtgtgatca cctggttggt ggctgtgttt gcttctgtcc    600
caggaatcat ctttactaaa tgccagaaag aagattctgt ttatgtctgt ggcccttatt    660
ttccacgagg atggaataat ttccacacaa taatgaggaa cattttgggg ctggtcctgc    720
cgctgctcat catggtcatc tgctactcgg gaatcctgaa aaccctgctt cggtgtcgaa    780
acgagaagaa gaggcatagg gcagtgagag tcatcttcac catcatgatt gtttactttc    840
tcttctggac tccctataac attgtcattc tcctgaacac cttccaggaa ttcttcggcc    900
tgagtaactg tgaaagcacc agtcaactgg accaagccac gcaggtgaca gagactcttg    960
ggatgactca ctgctgcatc aatcccatca tctatgcctt cgttggggag aagttcagaa   1020
gcctttttca catagctctt ggctgtagga ttgccccact ccaaaaacca gtgtgtggag   1080
gtccaggagt gagaccagga aagaatgtga aagtgactac acaaggactc ctcgatggtc   1140
gtggaaaagg aaagtcaatt ggcagagccc ctgaagccag tcttcaggac aaagaaggag   1200
cctagagaca gaaatgacag atctctgctt tggaaatcac acgtctggct tcacagatgt   1260
gtgattcaca gtgtgaatct tggtgtctac gttaccaggc aggaaggctg agaggagaga   1320
gactccagct gggttggaaa acagtatttt ccaaactacc ttccagttcc tcatttttga   1380
atacaggcat agagttcaga cttttttaa atagtaaaaa taaaattaaa gctgaaaact   1440
```

FIG. 8A (continued)
SEQ ID NO: 5 Human Ccr2 gene variant A
Sequence 5:

```
gcaacttgta aatgtggtaa agagttagtt tgagttgcta tcatgtcaaa cgtgaaaatg   1500
ctgtattagt cacagagata attctagctt tgagcttaag aattttgagc aggtggtatg   1560
tttgggagac tgctgagtca acccaatagt tgttgattgg caggagttgg aagtgtgtga   1620
tctgtgggca cattagccta tgtgcatgca gcatctaagt aatgatgtcg tttgaatcac   1680
agtatacgct ccatcgctgt catctcagct ggatctccat tctctcaggc ttgctgccaa   1740
aagccttttg tgttttgttt tgtatcatta tgaagtcatg cgtttaatca cattcgagtg   1800
tttcagtgct tcgcagatgt ccttgatgct catattgttc cctaatttgc cagtgggaac   1860
tcctaaatca aattggcttc taatcaaagc ttttaaaccc tattggtaaa gaatggaagg   1920
tggagaagct ccctgaagta agcaaagact ttcctcttag tcgagccaag ttaagaatgt   1980
tcttatgttg cccagtgtgt ttctgatctg atgcaagcaa gaaacactgg gcttctagaa   2040
ccaggcaact tgggaactag actcccaagc tggactatgg ctctactttc aggccacatg   2100
gctaaagaag gtttcagaaa gaagtgggga cagagcagaa ctttcacctt catatatttg   2160
tatgatccta atgaatgcat aaaatgttaa gttgatggtg atgaaatgta aatactgttt   2220
ttaacaacta tgatttggaa aataaatcaa tgctataact atgttgataa aag          2273
```

FIG 8B
SEQ ID NO: 6 Human Ccr2 gene variant B
Sequence 6:

```
caggactgcc tgagacaagc cacaagctga acagagaaag tggattgaac aaggacgcat     60
ttccccagta catccacaac atgctgtcca catctcgttc tcggtttatc agaaatacca    120
acgagagcgg tgaagaagtc accacctttt ttgattatga ttacggtgct ccctgtcata    180
aatttgacgt gaagcaaatt ggggcccaac tcctgcctcc gctctactcg ctggtgttca    240
tctttggttt tgtgggcaac atgctggtcg tcctcatctt aataaactgc aaaaagctga    300
agtgcttgac tgacatttac ctgctcaacc tggccatctc tgatctgctt tttcttatta    360
ctctcccatt gtgggctcac tctgctgcaa atgagtgggt ctttgggaat gcaatgtgca    420
aattattcac agggctgtat cacatcggtt attttggcgg aatcttcttc atcatcctcc    480
tgacaatcga tagatacctg gctattgtcc atgctgtgtt tgctttaaaa gccaggacgg    540
tcacctttgg ggtggtgaca agtgtgatca cctggttggt ggctgtgttt gcttctgtcc    600
caggaatcat ctttactaaa tgccagaaag aagattctgt ttatgtctgt ggcccttatt    660
ttccacgagg atggaataat ttccacacaa taatgaggaa cattttgggg ctggtcctgc    720
cgctgctcat catggtcatc tgctactcgg gaatcctgaa aaccctgctt cggtgtcgaa    780
acgagaagaa gaggcatagg gcagtgagag tcatcttcac catcatgatt gtttactttc    840
tcttctggac tccctataac attgtcattc tcctgaacac cttccaggaa ttcttcggcc    900
tgagtaactg tgaaagcacc agtcaactgg accaagccac gcaggtgaca gagactcttg    960
ggatgactca ctgctgcatc aatcccatca tctatgcctt cgttggggag aagttcagaa   1020
ggtatctctc ggtgttcttc cgaaagcaca tcaccaagcg cttctgcaaa caatgtccag   1080
ttttctacag ggagacagtg gatggagtga cttcaacaaa cacgccttcc actggggagc   1140
aggaagtctc ggctggttta taaaacgagg agcagtttga ttgttgttta taaagggaga   1200
taacaatctg tatataacaa caaacttcaa gggtttgttg aacaatagaa acctgtaaag   1260
caggtgccca ggaacctcag ggctgtgtgt actaatacag actatgtcac ccaatgcata   1320
tccaacatgt gctcagggaa taatccagaa aaactgtggg tagagacttt gactctccag   1380
aaagctcatc tcagctcctg aaaaatgcct cattaccttg tgctaatcct ctttttctag   1440
```

FIG 8B (continued)
SEQ ID NO: 6 Human Ccr2 gene variant B
Sequence 6:

```
tcttcataat ttcttcactc aatctctgat tctgtcaatg tcttgaaatc aagggccagc   1500
tggaggtgaa gaagagaatg tgacaggcac agatgaatgg gagtgaggga tagtggggtc   1560
agggctgaga ggagaaggag ggagacatga gcatggctga gcctggacaa agacaaaggt   1620
gagcaaaggg ctcacgcatt cagccaggag atgatactgg tccttagccc catctgccac   1680
gtgtatttaa ccttgaaggg ttcaccaggt cagggagagt ttgggaactg caataacctg   1740
ggagttttgg tggagtccga tgattctctt ttgcataagt gcatgacata tttttgcttt   1800
attacagttt atctatggca cccatgcacc ttacatttga aatctatgaa atatcatgct   1860
ccattgttca gatgcttctt aggccacatc cccctgtcta aaaattcaga aaatttttgt   1920
ttataaaaga tgcattatct atgatatgct aatatatgta tatgcaatat aaaatttag    1979
```

FIG. 8C
SEQ ID NO: 7 Human Ccr2 gene isoform A
Sequence 7:

```
gtttatgaaa ttacagggct ggagacaaag atcacaatgt gaagacaaaa ttggagagcg     60
gtcctaatca gccagagcaa aatttctggc tcttgctctt ccccatcctg ggttgaatca    120
taggaacagg tggcaagatg ccagggtcag gagattccag aagtggcagc aagctcagtg    180
ttaccaggtc agggatgacc tgtcttatta ttgaaatctc agagatatgc tccaattccg    240
gcccagagac acattgagag acaactgggg aacttgctat gttcctgaac aggcaatgag    300
ctgtcttcca agaaaaaacc tgagaccctt caagtctcag gtcttactta gcacatatac    360
caggtcttac acaggacaca tggttacaac tgactgaaat ctgggctggg tgtaggagct    420
cacacctgta atcccagccc ttcaggaggc tgaggcaggc agattgcctg agcccaggag    480
ttcgagacca gcccgggcaa catgacaaaa ccccatctct acaaaaaata gtcaggcatg    540
gtggcatgca cctgtagtct cagctacttg ggaggctgag atgagaggat tgcttgaggt    600
tgagactgca gtgaagcatg atcatgccac cgcactccag cctaggcaac agagcaagat    660
cttgtcgcaa aagaaagcaa aaacacaaca taacacaaca acaacaacaa caacaacaac    720
agcaaaaaag ccaacttctt gaaatctgga aaggacacct ggactgccct gagcatttga    780
ttgttgttgg ctctagcagt ggatgcatcc ttcaacctct ggcactctgc agggctcaga    840
ctgttctgtt ctgtttgtta cctgtggagt gcctgccaga ccctgctcta gctgctttag    900
gtccatttac cctcatagac ccccagtctt gttattcata tttcatattt gggaaatgga    960
aacttagaaa cttgccaagt ccacagcatg agatcctgcc tccggtgtct gctggattcc   1020
agaaagtgcc aggggccaac ttagatgaca ccatgttctc tgcacaatct taggaatgct   1080
cctagtctga tgtccccatt gcaaaattta cattatcttt taacaaaacg tctttccaag   1140
gaggggcatt taaaataact gaggttcttc ttgctaagga agttcctgac acaagagata   1200
atttagcatt tccttttcat taaaaagttt gaaatcctgt aatttgtgat aatgtggatg   1260
aacctagagg atgttaagtg aaataagcca cacacagata gacaaatacc acgtgatctc   1320
actcttatgt ggaatttttt tttaaataag ttgcttagcc gggcatgatg gcacacacct   1380
```

FIG. 8C (continued)
SEQ ID NO: 7 Human Ccr2 gene isoform A
Sequence 7:

```
gtaatcctag ctactcagga ggctgaggtg ggaggatggc ttgaactcag aaggtggagg   1440
ttgcagtgag ctgagactgt gccagtgcac tccggtctgg gtgacagaat gaaacccaat   1500
ttaaaaaaaa aaaaaaagtt gctatcttag aaaaagacag tagagcagtg gttaccagag   1560
actggggagg aaagagagga ggtgagaatg ggcagcagtt gatcaacggg tacaaagtta   1620
ccatgagata ggagaaacaa gtgctggtgc tctgctccaa gtagggtgac ggtagttaat   1680
aatgaattct gtatatataa atagctagaa gagagggttt tcaatatcat tattatttca   1740
aaagaaatga taaatgtttc agaggatgga tatgtaatta ccctgatttg atcattgcac   1800
aatgtataca tgtagcaaaa catcacattg tgtcccataa atatatacaa ttattatgtg   1860
aattaaataa aaaaaaattt taaagtctta tctaaatgaa atttctaacc agattctgaa   1920
tccatgatac cactgaaacc agcacacatg atcgcagtaa aacctcatta tacttcctcc   1980
actatcacca ataccctta ttctctggaa catgaaacat tctgttgtgc tcatatcatg   2040
caaattatca ctagtaggag agcagagagt ggaaatgttc caggtataaa gacccacaag   2100
ataaagaagc tcagagtcgt tagaaacagg agcagatgta cagggtttgc ctgactcaca   2160
ctcaaggttg cataagcaag atttcaaaat taatcctatt ctggagacct caacccaatg   2220
tacaatgttc ctgactggaa aagaagaact atatttttct gatttttttt tttcaaatct   2280
ttaccattag ttgccctgta tctccgcctt cactttctgc aggaaacttt atttcctact   2340
tctgcatacc aagtttctac ctctagatct gtttggttca gttgctgaga agcctgacat   2400
accaggactg cctgagacaa gccacaagct ggtgagttgt aggcattttt tccattactt   2460
tctgattcat aggctcaacg cacctcaaag ctggaaatgc cgggtctggg tacaccctgg   2520
ggaactgcaa agcctgcaca cttgggggga atgatcaaga tgagaggcag gggtggggat   2580
ggcatgtgca ccaggagatg ttagagaaac cctgaggaag agcagcgtgc agcaggtgat   2640
gggggagagt gggcagcaag cgaggccagg acagccactc tgctcagtca ccagtccaca   2700
cacccagggg ctcactctgc ccctctgagc acccaaggac gttaaagagc tggaactgtt   2760
agtctaaata taggaccatc caagctctga accaaaatgt gtcccttgcc tcaactcagg   2820
```

FIG. 8C (continued)
SEQ ID NO: 7 Human Ccr2 gene isoform A
Sequence 7:

agatccacag aggcagaagt aaggaattta ttttctgaaa gatagatttc tatcagttct 2880
gggtgacatg ttctgacact tgaaatgaca cctaggacag cacatttcag gcatcttgct 2940
cattgttcac tgtagtagaa gctacatgct agccagttgt aaaaatgaaa ttaagtaatg 3000
tgtgcacagc atttaacata gcatctgagc ttcaggagca ctcaattaat gaccacagtt 3060
gtgattcttt aggcagatgc attttttcc aactttgatc agaggtctta tttagcttct 3120
ccagatttca agaatctggc tcagtgatat gaaatacaag acttgtgaaa agtgtcaatt 3180
gcaagagaaa tggaaggata aagtatacag gtgggtggaa aagaaattca cagtcactgc 3240
cagaaaaaaa attcttgaga atcaagtcct gatgatgtta gggcttatag ttcttattat 3300
aaagagtttt atgtactcat tcagtgaaca tttattggtg cctcctttag ccaggtacta 3360
tcataagagc tgaaaataga agcataatcc agtccttgat cttgaggaac atgctgtgtg 3420
tagcagataa cataataagt gcttatctag atgcatgcag tgttatgtga taagagtaat 3480
atgacagagg atacagatta ggcttcacag agaaggggga tttgagcagg aggtattgaa 3540
gggtgaatag aagctcacca atcattttgg gcagaggggc aaggacctgc aaaaccactg 3600
aagcatgaag gaaatggtga gtttagggaa aatgaagaga agatggctgt gactgaagca 3660
caggatttgg gattggagaa gggactggag gtgaggctga aaagaggcaa actcagaaaa 3720
gatgttgtgc tgggcagtct ggacattatc tttgaagccc accacatata agtcataggg 3780
ctactggagg ttttaagcta agagtgacta ttcaatttca acttaagaga agataggttg 3840
agagggaaca tggcttgaga tgagccatga gcaaaggaaa gactacaaca aagccaggag 3900
tgaggagtgt gtgaagcaag aaagtgacag ttgaaagcag tgcagagggg atgaatctga 3960
gaggcatcta tgaggtggaa ctcaaatgac atgataataa tacagggcat ttctctgtgt 4020
cagatgctgt cctaagtcct tactccattg atcttcacag caactcagca tagttaatat 4080
tttatgcata aagaaatcgg cacttgaagg agtaattggc cccagattac actgcctata 4140
aggattcaaa tccaggtttg tttggctcca aaaactggct cctaattttc agaaggagaa 4200

FIG. 8C (continued)
SEQ ID NO: 7 Human Ccr2 gene isoform A
Sequence 7:

```
gcgacccagg gcaatgccca attttgcttc ttaggcaatg gaggaatcca caatcggaag   4260
gagttttcag cagtgcccca tttggggtgg gttgaatttg aggtccctgc atgataccca   4320
ctttgctcac ttcagtgcct aaaactgagt atggttcata gtaggtgttc aataagtgtt   4380
gatgcagtga atacatgcat ggggagatat gcatcaggca atgggaaatt caactctaag   4440
gcttagggga aagctggagc ttgaagacag agctttagaa aacagtagca tagaagggag   4500
taggaaccat gagtttagac aatacaattc aggaagaact ttgtagcaag gataaagagg   4560
caaaaaatta aagaggtgag agctaagtgt ggtgcctggg gaatcttaag gtgtgggcac   4620
ggggaggaga tgccagcaaa gaacatgaat aaaaagcggt agcacagccc ctcccatctg   4680
gaagccaaaa agaattgtaa atggaggaag ttagcagaag gatcaaatac ttgaagaggg   4740
tggaattgga ataaaaccag ggcatttgaa aaattgggtt gtcactgcaa tcttaacaag   4800
agaagttttg gcaggatgat ggaggcagaa agctgagaga atcatcagtt agaacgtttt   4860
tgacttcaga gaacagaaaa tgcagttcat aatggcttta aaacaggggc ttgtttttct   4920
cccagcaatt tgagaggcca aggcgggtgc atcaggaggt caagagaccg agaccatcct   4980
ggccaacatg gtgaatcccc atctctacta aaaatacaaa aattagcggg gcatggtggt   5040
gcacgcctat agtcccatct actcaggagg ctgaggcagg agaatcactt gaacccagga   5100
ggtggaggtt gcagtgagct gagatcatgg ccactgcact atagcctgga gacacagcga   5160
gactccgtct ccaaaaaaaa aaaaaaagaa ggcagaaggt gaatagttca agggtgggtt   5220
taggactcag tgataatagg attctgcctg gcttctcatg gttctctagg tcttccattc   5280
atggcaccat gccctcacta ggcatgctgc cagagcagga ggggcaggtg gagggttctc   5340
ttgtgtctgt cttatcaggg aagaagagct ttctcagaag cccccagcag actccctttt   5400
catattatgg tccagcaatg agtcacagac ctatgcacca cctgcaaagg agccagagaa   5460
aacaaacgcc cagcgctttt agcctgaaaa tgagaatctg gtttgctggg gaagataaag   5520
ggtgtcggaa aatggctgtt gggtaaatca ttgatgtctg ccactaggaa tgaaaggcaa   5580
atcaggaact ggcacacatg ctttcaggga gatggctgca agggagaggg caaagactgg   5640
```

FIG. 8C (continued)
SEQ ID NO: 7 Human Ccr2 gene isoform A
Sequence 7:

gaagttgctt atgtggtgcc agactatttg gaagatcatg gattgcggtg tttgtgttgt 5700
gtggtcatca ttttgttctt tgtttacaga acagagaaag tggattgaac aaggacgcat 5760
ttccccagta catccacaac atgctgtcca catctcgttc tcggtttatc agaaatacca 5820
acgagagcgg tgaagaagtc accacctttt ttgattatga ttacggtgct ccctgtcata 5880
aatttgacgt gaagcaaatt ggggcccaac tcctgcctcc gctctactcg ctggtgttca 5940
tctttggttt tgtgggcaac atgctggtcg tcctcatctt aataaactgc aaaaagctga 6000
agtgcttgac tgacatttac ctgctcaacc tggccatctc tgatctgctt tttcttatta 6060
ctctcccatt gtgggctcac tctgctgcaa atgagtgggt ctttgggaat gcaatgtgca 6120
aattattcac agggctgtat cacatcggtt attttggcgg aatcttcttc atcatcctcc 6180
tgacaatcga tagatacctg gctattgtcc atgctgtgtt tgctttaaaa gccaggacgg 6240
tcacctttgg ggtggtgaca agtgtgatca cctggttggt ggctgtgttt gcttctgtcc 6300
caggaatcat ctttactaaa tgccagaaag aagattctgt ttatgtctgt ggcccttatt 6360
ttccacgagg atggaataat ttccacacaa taatgaggaa cattttgggg ctggtcctgc 6420
cgctgctcat catggtcatc tgctactcgg gaatcctgaa aaccctgctt cggtgtcgaa 6480
acgagaagaa gaggcatagg gcagtgagag tcatcttcac catcatgatt gtttactttc 6540
tcttctggac tccctataat attgtcattc tcctgaacac cttccaggaa ttcttcggcc 6600
tgagtaactg tgaaagcacc agtcaactgg accaagccac gcaggtgaca gagactcttg 6660
ggatgactca ctgctgcatc aatcccatca tctatgcctt cgttggggag aagttcagaa 6720
ggtatctctc ggtgttcttc cgaaagcaca tcaccaagcg cttctgcaaa caatgtccag 6780
ttttctacag ggagacagtg gatggagtga cttcaacaaa cacgccttcc actggggagc 6840
aggaagtctc ggctggttta taaaacgagg agcagtttga ttgttgttta taaagggaga 6900
taacaatctg tatataacaa caaacttcaa gggtttgttg aacaatagaa acctgtaaag 6960
caggtgccca ggaacctcag ggctgtgtgt actaatacag actatgtcac ccaatgcata 7020

FIG. 8C (continued)
SEQ ID NO: 7 Human Ccr2 gene isoform A
Sequence 7:

tccaacatgt gctcagggaa taatccagaa aaactgtggg tagagacttt gactctccag 7080
aaagctcatc tcagctcctg aaaaatgcct cattaccttg tgctaatcct ctttttctag 7140
tcttcataat ttcttcactc aatctctgat tctgtcaatg tcttgaaatc aagggccagc 7200
tggaggtgaa gaagagaatg tgacaggcac agatgaatgg gagtgaggga tagtggggtc 7260
agggctgaga ggagaaggag ggagacatga gcatggctga gcctggacaa agacaaaggt 7320
gagcaaaggg ctcacgcatt cagccaggag atgatactgg tccttagccc catctgccac 7380
gtgtatttaa ccttgaaggg ttcaccaggt cagggagagt ttgggaactg caataacctg 7440
ggagttttgg tggagtccga tgattctctt ttgcataagt gcatgacata tttttgcttt 7500
attacagttt atctatggca cccatgcacc ttacatttga aatctatgaa atatcatgct 7560
ccattgttca gatgcttctt aggccacatc cccctgtcta aaaattcaga aaatttttgt 7620
ttataaaaga tgcattatct atgatatgct aatatatgta tatgcaatat atataggctc 7680
ttgcttgatc tctccaggag gtagtgatta tgagaagggg gtggagaatg atgagttcct 7740
tcaccaggag caaaggacgg ggatcgtgtg gaaccactgc agaactattt ccgaaatcaa 7800
ctaagtggag agagccagga aggctgcatc agaacccagt aaagcttctt gtctggatct 7860
gagctggttt gttttgtgct tgcttttccc tgccttgcca ctcccctcac tcttctcttt 7920
tccccacagc ctttttcaca tagctcttgg ctgtaggatt gccccactcc aaaaaccagt 7980
gtgtggaggt ccaggagtga gaccaggaaa gaatgtgaaa gtgactacac aaggactcct 8040
cgatggtcgt ggaaaaggaa agtcaattgg cagagcccct gaagccagtc ttcaggacaa 8100
agaaggagcc tagagacaga aatgacagat ctctgctttg gaaatcacac gtctggcttc 8160
acagatgtgt gattcacagt gtgaatcttg gtgtctacgt taccaggcag gaaggctgag 8220
aggagagaga ctccagctgg gttggaaaac agtattttcc aaactacctt ccagttcctc 8280
atttttgaat acaggcatag agttcagact ttttttaaat agtaaaaata aaattaaagc 8340
tgaaaactgc aacttgtaaa tgtggtaaag agttagtttg agttactatc atgtcaaacg 8400
tgaaaatgct gtattagtca cagagataat tctagctttg agcttaagaa ttttgagcag 8460

FIG. 8C (continued)
SEQ ID NO: 7 Human Ccr2 gene isoform A
Sequence 7:

```
gtggtatgtt tgggagactg ctgagtcaac ccaatagttg ttgattggca ggagttggaa   8520
gtgtgtgatc tgtgggcaca ttagcctatg tgcatgcagc atctaagtaa tgatgtcgtt   8580
tgaatcacag tatacgctcc atcgctgtca tctcagctgg atctccattc tctcaggctt   8640
gctgccaaaa gccttttgtg ttttgttttg tatcattatg aagtcatgcg tttaatcaca   8700
ttcgagtgtt tcagtgcttc gcagatgtcc ttgatgctca tattgttccc tattttgcca   8760
gtgggaactc ctaaatcaag ttggcttcta atcaaagctt ttaaacccta ttggtaaaga   8820
atggaaggtg gagaagctcc ctgaagtaag caaagacttt cctcttagtc gagccaagtt   8880
aagaatgttc ttatgttgcc cagtgtgttt ctgatctgat gcaagcaaga aacactgggc   8940
ttctagaacc aggcaacttg ggaactagac tcccaagctg gactatggct ctactttcag   9000
gccacatggc taaagaaggt ttcagaaaga agtggggaca gagcagaact ttcaccttca   9060
tatatttgta tgatcctaat gaatgcataa aatgttaagt tgatggtgat gaaatgtaaa   9120
tactgttttt aacaactatg atttggaaaa taaatcaatg ctataactat gttgataaaa   9180
gatttaaaaa caactggctg ttttttttaca ctgtggtgtg gaagattgtg ttgtgttcac   9240
aacttttcac ttcttcccct gtgtgattac acacacctgc ccttgtggtg tgacttgcag   9300
tgcgccctac aggccacaca accccatgcc ctccaccact ggctctgctg ctggaatgtg   9360
agcagaagtg acatctgcct catccaagca gagcctcttg ctcagccaca ggaaggccca   9420
ttccagatca cacccgtcag cccgtgcgcc ctggtgaatg agaagacaca gggagctgca   9480
gccacatata acatgagcaa gaagtctgtg tttgctgtga taagccactg agttttaggg   9540
gttgtttgtt aagaagcaca aaaaccgatt aagacatgtg gtatatagtg acttcatata   9600
tagaatctgg aaaactatcc atttattttc aatcatggaa ttcaatatga caagcatccc   9660
ggagggtcta cctatgccag actgggttgg aaacagaaag acagatgtta atgccagtgt   9720
cctttacacc tccaagtcca gggccagctg tggagtggga ggggtagaga aggtcctgtg   9780
cacagtcaca gtgcgctgtg cagagcagga acagaggcat ctgtgaaaag tgctgagagc   9840
```

FIG. 8C (continued)
SEQ ID NO: 7 Human Ccr2 gene isoform A
Sequence 7:

```
ctggaggaca gagtgactaa tgcaatgaca gtcttgcatc ataggaataa cagccacagc    9900
aggattttat tgctgccaaa gaaactgcca tttaaaaatt gccagccatc cgggaggctg    9960
aggcaggaga atggcatgaa tccaggaggc ggagcttgca gtgagccgag atcgggccac   10020
tgcactccag cctgggcaac agagccagac tccatctcaa aaaaaaaaaa aaa          10073
```

FIG. 8D
SEQ ID NO: 8 Human Ccr2 gene promoter
Sequence 8:

```
gcacacctgt aatcccagcc cttcaggagg ctgaggcagg cagattgcct gagcccagga     60
gttcgagacc agcccgggca acatgacaaa accccatctc tacaaaaaat agtcaggcat    120
ggtggcatgc acctgtagtc tcagctactt gggaggctga gatgagagga ttgcttgagg    180
ttgagactgc actgaagcat gatcatgcca ccgcactcca gcctaggcaa cagagcaaga    240
tcttgtcgca aaagaaagca aaaatacaac ataacacaac aacaacaaca acaacaacaa    300
cagcaaaaaa gccaacttct tgaaatctgg aaaggacacc tccactgccc tcagcatttg    360
attgttgttg gctctagcag tggatgcatc cttcaacctc tggcactctg caggggctca    420
gactgttctg ttctgtttgt tacctgtgga gtgcctgcca gaccctgctc tagctgcttt    480
aggtccattt accctcatag acccccagtc ttgttattca tatttcatat ttgggaaatg    540
gaaacttaga aacttgccaa gtccacagca tgagatcctg cctccggtgt ctgctggatt    600
ccagaaagtg ccaggggcca acttagatga caccatgttc tctgcacaat cttaggaatg    660
ctcctagtct gatgtcccca ttgcaaaatt tacattatct tttaacaaaa cgtctttcca    720
aggaggggca tttaaaataa ctgaggttct tcttgctaag gacgttcctg acacaagaga    780
taatttagca tttccttttc attaaaaagt ttgaaatcct gtaatttgtg ataatgtgga    840
tgaacctaga ggatgttaag tgaaataagc cacacacaga tagacaaata ccacgtgatc    900
tcactcttat gtggaatttt tttttaaata agttgcttag ccgggcatga tggcacacac    960
ctgtaatcct agctactcag gaggctgagg tgggaggatg gcttgaactc agaaggtgga   1020
ggtagcagtg agctgagact gtgccagtgc actccggtct gggtgacaga atgaaaccca   1080
atttaaaaaa aaaaaaaaag ttgctatctt agaaaaagac agtagagcag tggttaccag   1140
agactgggga ggaaagagag gaggtgagaa tgggcagcag ttgatcaacg ggtacaaagt   1200
taccatgaga taggagaaac aagtgctggt gctctgctcc aagtagggtg acggtagtta   1260
ataatgaatt ctgtatatat aaatagctag aagagagggt tttcaatatc attattattt   1320
caaaagaaat gataaatgtt tcagaggatg gatatgtaat taccctgatt tgatcattgc   1380
acaatgtata catgtagcaa aacatcacat tgtgtcccat aaatatatac aattattatg   1440
```

FIG. 8D (continued)
SEQ ID NO: 8 Human Ccr2 gene promoter
Sequence 8:

```
tgaattaaat aaaaaaaaat tttaaagtct tatctaaatg aaatttctaa ccagattctg   1500
aatccatgat accactgaaa ccagcacaca tgatcgcagt aaaacctcat tatacttcct   1560
ccactatcac caataccctt tattctctgg aacatgaaac attctgttgt gctcatatca   1620
tgcaaattat cactagtagg agagcagaga gtggaaatgt tccaggtata aagacccaca   1680
agataaagaa gctcagagtc gttagaaaca ggagcagatg tacagggttt gcctgactca   1740
cactcaaggt tgcataagca agatttcaaa attaatccta ttctggagac ctcaacccaa   1800
tgtacaatgt tcctgactgg aaaagaagaa ctatattttt ctgatttttt ttttcaaatc   1860
tttaccatta gttgccctgt atctccgcct tcactttctg caggaaactt tatttcctac   1920
ttctgcatgc caagtttcta cctctagatc tgtttggttc agttgctgag aagcctgaca   1980
taccaggact gcctgagaca agccacaagc tggtgagttg taggcatttt ttccattact   2040
ttctgattca taggctcaac gcacctcaaa gctggaaatg cc                      2082
```

FIG. 9
SEQ ID NO: 9 Human C5 receptor gene
Sequence 9

```
ctacctccaa ccatgggcct tttgggaata ctttgttttt taatcttcct ggggaaaacc    60
tggggacagg agcaaacata tgtcatttca gcaccaaaaa tattccgtgt tggagcatct   120
gaaaatattg tgattcaagt ttatggatac actgaagcat ttgatgcaac aatctctatt   180
aaaagttatc ctgataaaaa atttagttac tcctcaggcc atgttcattt atcctcagag   240
aataaattcc aaaactctgc aatcttaaca atacaaccaa aacaattgcc tggaggacaa   300
aacccagttt cttatgtgta tttggaagtt gtatcaaagc atttttcaaa atcaaaaaga   360
atgccaataa cctatgacaa tggatttctc ttcattcata cagacaaacc tgtttatact   420
ccagaccagt cagtaaaagt tagagtttat tcgttgaatg acgacttgaa gccagccaaa   480
agagaaactg tcttaacctt catagatcct gaaggatcag aagttgacat ggtagaagaa   540
attgatcata ttggaattat ctcttttcct gacttcaaga ttccgtctaa tcctagatat   600
ggtatgtgga cgatcaaggc taaatataaa gaggactttt caacaactgg aaccgcatat   660
tttgaagtta aagaatatgt cttgccacat ttttctgtct caatcgagcc agaatataat   720
ttcattggtt acaagaactt taagaatttt gaaattacta taaaagcaag atatttttat   780
aataaagtag tcactgaggc tgacgtttat atcacatttg gaataagaga agacttaaaa   840
gatgatcaaa aagaaatgat gcaaacagca atgcaaaaca caatgttgat aaatggaatt   900
gctcaagtca catttgattc tgaaacagca gtcaaagaac tgtcatacta cagtttagaa   960
gatttaaaca acaagtacct ttatattgct gtaacagtca tagagtctac aggtggattt  1020
tctgaagagg cagaaatacc tggcatcaaa tatgtcctct ctccctacaa actgaatttg  1080
gttgctactc ctcttttcct gaagcctggg attccatatc ccatcaaggt gcaggttaaa  1140
gattcgcttg accagttggt aggaggagtc ccagtaatac tgaatgcaca aacaattgat  1200
gtaaaccaag agacatctga cttggatcca agcaaaagtg taacacgtgt tgatgatgga  1260
gtagcttcct ttgtgcttaa tctcccatct ggagtgacgg tgctggagtt taatgtcaaa  1320
actgatgctc cagatcttcc agaagaaaat caggccaggg aaggttaccg agcaatagca  1380
```

FIG. 9 (continued)
SEQ ID NO: 9 Human C5 receptor gene
Sequence 9

```
tactcatctc tcagccaaag ttacctttat attgattgga ctgataacca taaggctttg   1440
ctagtgggag aacatctgaa tattattgtt acccccaaaa gcccatatat tgacaaaata   1500
actcactata attacttgat tttatccaag ggcaaaatta tccattttgg cacgagggag   1560
aaattttcag atgcatctta tcaaagtata aacattccag taacacagaa catggttcct   1620
tcatcccgac ttctggtcta ttatatcgtc acaggagaac agacagcaga attagtgtct   1680
gattcagtct ggttaaatat tgaagaaaaa tgtggcaacc agctccaggt tcatctgtct   1740
cctgatgcag atgcatattc tccaggccaa actgtgtctc ttaatatggc aactggaatg   1800
gattcctggg tggcattagc agcagtggac agtgctgtgt atggagtcca aagaggagcc   1860
aaaaagccct tggaaagagt atttcaattc ttagagaaga gtgatctggg ctgtggggca   1920
ggtggtggcc tcaacaatgc caatgtgttc cacctagctg gacttacctt cctcactaat   1980
gcaaatgcag atgactccca agaaaatgat gaaccttgta aagaaattct caggccaaga   2040
agaacgctgc aaaagaagat agaagaaata gctgctaaat ataaacattc agtagtgaag   2100
aaatgttgtt acgatggagc ctgcgttaat aatgatgaaa cctgtgagca gcgagctgca   2160
cggattagtt tagggccaag atgcatcaaa gctttcactg aatgttgtgt cgtcgcaagc   2220
cagctccgtg ctaatatctc tcataaagac atgcaattgg gaaggctaca catgaagacc   2280
ctgttaccag taagcaagcc agaaattcgg agttattttc cagaaagctg gttgtgggaa   2340
gttcatcttg ttcccagaag aaaacagttg cagtttgccc tacctgattc tctaaccacc   2400
tgggaaattc aaggcattgg catttcaaac actggtatat gtgttgctga tactgtcaag   2460
gcaaaggtgt tcaaagatgt cttcctggaa atgaatatac catattctgt tgtacgagga   2520
gaacagatcc aattgaaagg aactgtttac aactatagga cttctgggat gcagttctgt   2580
gttaaaatgt ctgctgtgga gggaatctgc acttcggaaa gcccagtcat tgatcatcag   2640
ggcacaaagt cctccaaatg tgtgcgccag aaagtagagg gctcctccag tcacttggtg   2700
acattcactg tgcttcctct ggaaattggc cttcacaaca tcaatttttc actggagact   2760
```

FIG. 9 (continued)
SEQ ID NO: 9 Human C5 receptor gene
Sequence 9

```
tggtttggaa aagaaatctt agtaaaaaca ttacgagtgg tgccagaagg tgtcaaaagg   2820
gaaagctatt ctggtgttac tttggatcct aggggtattt atggtaccat tagcagacga   2880
aaggagttcc catacaggat acccttagat ttggtcccca aaacagaaat caaaaggatt   2940
ttgagtgtaa aaggactgct tgtaggtgag atcttgtctg cagttctaag tcaggaaggc   3000
atcaatatcc taacccacct ccccaaaggg agtgcagagg cggagctgat gagcgttgtc   3060
ccagtattct atgtttttca ctacctggaa acaggaaatc attggaacat tttcattct    3120
gacccattaa ttgaaaagca gaaactgaag aaaaaattaa aagaagggat gttgagcatt   3180
atgtcctaca gaaatgctga ctactcttac agtgtgtgga agggtggaag tgctagcact   3240
tggttaacag cttttgcttt aagagtactt ggacaagtaa ataaatacgt agagcagaac   3300
caaaattcaa tttgtaattc tttattgtgg ctagttgaga attatcaatt agataatgga   3360
tctttcaagg aaaattcaca gtatcaacca ataaaattac agggtacctt gcctgttgaa   3420
gcccgagaga acagcttata tcttacagcc tttactgtga ttggaattag aaaggctttc   3480
gatatatgcc ccctggtgaa aatcgacaca gctctaatta aagctgacaa ctttctgctt   3540
gaaaatacac tgccagccca gagcaccttt acattggcca tttctgcgta tgctctttcc   3600
ctgggagata aaactcaccc acagtttcgt tcaattgttt cagctttgaa gagagaagct   3660
ttggttaaag gtaatccacc catttatcgt ttttggaaag acaatcttca gcataaagac   3720
agctctgtac ctaacactgg tacggcacgt atggtagaaa caactgccta tgctttactc   3780
accagtctga acttgaaaga tataaattat gttaacccag tcatcaaatg gctatcagaa   3840
gagcagaggt atggaggtgg cttttattca acccaggaca ccatcaatgc cattgagggc   3900
ctgacggaat attcactcct ggttaaacaa ctccgcttga gtatggacat cgatgtttct   3960
tacaagcata aaggtgcctt acataattat aaaatgacag acaagaattt ccttgggagg   4020
ccagtagagg tgcttctcaa tgatgacctc attgtcagta caggatttgg cagtggcttg   4080
gctacagtac atgtaacaac tgtagttcac aaaaccagta cctctgagga agtttgcagc   4140
ttttatttga aaatcgatac tcaggatatt gaagcatccc actacagagg ctacggaaac   4200
```

FIG. 9 (continued)
SEQ ID NO: 9 Human C5 receptor gene
Sequence 9

```
tctgattaca aacgcatagt agcatgtgcc agctacaagc ccagcaggga agaatcatca   4260
tctggatcct ctcatgcggt gatggacatc tccttgccta ctggaatcag tgcaaatgaa   4320
gaagacttaa aagcccttgt ggaaggggtg gatcaactat tcactgatta ccaaatcaaa   4380
gatggacatg ttattctgca actgaattcg attccctcca gtgatttcct ttgtgtacga   4440
ttccggatat ttgaactctt tgaagttggg tttctcagtc ctgccacttt cacagtttac   4500
gaataccaca gaccagataa acagtgtacc atgttttata gcacttccaa tatcaaaatt   4560
cagaaagtct gtgaaggagc cgcgtgcaag tgtgtagaag ctgattgtgg gcaaatgcag   4620
gaagaattgg atctgacaat ctctgcagag acaagaaaac aaacagcatg taaaccagag   4680
attgcatatg cttataaagt tagcatcaca tccatcactg tagaaaatgt tttgtcaag    4740
tacaaggcaa cccttctgga tatctacaaa actggggaag ctgttgctga gaaagactct   4800
gagattacct tcattaaaaa ggtaacctgt actaacgctg agctggtaaa aggaagacag   4860
tacttaatta tgggtaaaga agccctccag ataaaataca atttcagttt caggtacatc   4920
taccctttag attccttgac ctggattgaa tactggccta gagacacaac atgttcatcg   4980
tgtcaagcat ttttagctaa tttagatgaa tttgccgaag atatcttttt aaatggatgc   5040
taaaattcct gaagttcagc tgcatacagt ttgcacttat ggactcctgt tgttgaagtt   5100
cgttttttg ttttcttctt tttttaaaca ttcatagctg gtcttatttg taaagctcac   5160
tttacttaga attagtggca cttgctttta ttagagaatg atttcaaatg ctgtaacttt   5220
ctgaaataac atggccttgg agggcatgaa gacagatact cctccaaggt tattggacac   5280
cggaaacaat aaattggaac acctcctcaa acctaccact caggaatgtt tgctggggcc   5340
gaaagaacag tccattgaaa gggagtatta caaaaacatg gcctttgctt gaaagaaaat   5400
accaaggaac aggaaactga tcattaaagc ctgagtttgc tttc                    5444
```

FIG. 10
SEQ ID NO: 10 Human C5a receptor gene fragment
Sequence 10:

```
ctacctccaa ccatgggcct tttgggaata ctttgttttt taatcttcct ggggaaaacc     60

tggggacagg agcaaacata tgtcatttca gcaccaaaaa tattccgtgt tggagcatct    120

gaaaatattg tgattcaagt ttatggatac actgaagcat ttgatgcaac aatctctatt    180

aaaagttatc ctgataaaaa atttagttac tcctcaggcc at                       222
```

METHODS AND ANIMAL MODEL FOR ANALYZING AGE-RELATED MACULAR DEGENERATION

This application is a Continuation of U.S. application Ser. No. 10/685,705, filed Oct. 16, 2003 now U.S. Pat. No. 7,595,430, claiming priority of U.S. Provisional Application No. 60/422,096, filed Oct. 30, 2002, the entire contents of each of which are hereby incorporated by reference.

FIELD OF THE INVENTION

The invention relates to methods of determining the pathology of age-related macular degeneration and methods of testing treatment protocols and candidate drugs for age-related macular degeneration. More particularly, the invention relates to use of Ccl2-deficient, Ccr2-deficient, or both Ccl2 and Ccr2-deficient mice to analyze the pathology and treatment of age-related macular degeneration and test candidate drugs for treatment of age-related macular edema.

BACKGROUND OF THE INVENTION

Age-related macular degeneration (AMD) is the principal cause of legal blindness in the United States and Western Europe. It affects over 11 million people in this country alone, and with the aging population will exact an even greater toll. The earliest visible abnormality in AMD is the accumulation of drusen (Gass, J. D. (1972) *Trans Am Ophthalmol Soc* 70, 409-36.), lipoproteinaceous deposits between the retinal pigment epithelium (RPE) and Bruch's membrane, the extracellular matrix between the RPE and the underlying choroid. Drusen are a significant risk factor for progression to choroidal neovascularization (CNV), the principal cause of vision loss in AMD (Macular Photocoagulation Study Group (1997) *Arch Ophthalmol* 115, 741-7). There is no animal model of drusen resembling that of patients with AMD. Drusen-like deposits in elderly primates (Hope, et al., (1992) *Br J Ophthalmol* 76, 11-6.) are dissimilar to human drusen both in ultrastructural morphology and biochemical composition (Hirata, A. & Feeney-Burns, L. (1992) *Invest Ophthalmol Vis Sci* 33, 2079-90; Mullins, R. F. & Hageman, G. S. (1997) in *Degenerative Retinal Diseases*, ed. LaVail, M. (Plenum Press, New York), pp. 1-10.). Attempts to create a murine model of drusen by high fat diet, disrupting the apolipoprotein E gene, inducing protoporphyria (Gottsch et al., (1993) *Arch Ophthalmol* 111, 126-9.), accelerating senescence (Majji, et al., (2000) *Invest Ophthalmol Vis Sci* 41, 3936-42), or combinations of the above (Dithmar et al., (2001) *Arch Ophthalmol* 119, 1643-9) have not succeeded in creating drusen.

The biogenesis of drusen involves RPE dysfunction, impaired digestion of photoreceptor outer segments, and subsequent debris accumulation (Hageman, et al.,. (2001) *Prog Retin Eye Res* 20, 705-32). The presence of complement C5, immunoglobulins, apolipoprotein E, vitronectin, and clusterin in human drusen (Loffler, et al., (1986) *Graefes Arch Clin Exp Ophthalmol* 224, 493-501; Hageman, G. S., et al., (1999) *FASEB J* 13, 477-84; Hageman, G. S. & Mullins, R. F. (1999) *Mol Vis* 5, 28 Johnson, et al., (2000) *Exp Eye Res* 70, 441-9; Mullins et al., (2000) *FASEB J* 14, 835-46; and Anderson, et al., (2001) *Am J Ophthalmol* 131, 767-81) suggests that focal concentration of these materials may produce a powerful chemotactic stimulus for leukocytes, possibly acting via a complement cascade (Killingsworth, et al., (2001) *Exp Eye Res* 73, 887-96). Consistent with this, macrophages appear to preferentially engulf the wide-banded collagen of basal deposits in patients with AMD, suggesting a role in drusen clearance (Loffler, K. U. & Lee, W. R. (1986) *Graefes Arch Clin Exp Ophthalmol* 224, 493-501; Killingsworth, et al., (1990) *Eye* 4, 613-21; Penfold, P. L., et al., (1985) *Graefes Arch Clin Exp Ophthalmol* 223, 69-76; and van der Schaft, et al., (1993) *Br J Ophthalmol* 77, 657-61). Laser photocoagulation induced regression of drusen in humans (Ho, et al., (1999) *Ophthalmology* 106, 1367-73; and Olk, et al., (1999) *Ophthalmology* 106, 2082-90) is believed to result from recruitment of macrophages that resort) these deposits (Duvall, J. & Tso, M. O. (1985) *Arch Ophthalmol* 103, 694-703).

The lack of a faithful animal model of AMD has hampered both the study and treatment of age-related macular degeneration. Thus, there is a need for a faithful animal model of drusen development and accumulation to provide mechanistic insights into the development of AMD and assist in evaluating candidate drugs for the treatment of age-related macular degeneration.

SUMMARY OF THE INVENTION

In one aspect of the invention there is provided a method for testing a candidate drug for treatment or prevention of age-related macular degeneration comprising administering the candidate drug to a Ccl2-deficient, Ccr2-deficient- or a Ccl2-deficient and -Ccr2-deficient mouse and analyzing the eye of the mouse for development or regression of drusen and/or lipofuscin accumulation therein, for affect of the candidate drug on Bruch's membrane and/or choroidal neovascularization of the eyes of the mouse.

There is also provided a method of screening a test compound for potential utility for treatment of age-related macular degeneration, comprising: (a) providing a mouse comprising a disrupted Ccl2 and/or CCR2 gene, wherein the mouse is homozygous for the disrupted gene or genes, and wherein the mouse exhibits drusen and/or lipofuscin deposits, retinal degeneration, and/or choroidal neovascularization in at least one eye at about nine to twenty-four months of age compared to a wild-type mouse that does not have the disrupted gene; (b) administering the test compound to the mouse; (c) determining the effect of the test compound on drusen, lipofuscin deposition, retinal degeneration, or choroidal neovascularization in at least one eye of the mouse; and (d) correlating the effect of the test compound on drusen, lipofuscin accumulation, retinal degeneration, and/or choroidal neovascularization with a potential utility to treat age-related macular degeneration.

In another aspect of the invention there is provided a method of monitoring the effects of expression of a Ccl2 gene in at least one eye of a Ccl2−/− mouse comprising (1) introducing a plurality of stem cells obtained from a wild type mouse into the Ccl2−/−mouse to obtain a transplanted mouse, wherein said stem cells express wild type Ccl2; and (2) observing at least one eye of the transplanted mouse for the effect of the wild type Ccr2 gene expression on drusen or lipofuscin deposition, retinal degeneration, or choroidal neovascularization in at least one eye of the transplanted mouse. There is also provided a method of a method of monitoring the expression of a Ccr2 gene in at least one eye of a Ccr2−/− mouse comprising (1) introducing a plurality of stem cells obtained from a wild type mouse into the Ccr2−/− mouse to obtain a transplanted mouse, wherein said stem cells express wild type Ccr2; and (2) observing at least one eye of the transplanted mouse for the effect of the wild type Ccr2 gene expression on drusen or lipofuscin deposition, retinal degeneration, or choroidal neovascularization in at least one eye of the transplanted mouse. There is also provided a method of monitoring the effects of expression of a Ccl2 gene, Ccr2 gene or both in at least one eye of a Ccl2 deficient, Ccr2 deficient mouse comprising (1) introducing a plurality of stem cells obtained from a wild type mouse into the Ccl2 deficient, Ccr2 deficient mouse to obtain a transplanted mouse, wherein said stem cells express wild type Cci2 and Ccr2; and (2) observing at least one eye of the transplanted mouse for the effect of the wild type Ccl2 and/or Ccr2 gene expression on drusen or lipofuscin deposition, retinal degeneration, or choroidal neovascularization in at least one eye of the transplanted mouse.

In a further aspect of the invention there is provided a Ccl2-deficient/CCR2-deficient dual knockout mouse.

The present invention also provides a method of identifying mutations in the Ccl2 gene, Ccr2 gene or both comprising (1) obtaining an AMD DNA library or genomic DNA from a blood sample of an AMD patient; (2) screening the AMD DNA library or genomic DNA for sequences that hybridize under high stringency conditions to a wild type Ccl2 gene, Ccr2 gene, or both; and (3) sequencing the sequences that hybridize to determine the identity of any mutations contained therein.

In a further aspect of the invention there are provided expression vectors comprising SEQ ID NO.9 and/or SEQ ID NO. 10.

In yet a further aspect of the invention there is provided a method of screening for mutations that potentially cause or affect the development of AMD in a human comprising (1) obtaining an AMD DNA library or genomic DNA from a blood sample of an AMD patient; (2) screening the AMD DNA library or genomic DNA for sequences that hybridize under high stringency conditions to a wild type C5 receptor gene or C5a receptor gene; (3) sequencing the sequences that hybridize to determine the identity of any mutations contained therein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figures 1A, 1B, 1C, 1D, 1E, 1F, 1G, 1H:
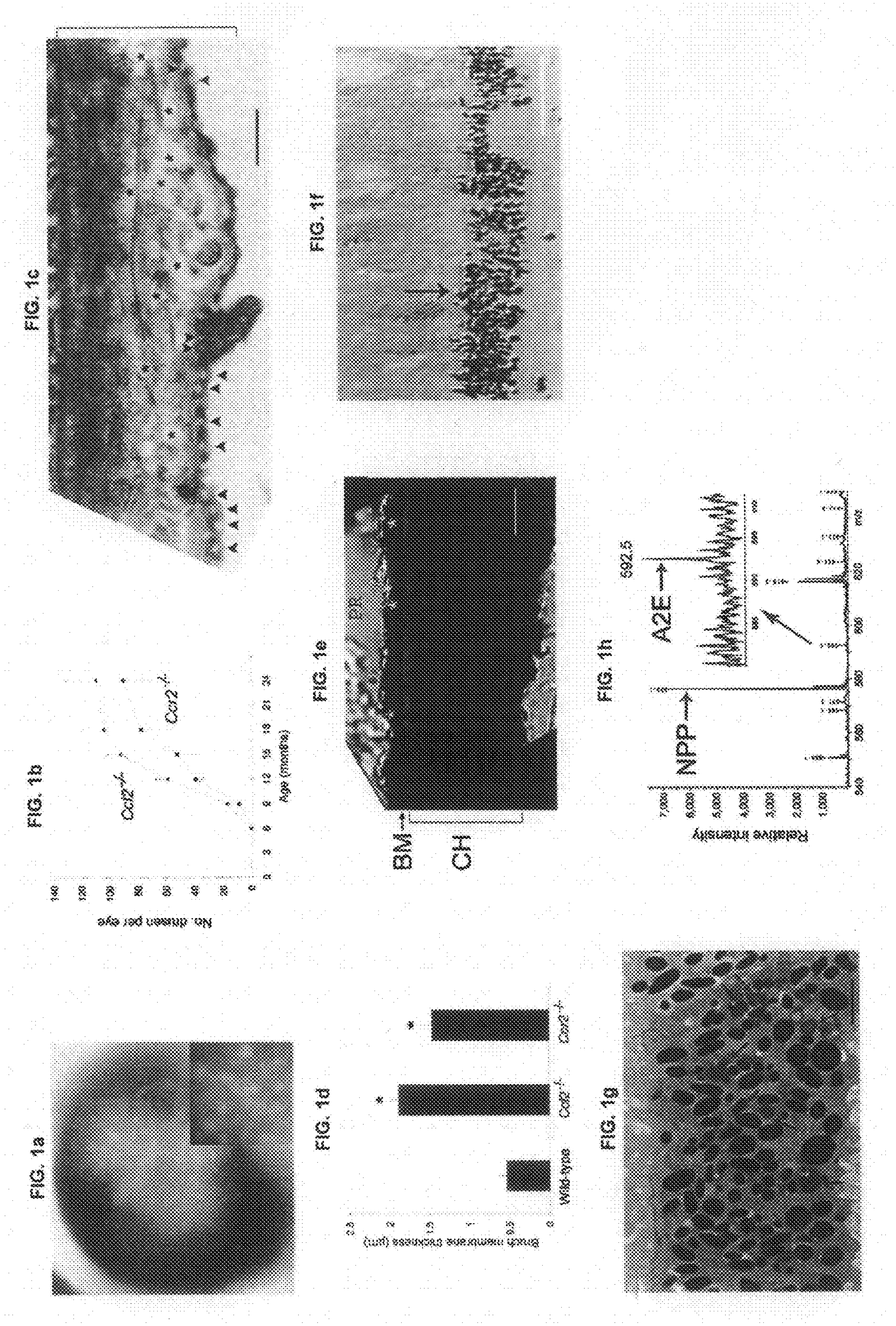
FIG. 1. $Ccl2^{-/-}$ and $Ccr2^{-/-}$ mice develop early AMD. (a) Fundus photo of 15-month-old $Ccl2^{-/-}$ mouse. Inset shows higher magnification. (b) Drusen deposits in knockout mice increase with age (n=4). (c) Collagen and elastin fibers (asterisks) of thickened Bruch membrane (indicated by bracket) in 9-month-old $Ccl2^{-/-}$ mouse are disrupted, and choriocapillaries are highly fenestrated (arrowheads). (d) Bruch membrane is thickened in 10- to 12-month-old knockout mice (n=5). Asterisk P<0.05. (e) TIMP-3 (red) immunoreactivity in RPE and Bruch membrane (BM) of 14-month-old $Ccl2^{-/-}$ mouse. There was no staining in photoreceptors (PR) or choroid (CH). (f) Lipofuscin autofluorescence (red) in light micrograph of RPE (arrow) of 15-month-old $Ccl2^{-/-}$I mouse. (g) Lipofuscin granules (arrows) in electron micrograph of 15-month-old Carl mouse. (h) MALDI spectrum of RPE of 12-month-old $Ccl2^{-/-}$ mouse, showing A2E signal. NPP, N-perfluoroalkyl pyridine. Scale bar=0.5 μm (c), 50, μm (e), 10 μm (f), or 2 μm (g).

FIG. 5. Ccl2 overexpression and macrophage infiltration in aged wild-type mice. Ccl2 fluorescence (blue) is not observed in 4-month-old wild-type (a) but marked immunoreactivity is present in RPE and choroid of 12-month-old wild-type mouse (b). Cluster of F4/80 positive (blue) macrophages in choroid of 12-month-old wild-type (c) but not in 16-month-old $Ccl_2^{-/-}$ mouse (d). Scale bar 150 μm (a,b) and 15 μm (c,d). e, Percentage of choroidal cells expressing F4/80 (macrophages) in young (3-month-old; white bars) and old (12-month-old; black bars) wild-type and knockout mice. n=4. Asterisk $P<0.01$. f, Western blot. RPE and choroid lysates from 6-month-old wild-type (Young WT), 18-month-old wild-type (Old WT), 6-month-old $Ccl2^{-/-}$ (Young CCL2), 16-month-old $Ccl2^{-/-}$ (Old CCL2), 6-month-old $Ccr2^{-/-}$ (Young CCR2), and 18-month-old $Ccr2^{-/-}$ (Old CCR2) mice were analyzed by antibody against mouse C5aR. A 50 kD reactive fragment corresponding to a reduced C5a receptor fragment was identified.

FIG. 6. Macrophages are immobilized by, adhere to, and degrade C5 and IgG. a, Migration of wild-type peritoneal macrophages, toward Ccl2, across membranes coated with CIV and BSA, C5a, or IgG. * $P<0.05$, # $P<0.01$ compared with BSA. n=3. b, Adhesion of wild-type peritoneal macrophages to slides coated with CIV and C5a or IgG. * $P<0.05$, $P<0.01$ compared to BSA. n=3. c,d, Choroidalmacrophages of 12-month-old wild-type mice clear C5 and IgG in situ. Quantitation shows significantly less C5 (c) and IgG (d) immunoreactivity in sections from 12-14-month-old knockout mice incubated with macrophages (Mϕ) compared with sections without macrophages. * $P<0.05$, # $P<0.01$.n=4-7. e-g, Confocal images from 12-month-old $Ccr2^{-/-}$ mouse eye section incubated with wild-type choroidal macrophages for 2 h. An F4/80 positive (blue) macrophage adheres to the section (e). IgG-immunoreactive material (red) (f) seems closely associated with and engulfed by macrophage in the merged image (g). Scale bar 15 μm.

FIG. 7A-D) is the nucleotide sequence of the human Ccl2 gene (variants, promoter, and enhancer regions) (SEQ ID NO. 1-4).

FIG. 8A-D is the nucleotide sequence of the human Ccr2 gene (variants, isoforms, promoter regions) (SEQ ID NO. 5-8)

FIG. 9 is the nucleotide sequence of the human C5 receptor gene (SEQ ID NO. 9).

FIG. 10 is the nucleotide sequence of the human C5a receptor gene (SEQ ID NO. 10).

DETAILED DESCRIPTION OF THE INVENTION

The inventors have discovered two strains of genetically modified mice that develop many features of AMD as they age. Elderly mice (9-24 months) deficient in the gene for monocyte chemoattractant protein-1 (Ccl2, formerly referred to as MCP-1) (Lu, B et al., (1998) *J Exp Med* 187, 601-8) or its cognate receptor CC chemokine receptor-2 (Ccr2) (Kuziel, et al., (1997) *Proc Natl Acad Sci USA* 94, 12053-8.) develop drusen, lipofuscin, and thickened Bruch's membrane (the extracellular matrix between the RPE and choroid), the earliest manifestations of AMD in humans, as well as intrachoroidal neovascularization. They also develop degeneration of the outer neural retina, which is seen in many patients with AMD (Green, W. R. & Enger, C. (1993) *Ophthalmology* 100, 1519.35). These pathologies are absent in age-matched wild-type mice and several other knockout strains of mice.

The present inventors have discovered that the development of drusen is more pronounced in the Ccl2 mice in comparison to the Ccr2 mice. Also, the accumulation of drusen occurs earlier in the Ccl2 mice. However, $Ccr2^{-/-}$ mice also display evidence of drusen on fundus examination (FIG. 1). Just as Ccl2 deficient mice, Ccr2-deficient mice also exhibit phenotypic variation: some have the discrete hard drusen, while others have confluent drusen.

Figure 2A:
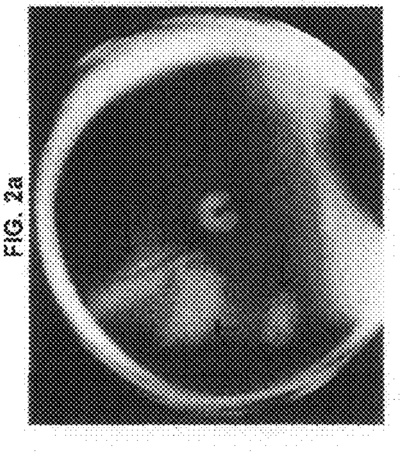
FIG. 2. $Ccl2^{-/-}$- and $Ccr2^{-/-}$ mice develop retinal degeneration. a, Fundus of an 18-month-old $Ccr2^{-/-}$ mouse shows geographic atrophy (arrows). b,c, Electron micrographs show healthy photoreceptor cell bodies in 14-month-old wild-type mouse (b) and attenuated photoreceptors with pyknotic nuclei (arrows) in 16-month-old $Ccl2^{-/-}$mouse (c). d,e, Orderly arrays of photoreceptor outer segments in 14-month-old wild-type mouse (d) and marked degeneration and segments (asterisk) with pigment-laden RPE cells (arrows) amidst disorganized tissue in 16-month-old $Ccl2^{-/-}$ mouse (e). f, RPE of 16-month-old $Ccl2^{-/-}$ mouse shows marked vacuolization (black arrows), degenerated nucleus (black asterisk), and few pigment granules (white arrow). Choroid is filled with abundant melanocytes (white asterisks) but no choriocapillaris vessels. g,h, Retina in $Ccl2^{-/-}$ mouse outside these atrophic areas contains normal photoreceptor cell bodies (g) and outer segments (h). Scale bar 10 μm (b,c,f,g) and 5 μm (d,e,h).
Figure 2B:
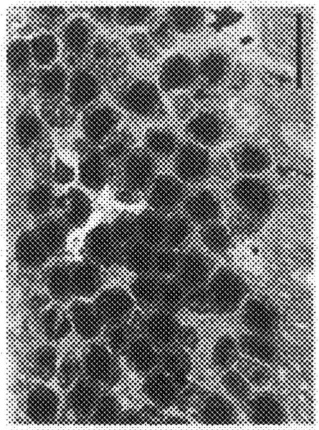
Figure 2C:
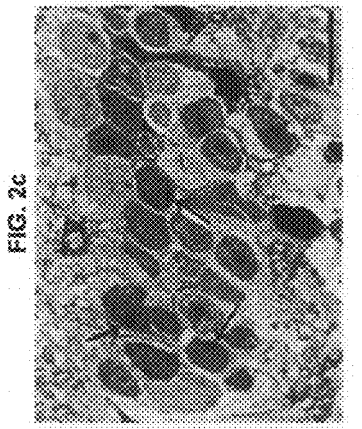
Figure 2D:
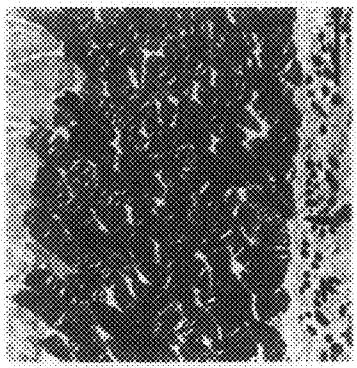
Figure 2E:
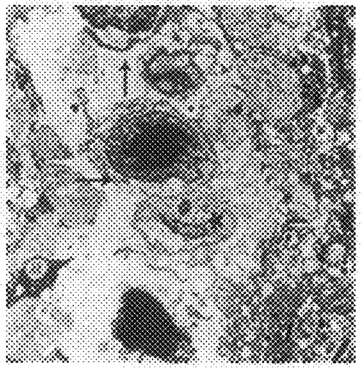
Figure 2F:
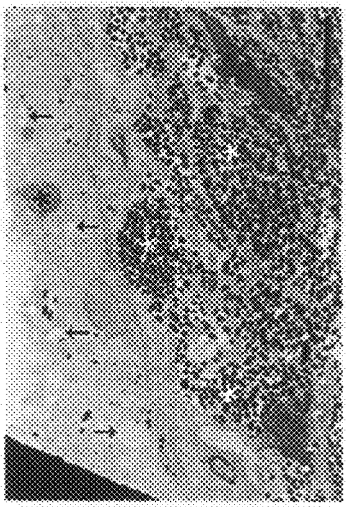
Figure 2G:
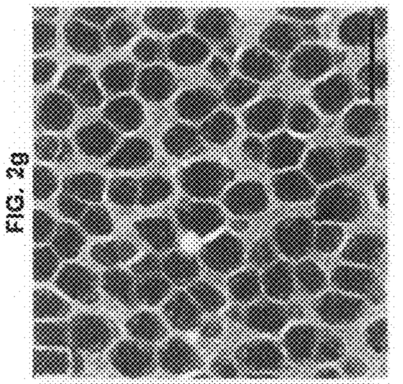
Figure 2H:
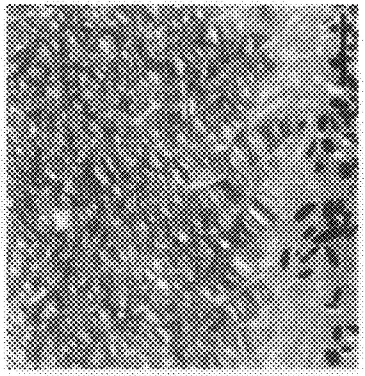
Figure 3A:
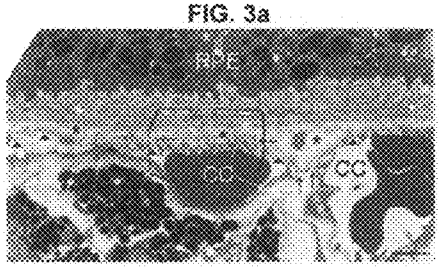
FIG. 3. $Ccl2^{-/-}$ and $Ccr2^{-/-}$ mice develop neovascular AMD and overexpress VEGF in RPE. a-c, Electron micrograph in 20-month-old $Ccl2^{-/-}$ mouse shows dilated choriocapillaries (CC) inserting processes (blue arrows) into Bruch's membrane (BM), with fragmented collagen and elastin layers (asterisks) of BM in a 20-month-old $Ccl2^{-/-}$ mouse. Inner BM (white arrowheads) is intact whereas outer BM (black arrowheads) is breached by choriocapillary processes (blue arrows) and fractures (red arrows). Higher magnification of insets (white area-b and black area-c) shows breaks (red arrows) in outer BM and endothelial processes (blue arrows) inserted into BM, disrupting outer collagenous (black asterisk) and elastin and inner collagenous layers (white asterisks), and largefenestrae (arrowheads) (c). d-f, CNV/ in 24-month-old $Ccr2^{-/-}$ mouse where an endothelial cell (E) and fibrocytes (asterisks) invade sub-RPE space through a defect in BM (arrowheads), disrupting overlying photoreceptors (PR). Higher magnification of insets shows (e) fibrocytes (F) invading BM and disrupting overlying RPE (r) extracellular matrix, and (f) an endothelial cell (E) and fibrocyte processes (asterisks) that have broken through a discontinuity in BM (arrowheads) to displace an RPE cell (R) from its intact monolayer (r). VEGF staining (blue) is minimally present in RPE of 18-month-old wild-type (g) but markedly expressed in RPE and choroid of 18-month-old $Ccl2^{-/-}$ mouse (h). Scale bars 2 μm (a,e,f), 1 μm (b,c), 10 μm (d), and 100 μm (g,h). Intrachoroidal neovascularization leaks indocyanine green but not fluorescein. i, Late phase (12 min) fluorescein angiogram corresponding to area in a-c shows no leakage (arrow) in the region whereas j-l, indocyanine green angiography reveals a focal area (arrow) of hyperfluorescence that increases over time (j-3 min, k-6 min, l-10 min). m,n, Choroidal neovascularization leaks fluorescein. m, Fluorescein angiography shows focal early (2 min) hyperfluorescence (m) that increases both in intensity and area in the late (9 min) frame (n) corresponding to region in d-f.
Figure 3B:
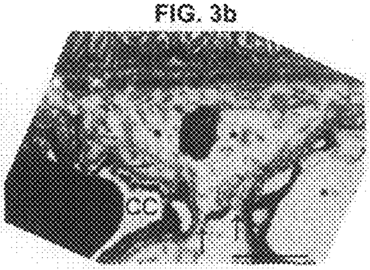
Figure 3C:
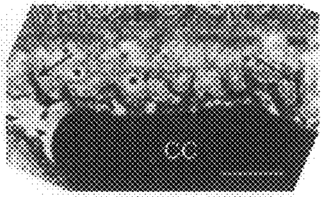

The subretinal deposits observed in the Ccl2 and Ccr2 mice have ophthalmoscopic and angiographic (FIG. 1) characteristics similar to drusen in AMD. Some deposits are discrete while others are confluent like hard or soft drusen, respectively, in patients with AMD (FIG. 1). The deposits are histologically similar to the human counterpart and absent in wild-type mice (FIG. 1). Bruch's membrane is visibly thickened in the knockout mice as in AMD. The choroid is markedly hypervascular and thickened, resembling the histologic appearance of intrachoroidal neovascularization (FIG. 3*a-c*). The outer nuclear layer of the neural retina is markedly attenuated, and photoreceptor inner & outer segments are nearly absent in many regions of the retina (FIG. 2), as seen in human AMD in regions of RPE cells compromised by drusen.

Figures 4A, 4B, 4C, 4D, 4E, 4F, 4G, 4H, 4I:
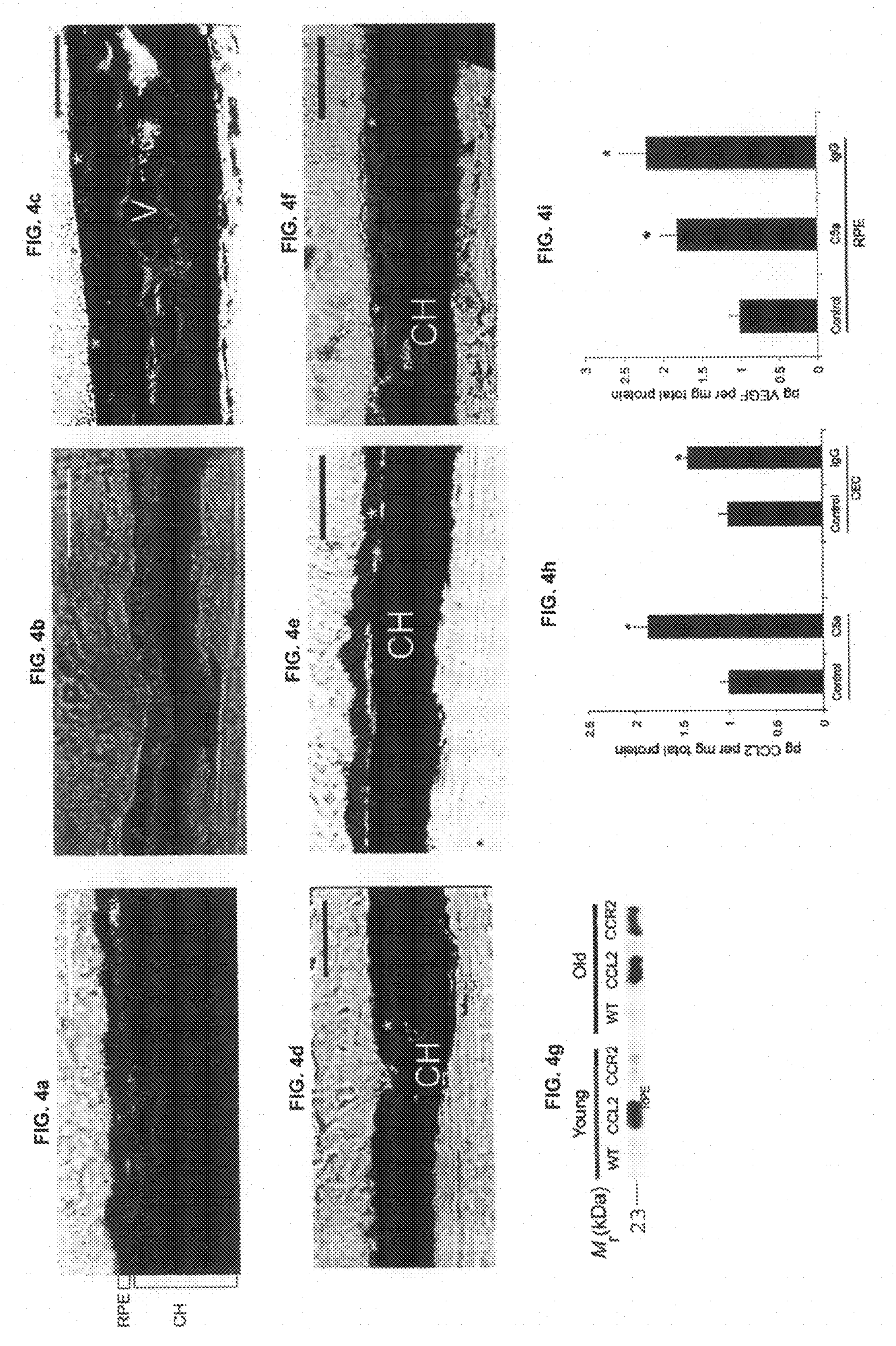
FIG. 4. Complement proteins and IgG deposition in $Ccl2^{-/-}$-and $Ccl2^{-/-}$ mice, and C5a and IgG stimulate Ccl2 and VEGF secretion in RPE cells and CEC. a, Complement C5 (blue) staining in RPE and choroid (CH) of 18-month-old $Ccr2^{-/-}$ mouse. b, IgG staining (blue) in choroid and RPE in 14-month-old $Ccl2^{-/-}$ mouse. c, Colocalization of complement C3c (red) and IgG (green) around choroidal vessel (V) wall and in RPE of 14-month $Ccl2^{-/-}$ mouse. Merged picture shows yellow costaining. d, Vitronectin immunoreactivity in RPE and choroid of 18-month-old $Ccr2^{-/-}$ mouse. c, CD46 staining in RPE of 14-month-old $Ccl2^{-/-}$ mouse. f, Serum amyloid P component staining in RPE and choroid of 14-month $Ccl2^{-/-}$ mouse. RPE, asterisks. Choroid, CH. Scale bar 100 μm (a,b), 25 gm (c), 50 μm (d-f). g, Western blot. RPE and choroid lysates from 6-month-old wild-type (Young WT), 18-month-old wild-type (Old WT), 6-month old $Ccl2^{-/-}$ (Young CCL2), 16-month-old $Ccl2^{-/-}$ (Old CCL2), 6-month-old $Ccr^{-/-}$ (Young CCR2), and 18-month-old $Ccr2^{-/-}$ (Old CCR2) mice were analyzed by antibody against mouse IgG. A 23 kD reactive fragment corresponding to IgG light chain was identified. h, Ccl2 release at 24 h from C5a- stimulated RPE cells and IgG-stimulated choroidal endothelial cells (CEC). i, C5a and IgG upregulate RPE secretion of VEGF at 8 h. Asterisks $P<0.05$.

RPE cells of the knockout mice are engorged with lipofuscin (FIG. 1*g*), autofluorescent lysosomal storage bodies abundant in patients with AMD. Basal membranogranular deposits, the earliest pathological changes in AMD (Green et al., (1993) *Ophthalmology* 100, 1519-35; and Green, et al., (1977) *Trans Am Ophthalmol Soc* 75, 180-254), are seen in Ccl2 −/− mice (FIG. 1). Bruch's membrane was markedly thickened and internally fragmented in these mice, with disruption of the collagen and elastin layers (FIG. 4*d*). The average thickness of Bruch's membrane in nine month-old knockout mice (1.8 μm) is significantly higher than in wild-type mice at the same age (0.45 μm). By comparison, in humans with AMD, the average thickness of Bruch's membrane is approximately 3 μm (Ramrattan, et al., (1994) *Invest Ophthalmol Vis Sci* 35, 2857-64). Lipofusin granules, autofluorescent lysosomal residual bodies that accumulate with age in RPE cells of human, have been implicated in AMD development (Delori et al., 2000) and are found in Ccl-2−/− mice in an age dependent fashion, as is A2E, the principal fluorophore of lipofuscin (FIG. 1*h*).

Choroidal neovascularization (CNV) is observed in Ccl2 mice. FIG. 3 shows leakage due to CNV as captured by indocyanine angiography. FIG. 3*a-c* are transmission electron micrographs of CNV that depicts breaks in Bruch's membrane with choroidal endothelium injecting processes through these breaks. This pathology, which is identical to the earliest event in the development of CNV in human patients with AMD, has not previously been described in a spontaneous model.

Examination of human drusen revealed the presence of C5a within the deposits. It was also found that recombinant complement 5a up-regulates the secretion of Ccl2 in human RIIE cells (FIG. 4*h*). This may explain the presence of subretinal deposits in Ccl2 and Ccr2 deficient mice, which cannot recruit macrophages, which are thought to aid drusen clearance (Duvall and Tso, 1985). This provides a mechanistic link between drusen and macrophage recruitment, and suggests a causal link between the gene defects and the presence of drusen in these knockout mice.

The totality of the data suggests that macrophages play a critical role in drusen resorption, which is impaired in the absence of Ccl2 or its receptor Ccr2. The presence of both drusen and CNV (the respective key findings of both types (non-exudative and exudative) of macular degeneration) in these mice at an age similar to human (adjusted for species longevity) makes this an attractive model for investigating AMD and the role of senescence. This model not only provides evidence for a macrophage role in drusen clearance, but also provides a powerful platform to study the molecular etiology of AMD and the effect of candidate drugs or treatments on the development or progression of AMD.

Figure 3D:
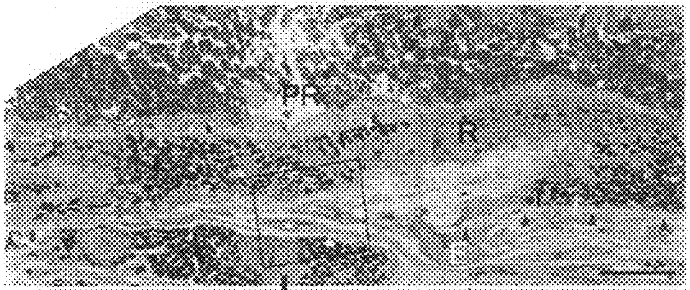
Figure 3G:
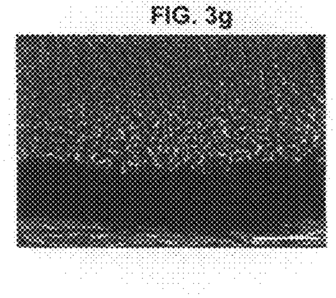
Figure 3E:
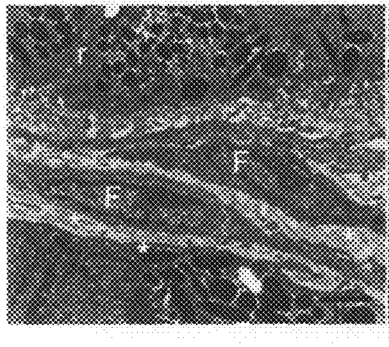
Figure 3F:
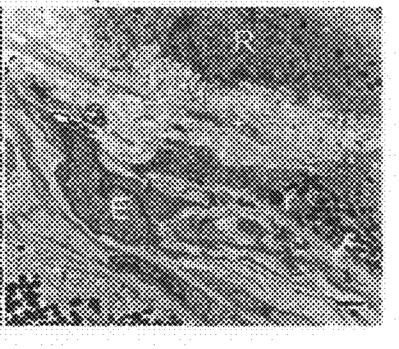

Current animal models of CNV (the neovascular form of AMD that accounts for over 80% of visual loss in patients with AMD) relying on laser injury to fracture Bruch's membrane or viral transfection of VEGF into RPE cells, although useful for experimental study, are poor facsimiles of the human condition. Thus, particularly remarkable was the identification of CNV with frank evidence of angiographic leakage in 4 of 15Ccl2−/−and 3 of 13 Ccr2−/− mice older than 18 months, and in none of 16 age-matched wild-type mice. This frequency of conversion to the neovascular stage is comparable to the rate of progression from drusen to CNV in humans with AMD1. At earlier stages (15-19 months), CNV had breached the outer, but not inner, aspect of Bruch's membrane (intrachoroidal neovascularization), showing angiographic leakage of indocyaninie green but not fluorescein (FIG. 3*a-c, i-l*). This nascent angiogenesis later (18-27 months) completely breached Bruch's membrane, causing RPE and photoreceptor disruption due to the accumulation of subretinal fluid leakage from these immature vessels, which was visible on fluorescein angiography (FIG. 3*d-f, m, n*). It is shown in FIG. 3 that VEGF was overexpressed in the RPE in senescent Ccl2 or Ccr2 deficient, but not age-matched wild-type, mice (FIG. 3*g,h*), consistent with its putative role as the angiogen driving CNV.

Recent evidence suggests that complement activation and immune complex deposition occur in eyes of humans with AMD. (Mullins, et al., FASEB J 14, 835-846 (2000); Johnson, et al., Exp Eye Res 70, 441-449 (2000); and Anderson et al., Am J Ophthalmol 134, 411-431 (2002). The deposition of many of these proteins in aging Ccl2−/− and Ccr2−/− mice was observed in the present studies. Complement component C5 (FIG. 4*a*), immunoglobulin G (IgG) (FIG. 4*b,c,g*), the complement regulatory proteins vitronectin (Vn) and CD46 (membrane cofactor protein) (FIG. 4*d,e*), serum amyloid P component (SAP), a potential activator of the complement cascade (FIG. 4*f*), and advanced glycation endproducts (AGE) (data not shown) were present in RPE or choroid of both strains of knockout mice, but not age-matched wild-types, similar to their distribution in eyes with AMD. Colocalization of IgG and C3c in choroidal vessel walls (FIG. 4*c*) not only suggests the presence of immune complexes, but also reflects ongoing immune deposit formation because C3c, a split-product of surface bound C3b, is cleared within hours. The joint presence of CD46, a membrane-bound regulator that facilitates inactivation of the activated complement components C3b/C4b, and vitronectin, a fluid-phase regulator that binds to the terminal complement complex to regulate complement-mediated lysis, along with localization of complement intermediates suggests that complement activation occurs to completion. These deposits were identified in 6 of 7 Ccl2−/− and 4 of 6 Ccr2−/− mice as young as 6 months of age, predating the changes visible on fundus examination, consistent with a potential causal role. Such deposits were not identified in wild-type mice.

In other immune complex deposition disorders, it has been postulated that these proteins serve as an inflammatory nidus by inciting macrophage recruitment through Fc and complement receptor binding, triggering humoral activation and phagocytosis. Consistent with this hypothesis, it is shown herein that Ccl2 secretion by human RPE and choroidal endothelial cells (CEC) was upregulated by C5a (the activated form of C5) and IgG, respectively (FIG. 4*h*). AGE also stimulates human RPE cell secretion of Ccl2 (ref. 27).

Figure 5B:
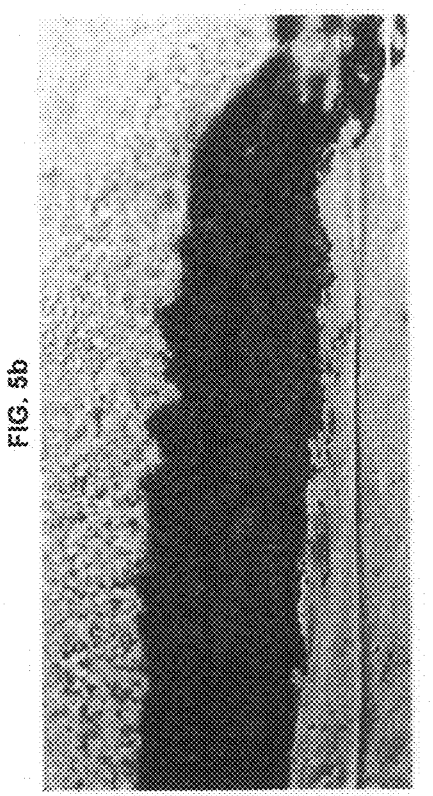
Figure 5E:
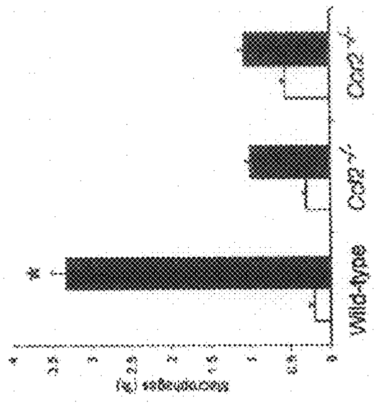
Figure 5A:
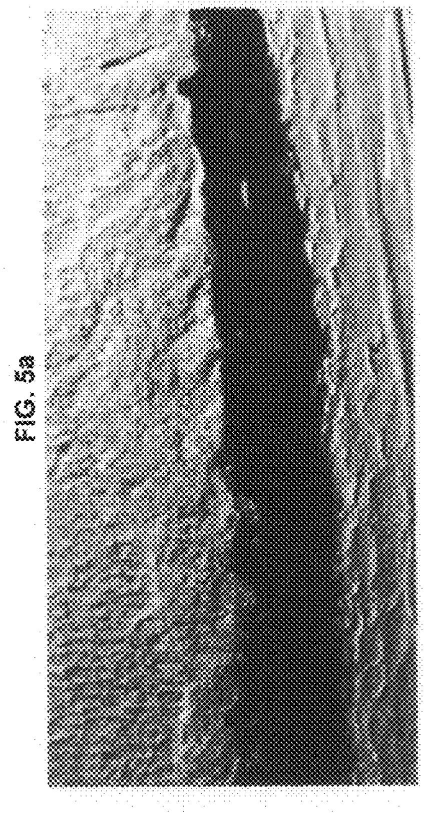
Figure 5D:
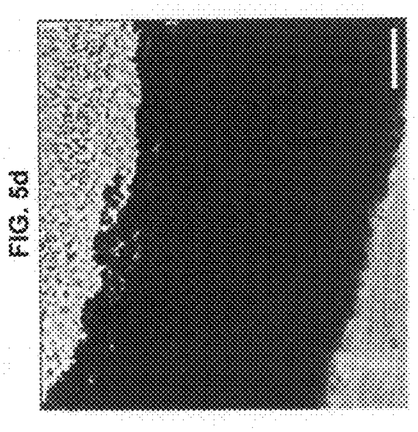
Figure 5C:
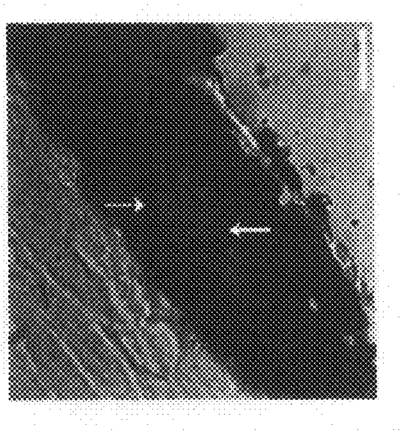
Figure 5F:
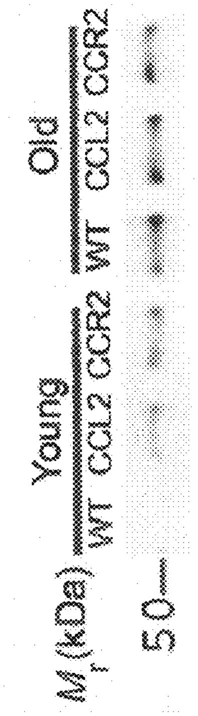

These data may explain the presence of subretinal deposits in Ccl2 and Ccr2 deficient mice which are impaired in recruiting macrophages requisite for clearance and degradation of drusen and other debris. Consistent with this hypothesis, there was an age-dependent increase in the expression of Ccl2 in the RPE (FIG. 5*a,b*), and in macrophage infiltration in the choroid of wild-type mice (FIG. 5*c-e*). Using flow cytometry, we found that aging was associated with a marked increase (15-fold) in the number of macrophages in the choroid of wild-types compared with only a modest (2-3 fold) increase in knockout mice (FIG. 5*e*). These data suggest that macrophage recruitment in aged wild-type mice is principally directed along the Ccl2-Ccr2 axis Along with overexpression of C5 in the RPE and choroid of Ccl2−/− and Ccr2−/−mice, marked upregulation of the C5a receptor (C5aR) in both strains of knockout mice starting at an early age, and in wild-type mice at a later age was observed (FIG. 5*f*). These findings suggest that in the wild-type animal ongoing stimulation by C5a, which upregulates C5aR expression, leads to Ccl2 production and subsequent clearance of C5 and molecules tagged by this opsonin. The inability to summon sufficient numbers of or appropriately stimulated macrophages in knockout mice however, would lead to continued C5 deposition.

Figure 3H:
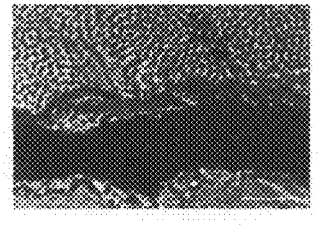
Figure 3I:
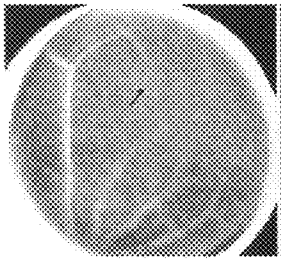
Figure 3J:
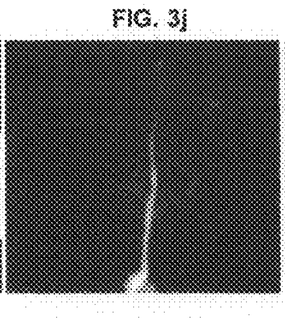
Figure 3K:
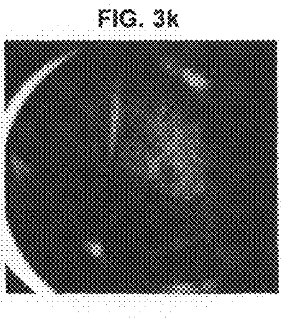
Figure 3L:
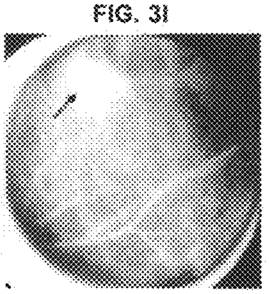
Figure 3M:
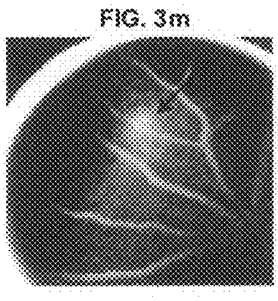
Figure 3N:
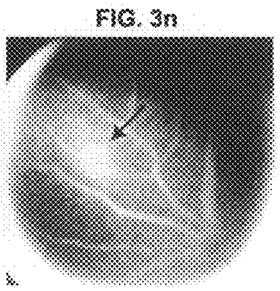

Both C5a and IgG stimulated human RPE cells to increase their secretion of the potent angiogenic cytokine vascular endothelial growth factor (VEGF) (FIG. 4*i*), which is consistent with RPEJ overexpression of VEGF in senescent Ccl2 or Ccr2 deficient mice (FIG. 3*h*). AGE also upregulates human RPE and CEC secretion of VEGF. Together these processes may underlie the development of CNV and highly fenestrated choroidal capillaries (FIG. 1*c*, 3*c*), both of which can be induced by VEGF in these mice.

Figures 6A, 6B, 6C, 6D, 6E, 6F, 6G:
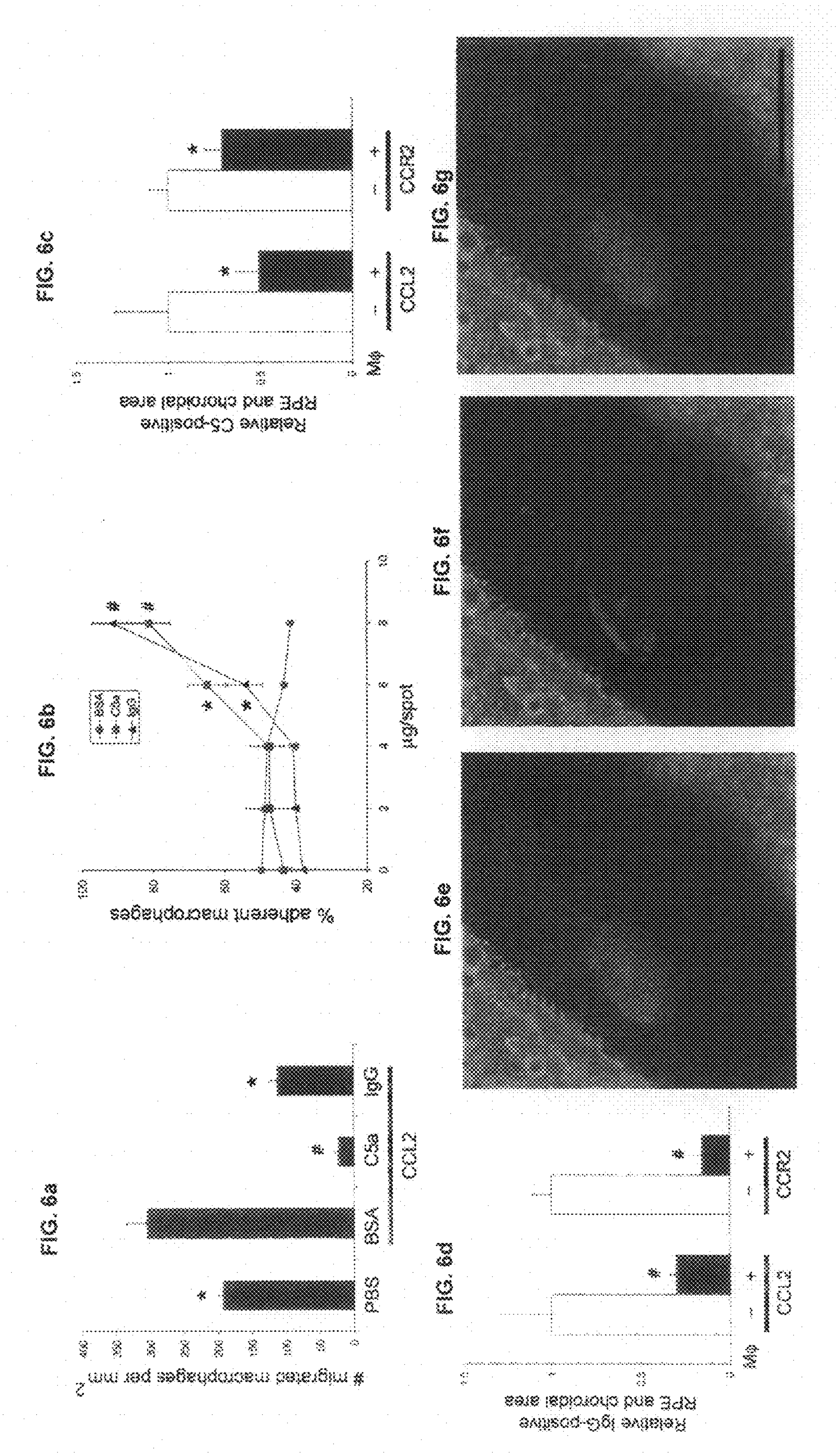

Cell culture inserts were used to examine the migration of macrophages across a porous membrane coated with collagen IV (CIV, an abundant constituent of Bruch's membrane) in response to Ccl2. The migration of macrophages across this CIV-coated membrane when simultaneously coated with C5a or IgG was then tested to determine whether macrophages recruited to these protein-deposition sites by locally secreted Ccl2 are immobilized when they contact these proteins in the extracellular matrix. It was found that Ccl2-induced macrophage chemotaxis was inhibited both by C5a and IgG (FIG. 6*a*). Such immobilization indicates that macrophages adhere to C5a or IgG coated surfaces. Using CIV-coated multi-spot slides coated with C5a or IgG, it was shown that macrophages adhere to these proteins in a dose-dependent fashion (FIG. 6*b*). Collectively these data suggest that macrophages recruited by Ccl2 become immobilized when they contact C5a or IgG and associate with them in the extracellular matrix.

Because macrophages were immobilized by and adhered to C5 and IgG in vitro, and aging was associated with macrophage infiltration into the choroid of wild-type mice. it is possible that these cells scavenge immune complexes identified in the eyes of Ccl2−/− or Ccr2−/− mice. To test this hypothesis, macrophages were purified from aged wild-type choroids by magnetic cell sorting and plated on unfixed eye sections from Ccl2−/− or Ccr2−/− mice which were rich in C5 and IgG deposits in their RPE and choroids. Incubation with wild-type macrophages for 24 hours markedly reduced the total RPE/choroidal area occupied by C5 or IgG, compared with untreated sections (FIGS. 6*c,d*). Within 2 hours, macrophages were spread out over the tissue and intimately associated with protein deposits (FIG. 6*e-g*). These results indicate that macrophages clear C5 and IgG deposits in silu and assign a pivotal role for macrophage deficiency in the accumulation of complement components and immunoglobulins in Ccl2−/− or Ccr2−/− mice.

Thle present invention provides the first animal model of AMD that recapitulates the key elements of the human condition in senescent mice lacking the macrophage chemoattractant Ccl2 or its cognate receptor Ccr2. The presence of similar pathology in two ligand/receptor strains that are defective in induced macrophage trafficking strengthens the hypothesis that macrophage dysfunction plays a role in its pathogenesis. The accumulation of several complement components, complement regulatory proteins, and IgG in these mutant mice, as in humans with AMD, suggests that impaired macrophage recruitment allows accretion of proteins associated with complement activation and immune complex deposition. Inability to summon macrophages is thus associated with senescence-associated development of features strongly reminiscent of human AMD, corroborated by several lines of evidence. In particular the present inventors have shown that Ccl2-driven macrophages are immobilized by and adhere to C5a and IgG in vitro, and that macrophages degrade these proteins in situ. Combined with the observation of a marked deficiency of macrophages in the choroids of aged knockout mice, these data suggest that impaired macrophage mobilization in vivo leads to non-clearing of these proteins since these cells are known to scavenge immune complexes via complement opsonization in vivo.

Since deposition of complement-related proteins and IgG precedes the development of drusen and lipofuscin, it is likely that AMD-like pathology is due, at least in part, to complement activation and immune complex deposition rather than the converse. Because RPE cells in eyes with AMD that are immunoreactive for complement-related proteins and IgG exhibit anatomic prelethal signs it has been suggested that accumulation of these proteins compromises RPE function. The presence of IgG along with complement C3 and C5 intermediates is strongly suggestive of the presence of immune complexes, and is consistent with the presence of circulating retinal auto-antibodies in patients with AMD. Furthermore, patients with membranoproliferative glomerulonephritis, in which complement activation and immune complex deposition cause glomerular injury, develop drusen resembling AMD-associated drusen in ultrastructure and composition, including C5 and IgG deposition, as well as CNV. Collectively these findings support the concept that complement activation and immune complex deposition may injure the RPE in AMD. RPE injury, which may be manifested by secondary photoreceptor degradation, also can be triggered by excessive accumulation of lipofuscin. SAP and TIMP-3 also may impair drusen clearance by functioning as protease inhibitors. RPE overexpression of VEGF stimulated by complement components and IgG combined with fragmentation of Bruch's membrane provides an environment permissive for CNV.

The presence of both atrophic and neovascular pathologies in Ccl2−/− or Ccr2−/− mice at an age corresponding to human senescence makes these mice attractive models for investigating both early and late AMD. Because mouse retina does not contain a specialized macula, this model is not an exact replica of the human condition. However, the pathology in human AMD, while pronounced in the macular area, is not confined to this central region, and the findings observed in aged Ccl2−/− or Ccr2−/− mice closely resemble those of the clinical condition in anatomical appearance, biochemical composition, and functional disruption. More importantly, they define a system for molecular dissection of the determinants of AMD pathogenesis, and provide a platform to develop and validate novel therapeutic strategies and test compounds Ccl2 −/− Ccr2 −/− mice and dual knockout mice, Ccl2 −/−/Ccr2 −/− mice may be used to characterize the temporal development of AMD, preferably from ages of about 9 to about 24 months by ophthalmoscopy, angiography, and histopathology, for example, as compared to wild-type age-matched mice. In characterizing the development of AMD the eyes of these mice are systematically examined at various ages, such as for example, at 1, 3, 6, 9, 12, 18, and 24 months to characterize the temporal development of the retinal and subretinal pathology. For example, the eyes of the mice may be examined by:

1. Clinical Retinal Evaluation—examination & fimdus photography through dilated pupil, e.g., 50 degree fundus photography to quantify yellow spots (drusen);
2. Fluorescein angiography—Staining or leakage within the eye may be identified;
3. Histology Paraffin embedded and frozen sections of affected eyes may be studied for morphology and biochemical composition (lipid, cholesterol, lipofuscin);
4. Immunohistochemistry Drusen (C5a, C5b-9, ApoE, vitronectin, clusterin staining for human correlation); Proliferating cell nuclear antigen (PCNA)+CD31 (proliferating choroidal endothelium); and/or
5. Electron Microscopy—Morphology and morphometry of various structures, e.g., photoreceptors, RPE, Bruch's membrane (integrity and thickness), choroidal vasculature ma)y be examined.

In one aspect of the invention, the Ccl2, Ccr2 and/or Ccl2/Ccr2 (dual knockout) knockout mice may be used to test candidate drugs for treatment of AMD. Dual knockout mice are created by a series of genetic backcrosses using the cross-backcross-intercross scheme, which is well known in the art. Ccr2 −/mice are mated with Ccl2 −/−mice to yield heterozygous F1 offspring. The F1 mice are intercrossed and the progeny screened by PCR, for example, for Ccr2 and Ccl2. B1 progeny, heterozygous for Ccr2 and Ccl2 are intercrossed, and mice homozygous for both disrupted genes are selected for example, by PCR typing for continued backcrossing. Mice are genotyped by any method, such as by analyzing tail DNA samples using Southern blot strategies or by PCR analysis with multiprimer sets that amplify in the disrupted gene, tansgene insert or neomycin resistance gene insert.

Candidate drugs include pharmaceutical compounds, small molecules, peptides, antibodies, antibody fragments and nucleic acids, including oligonucleotides and polynucleotides in sense or antisense orientation and aptamers. In this aspect of the invention the candidate drug is administered to the mouse orally, systemically, e.g., intravenously, intraperitoneally, intravitreously (e.g., by injection or sustained delivery implant), transsclerally or topically, and preferably by topical application to at least one eye of a test group of Ccl2 mice, Ccr2 mice, dual knockout mice or all three types of mutant mice, and the eye(s) of the treated mice are periodically examined to determine the effect of the candidate drug on drusen accumulation, lipofuscin accumulation, Bruch's membrane or any other symptomatic marker of AMD. A decrease in drusen or lipofuscin accumulation or thinning of Bruch's membrane, an affect on retinal degeneration or choroidal neovascularization, for example, is an indication of the ability of the candidate drug to effectively treat AMD.

In one embodiment of the invention, the genetic defect is treated by introducing a wild-type gene Ccl2 or Ccr2 gene into the mouse. Chemotactic deficiency in Ccl2 −/−mice may be reversed by delivering a recombinant vector, such as for example an adeno-associated virus (rAAV) vector expressing the cDNA for Ccl2. Although Ccl2 can be delivered via an osmotic pump, rAAV vector administration is not only as effective as systemic administration, but also confines production and secretion of Ccl2, and is likely to restrict chemotactic activity to the eye. Reconstituting Ccl2 function via AAV transduction is also superior to systemic delivery as the former permits intra-animal inter-eye comparisons, thus providing greater statistical and biological fidelity to the hypothesis testing. Also rAAV vectors have demonstrated long-term, sustained high-level expression in the retina for two years, eliminating the need for pump replacement.

Similarly, the Ccr2 defect may be treated by administering a vector encoding wild-type Ccr2 gene to determine whether rescue of Ccr2 function prevents or causes regression of AMD in Ccr2 mice or dual knockout mice. Alternatively the Ccr2 defect may be corrected by stem cell transplantation of cells from Ccr2+/+ animals, either by adoptive transfer or following bone marrow ablation. Similarly, the Ccl2 defect may be corrected by stem cell transplantation of cells from Ccl2+/+ animals, either by adoptive transfer or following bone marrow ablation, for example.

The rAAV-vector cassette preferably includes a promoter, such as for example a chicken β-actin (CBA) promoter, which preferably is composed of an enhancer element or elements, such as a cytomegalovirus (CMV) immediate-early enhancer (381 bp) and a CBA promoter-exon1-intron1 element (1,352 bp) upstream of a simian virus 40 early splice donor/splice-acceptor site, the Ccl2, gene, or both and a polyadenylation sequence, preferably the simian virus 40 polyadenylation sequence. The entire expression cassette containing the Ccl2 cDNA or Ccr2 cDNA is preferably flanked by AAV2 terminal repeats required for viral packaging. Viral vectors are packaged and purified as described (Raisler, B. J., Berns, K. I., Grant, M. B., Beliaev, D. & Hauswirth, W. W. (2002) *Proc Natl Acad Sci USA* 99, 8909-14). The CBA promoter is preferably used as it supports expression well in both RPE cells and photoreceptors (Acland et al. (2001) *Nat Genet* 28, 92-5).

Efficacy of transduction by the rAAV-CBA-Ccl2, -Ccr2 or vector encoding both Ccl2 and Ccr2 may be confirmed by any method including any combination of the following:

1. In vitro expression: RPE cells harvested and cultured from eyes of wild-type and Ccl2 −/− mice may be probed by PCR amplification for the presence or absence of the wild-type Ccl2 transgene or Ccr2 transgene, respectively. Wild-type RPE cells and mutant RPE cells transfected with rAAV-CBP-Ccl2, -Ccr2 or vector encoding both Ccl2 and CCR2 may be subjected to PCR amplification, and optionally ELISA of the supernatant for expression of Ccl2, which is constitutively secreted (Elner, et al., (1997) *Exp Eye Res* 65, 781-9).
2. In vivo expression: The amount of ocular protein in mice expressed from the vector construct may be assayed after subretinal vector inoculation by ELISA about six weeks after injection. Approximately $10^{10}$ particles ($2\times10^8$ infectious units) in a volume of 1 μl of therapeutic vector is injected into one eye and the same volume of null vector in the fellow eye.
3. AAV-CBA-Ccl2, -Ccr2 or both Ccl2 and Ccr2 is injected into eyes of Ccl2 deficient mice, preferably about eight-week-old Ccl2 deficient, Ccr2-deficient mice, or dual knockout mice, and the temporal development of retinal and subretinal lesions is compared to fellow eyes injected with null vector over 24 months with interval measurements. In addition a vector such as AAV-CBA-Ccl2, AAV-CBA-Ccr2 or both or a single vector encoding both Ccl2 and Ccr2 may be injected into eyes of one-year-old Ccl2 deficient mice, one year old Ccr2 deficient mice or dual knockout mice, and the stabilization or regression of ocular lesions evaluated in comparison to fellow eyes.

In addition Ccl2 and Ccr2 function can be reconstituted by bone marrow transplantation from Ccl2 +/+ or Ccr2 -+/+ mice.

In another aspect of the invention, there is provided a double knockout mouse which has both the Ccl2 and Ccr2 deletions. The mouse may be generated as described above, or by any method known to the skilled practitioner. The mouse is useful for determining the pathology of age-related macular degeneration and testing candidate drugs for treatment of age-related macular degeneration.

It is also contemplated that the genes, vectors and expression vectors of the invention may be used for stem cell transplantation to restore Ccr2 function. For example, stem cells obtained from a normal mouse, i.e., containing a wild type Ccr2 gene, may be introduced either by adoptive transfer or following bone marrow ablation. For example, the normal stem cells may be introduced by intravenous injection into a Ccr2−/− mouse or other animal. The eyes of the animal receiving the stem cell transplant are then observed to determine the effect of the transplantation. Alternatively, a Ccr2−/−mouse or other animal can be subjected to bone marrow irradiation to deplete stem cells. Following ablation of the endogenous stem cells, stem cells obtained from a wild type mouse are administered to the irradiated Ccr2−/− mouse, preferably by intravenous injection. The eyes of the transplanted mouse are then observed to determine the effect of the transplantation. Similar procedures can be employed to restore Ccl2 function in a Ccl2−/− mouse or other animal.

It is also contemplated that AMD can be treated or prevented in mammals, including humans, by administering to a patient in need, a wild type Ccr2 gene, wild type Ccl2 gene or both to compensate for a defective Ccr2 gene or Ccl2 gene or both. The wild type gene can be administered by any method known in the art, such as by administering the gene(s) via an expression vector, such as a replication defective adenovirus vector, directly into the eye, via an implant or via intravenous injection. Alternatively, the wild type gene can be introduced into the eye via stem cell transplantation as described above.

It is further contemplated that wild type Ccl2 and/or Ccr2 genes or small molecules that promote the function of Ccl2 and/or Ccr2 are used for the manufacture of a medicament for the treatment or prevention of AMD in a mammal.

It is further contemplated that the genes, vectors and expression vectors, including the promoter/enhancer regions of the genes for Ccl2 and/or Ccr2 may be used in identifying mutations or polymorphisms that place people at increased or decreased risk for developing AMD. The human Ccl2 gene, its promoter and enhancer (SEQ ID NO. 1-4) and human Ccr2 gene and its promoter (SEQ ID NO. 5-8) are shown in FIGS. 7A-D and 8A-D, respectively. These sequences can be used to isolate the Ccr2 and/or Ccl2 gene from genomic DNA obtained from patients suspected of having or believed to be at risk of developing age-related macular degeneration. Also, the wild type Ccl2 and/or Ccr2 sequences or fragments thereof can be used directly or oligonucleotides based on these sequences can be generated and used to screen genomic or cDNA AMD libraries using any method known in the art. Generally, high stringency conditions are used in the screening process. Methods for screening genomic DNA and gene libraries and selection of stringency conditions are well known to those of skill in the art. See, e.g, Maniatis et al., Molecular Cloning A laboratory Manual. The isolated genes or gene fragments can then be sequenced to determine the presence of mutations in the isolated DNA. Once specific AMD mutations or polymorphisms are identified, these mutations can be used to screen patients for the presence of the mutation:

Applicants' studies have shown that C5 and C5a accumulate in the eyes of the Ccl2−/− and Ccr2−/− mice with aging, and that the inability of macrophages to clear these deposits leads to macular degeneration-like changes in the mice. Thus, defects in the C5 receptor and C5a receptor genes may promote macular degeneration. Therefore, an analysis of the C5 receptor gene and C5a receptor genes in AMD patients for the presence or absence of mutations or polymorphisms will confirm the role of these genes in the development of AMD. The sequence of each of the human C5 receptor and C5a receptor genes is shown in SEQ ID NO.9 and 10, respectively. As discussed above for the Ccl2 and Ccr2 genes, the wild type C5 receptor and C5a receptor genes may be used to screen AMD libraries or genomic DNA obtained from AMD patients for the C5 receptor and C5a receptor genes therein and the genes so isolated can be characterized, by nucleotide sequencing to determine the presence or absence of mutations or polymorphisms, for example. Also, the C5 receptor and C5a receptor genes may be cloned into an appropriate expression vector or expression vector and further characterized.

EXAMPLES

Animals: Wild-type C57BL/6 mice (Jackson Laboratories), and Ccl2−/− and Ccr2−/− strains, generated as described previously (Lu, et al., J Exp Med 187, 601-608 (1998); Kuziel, et al, Proc Natl Acad Sci USA 94, 12053-12058 (1997)) (incorporated herein by reference) and backcrossed 10 times to C57BL/6, were anesthetized by intramuscular injection of ketamine (50 mg/kg) and xylazine (10 mg/kg).

Fundus photography and angiography: Photographs and angiograms performed after intraperitoneal injection of fluorescein sodium (Akorn; 60 mg/kg) or indocyanine green (Sigma-Aldrich; 6 mg/kg) were captured with a TRC-501A camera (Topcon) and evaluated by two masked readers.

Immunohistochemistry and electron microscopy: Frozen sections fixed in Histochoice MB (Amresco) and blocked with 5% donkey serum (Jackson Immunoresearch) were stained with rabbit anti-mouse C3c (1:1000, gift of J. D. Lambris, University of Pennsylvania, Philadelphia, Pa.), mouse anti-mouse C5 (1:1000; gift of J. D. Lambris), rabbit anti-human CD46 (1:500; Santa Cruz Biotechnologies), goat anti-mouse MCP-1 (15 micro g/ml; R&D Systems), goat anti-human SAP (1:500; Santa Cruz), rabbit anti-mouse TIMP-3 (1:2500; gift of B. H. F. Weber, University of Wuerzburg, Wuerzburg, Germany), goat anti-mouse VEGF (15 micro g/ml; R&D Systems), rabbit polyclonal anti-AGE antibodies (1:1000, gift of A. Gugliucci, Touro University, Vallejo, Calif.), or goat anti-human vitronectin (1:500; Santa Cruz). Bound antibodies were detected with Cy3-conjugated goat secondaries or Cy5-conjugated donkey secondaries (1:100; Jackson Immunoresearch). Alternatively sections were stained directly with FITC-conjugated goat anti-mouse IgG (1:100; BD Pharmingen), Cy5-conjugated donkey anti-mouse IgG (1:00; Jackson Immunoresearch) or Cy5-conjugated F4/80 (5 micro g/ml; Serotec). A "mouse-on-mouse" kit (Vector Laboratories) was used for C5 staining. Lipofuscin autofluorescence was detected through the Cy3 channel: Transmission electron microscopic studies were performed on uranyl acetate/lead citrate-stained ultrathin sections. Bruch's membrane thicknesses were measured 150 micro m from the optic nerve by averaging thinnest and thickest parts.

Western blotting: Equal amounts of total protein from RPE/choroid were resolved in SDS 4-20% polyacrylamide gradient gel and transferred to nitrocellulose membranes for western blotting with antibodies against mouse C5aR (gift of J. D. Lambris) or mouse IgG (Transduction Laboratories).

Flow cytometry: Single cell suspensions of RPE/choroids were incubated in Fc block (0.5 mg/ml BD Pharmingen) for 15 min on ice, stained with Cy5-F4/80 antibody (1:30), and live cells were detected by gating on forward versus side scatter, followed by analysis of F4/80 in the fluorescence channel (FACScalibur, BD Biosciences).

Migration: Wild-type peritoneal macrophage migration (10,000 cells/well) toward 30 nM of mouse Ccl2 (R&D Systems) was assayed using 24-well transwell chambers (Corning) separated by a 5 micrometer polycarbonate filter coated with 50 micro g/ml collagen IV (CIV; Fluka), with or without overlay of human C5a (50 nM; Calbiochem), mouse IgG (50 micro g/well; Jackson Immunoresearch), or bovine serum albumin (BSA; 50 micro g/well; Sigma-Aldrich), by counting numbers of migrated cells after 3 hours incubation at 37 degrees C.

Adherence: Adherence of wild-type peritoneal macrophages (105 cells/spot) plated on multispot glass slides (Shandon) coated with 50 micro g/ml CIV overlaid with human C5a, mouse IgG, or BSA (0-8 micro g/spot) was quantitated using CyQuantGR (Molecular Probes) after incubation at 37 degrees C. for 1 h.

Degradation: Frozen unfixed eye sections from knockout mice were transferred to 24-well culture plates and incubated with or without wild-type (12-month-old) choroidal macrophages (10,000 cells/well), purified via magnetic cell sorting using MicroBeads conjugated with CD 11b antibody (clone M1/70.15.11.5; Miltenyi Biotec), for up to 24 h at 37 degrees C. Sections were fixed with Histochoice MB, stained for C5, IgG, or F4/80, and imaged by scanning confocal microscopy. Relative areas of C5 or IgG immunoreactivity were measured for 4-7 sections using image-analysis software (Photoshop, ver. 6.0 Adobe Systems).

Cell stimulation: Serum starved human CEC (gift of D. R. Hinton, University of Southern California, Los Angeles, Calif.) and human RPE cells were stimulated with human C5a (50 ng/ml) or immobilized human IgG (50 micro g/well; Sigma-Aldrich) after attaining 80% o confluence. Ccl2 and VEGF levels measured by ELISA (R&D Systems) at 8 and 24 h after stimulation were normalized to total protein.

MALDI-TOF mass spectrometry: RPE extracts and standards of synthetic N-retinylidene-N-retinylethanolamine (A2E; gifts of E. Rodriguez-Boulan, New York University, N.Y. New York and G. H. Travis, University of California, Los Angeles, Calif.) were dissolved in 50% methanol/50% water (Fisher Scientific), transferred to C18 PrepSep solid phase extraction columns (Fisher), and eluted with 1 ml methanol containing 0.1% trifluoroacetic acid (TFA; Fisher). N-perfluoroalkyl pyridine (NPP; gift of S. Rankin, University of Kentucky, Lexington, Ky.; 250 ng) was added to samples as an external standard. The MALDI target was prepared by adding 0.5 micro 1 sample to deposited 0.5 micro 1 matrix (alpha-cyano-4-hydroxycinnamic acid; Sigma-Aldrich). Positive ion spectra were acquired on a Bruker Autoflex MALDI-TOF mass spectrometer (Bruker Daltonic). The A2E response (m/z 592.5) was normalized to the NPP response (m/z 576.1).

Statistics: Data are represented as the mean ±s.e.m. of at least 3 independent experiments and were compared using a two-tailed Student's t-test. The null hypothesis was rejected at $P<0.05$.

Example 1

Eyes of greater than 60 Ccl2/and Ccr2−/− mice and 40 age-matched wild-type mice ranging from 3 to 27 months were subjected to fundus examination. Of these, eyes from 25 Ccrl−/−, 21 Ccr2−/− and 18 age-matched wild-type (<12 months: 6; 12-24 months: 7; >24 months: 5) mice were extensively examined histopathologically. Before 9 months of age, the fundi of Ccl2/ and Ccr2−/mice were indistinguishable from wild-type mice. Thereafter subretinal deposits with ophthalmoscopic and pathologic features of drusen in patients with AMD were observed in all mice of both knockout strains and increased in number with age as in humans (FIG. 1*a, b*). In contrast, no such changes were visible in wild-type mice even at 24 months of age (n=5). Bruch's membrane (the extracellular matrix between the RPE and choroid) was markedly thickened in senescent Ccl2 or Ccr2 deficient mice compared with age-matched wild-types and that its collagen and elastin layers were severely disrupted with internal fragmentation (FIG. 1*e*), features observed in AMD. As in patients with AMD, intense immunostaining of tissue inhibitor of metalloproteinases (TIMP)-3, produced by the RPE and thought to contribute to thickening of Brach's membrane, was observed in aged knockout mice (FIG. 1*e*). As Ccl2−/− and Ccr2−/− mice aged, increasing amounts of lipofuscin granules (autofluorescent lysosomal residual bodies which accumulate with age in RPE cells of humans and have been implicated in AMD development) were observed in swollen and vacuolated RPE cells (FIG. 1*f, g*) at 9 months and thereafter. Ultrastructural analysis of these RPE cells showed significant intracellular accumulation of dense bodies (FIG. 1*h*) including large ellipsoid and spherical structures of high electron density, presumably representing melanosomes and melanolipofuscin fusion particles, respectively, and numerous smaller structures of variable density representing lipofuscin granules. RPE extracts were tested for the presence of N-retinylidene-N retinylethanolamine (A2E), the principal lipofuscin fluorophore by matrix-assisted laser desorption/ionization-time-of-flight (MALDI-TOF) mass spectrometry. RPE extracts from 12-month-old knockouts contained 25 pmol of A2E per eye (FIG. 1*i*). No A2E was detected in RPE of age-matched wild-type mice. Lipofuscin accumulation is thought to promote RPE dysfunction in AMD.

Example 2

Retinal Degeneration and Choroidal Neovascularization in Ccl2−/− and Ccr2−/−mice As Ccl2−/− and Ccr2−/− mice aged, they exhibited several of the late findings seen in human AMD, including progressive outer retinal degeneration and CNV, similar to that seen in patients with late AMD. Despite evidence of RPE and choroidal pathology, differences in neural retinal morphology between knockout strains and wild types were not observed before 16 months of age. At 16 months of age and thereafter, both knockout strains exhibited confluent areas of visible atrophy similar to "geographic atrophy" seen in advanced AMD (FIG. 2*a*). These areas were characterized by cell loss in the outer nuclear layer of the retina and atrophy of photoreceptor segments (FIG. 2*b-e*), as well as attenuation of the RPE and choriocapillaris (FIG. 2*f*) as in late AMD. In these regions the RPE was hypopigmented along with prominent vacuolization and degeneration of most intracellular organelles, and was devoid of basal infoldings. The choriocapillaris was nearly obliterated with few or no patent inner choroidal vessels observed in the areas corresponding to fundus atrophy. Regions outside these areas did not display such atrophy (FIG. 2*g,h*).

Example 3

CCR2 rescue of the ocular abnormalities in Ccr2 deficient mice is accomplished by creating chimeric mice using bone marrow transplantation (BMT). In vitro AAV transduction results in loss of stem cell activity during infection, while in vivo transduction results in non-specific and low-level target expression (only 1 per 15,000 bone marrow cells are stem cells); neither approach will guarantee sustained expression in vivo. Ccr2 −/− mice are irradiated and repopulated with bone marrow stem cells from wildtype Ccr2 +/+ mice. Ccr2 −/mice are maintained on antibiotic-containing water for one week before irradiation. These mice are irradiated with 900 cGy from a cesium source (delivered in two equal doses of 450 cGy 3-4 hours apart), and donor bone marrow cells ($1\times10^7$) are injected into a tail vein. Mice are maintained on antibiotic containing water for four weeks after transplantation. Engraftment is verified by PCR detection of the Ccr2 gene in the bone marrow of all irradiated mice. Eyes of eight-week-old chimeric mice are compared to ungrafied Ccr2 −/− mice over 24 months with interval measurements. In addition, eyes of Ccr2 −/− mice repopulated with bone marrow at one year of age are compared to ungrafied mice over the following year.

Example 4

A candidate drug for the treatment of AMD is applied to one or both eyes of a Ccl2 mouse, which was previously confirmed to have developed AMD symptoms, e.g., drusen and/or lipofuscin deposits in the eye, thickening of Bruch's membrane. Treatment is repeated at least once daily for one to several weeks. Examination of the treated eye(s) by visual and/or fundus examination through dilated pupil is carried out periodically during treatment and the effect of treatment is compared to placebo treated wild-type eyes.

What is claimed is:

1. A method for testing a candidate drug for treatment of age-related macular degeneration (AMD) comprising:

(i) administering the candidate drug to at least one eye of a Ccl2−/−/Ccr2−/− dual knockout mouse, wherein the at least one eye exhibits at least one symptom comprising drusen accumulation, lipofuscin accumulation, thickening of Bruch's membrane, retinal degeneration, choroidal neovascularization, or a combination thereof, (ii) determining the effect of the candidate drug on the at least one symptom, and (iii) correlating the effect of the test compound on the at least one symptom with a potential utility to treat AMD.

2. The method of claim 1 wherein the candidate drug is nucleic acid.

3. The method of claim 2 wherein the candidate drug comprises a viral vector encoding wild-type Ccl2.

4. The method of claim 1 wherein the candidate drug comprises a viral vector encoding wild type Ccr2.

5. The method of claim 1 wherein step (ii) comprises analyzing the at least one eye to determine amount and type of drusen or lipofuscin accumulation, extent of retinal degeneration, or neovascularization developed therein or a combination thereof.

6. The method according to claim 1 wherein the at least one eye is analyzed by ophthalmoscopy, angiography, histopathology or a combination thereof.

7. The method of claim 1 wherein the candidate drug is administered to the mouse orally, intravenously, intraperitoneally, intravitreously, transsclerally or topically.

8. The method of claim 7 wherein the candidate drug is administered topically to at least one eye of the mouse.

9. The method of claim 1 wherein the candidate drug is a pharmaceutical compound, small molecule, peptide, antibody, antibody fragment, aptamer or nucleic acid.

10. The method of claim 9 wherein the nucleic acid is an oligonucleotide or polynucleotide in either the sense or antisense orientation or an aptamer.

11. A method of screening a candidate drug for potential utility for treatment of age-related macular degeneration, comprising:

(a) providing a Ccl2−/−/Ccr2−/− dual knockout mouse which exhibits drusen accumulation, lipofuscin accumulation, thickening of Bruch's membrane, retinal degeneration, choroidal neovascularization, or a combination thereof in at least one eye;

(b) administering the candidate drug to the knockout mouse;

(c) determining the effect of the candidate drug on drusen, lipofuscin deposition, retinal degeneration, and/or choroidal neovascularization in at least one eye of the knockout mouse; and (d) correlating the effect of the candidate drug on drusen, lipofuscin accumulation, retinal degeneration, and/or choroidal neovascularization with a potential utility to treat age-related macular degeneration.

12. The method of claim 11 wherein the candidate drug is administered topically to at least one eye of the mouse.

13. The method of claim 11 wherein the candidate drug is nucleic acid.

14. The method of claim 11 wherein the candidate drug comprises a viral vector encoding wild-type Ccl2.

15. The method of claim 11 wherein the candidate drug comprises a viral vector encoding wild type Ccr2.

16. The method of claim 11 wherein step (c) comprises analyzing the at least one eye to determine amount and type of drusen or lipofuscin accumulation, extent of retinal degeneration, or neovascularization developed therein or a combination thereof.

17. The method according to claim 11 wherein the at least one eye is analyzed by ophthalmoscopy, angiography, histopathology, mass spectometry or a combination thereof.

18. The method of claim 11 wherein the candidate drug is administered to the mouse orally, intravenously, intraperitoneally, intravitreously, transsclerally or topically.

19. The method of claim 11 wherein the candidate drug is a pharmaceutical compound, small molecule, peptide, antibody, antibody fragment, aptamer or nucleic acid.

20. The method of claim 19 wherein the nucleic acid is an oligonucleotide or polynucleotide in either the sense or antisense orientation or an aptamer.

21. A Ccl2−/−/Ccr2−/− dual knockout mouse which exhibits at least one symptom comprising drusen accumulation, lipofuscin accumulation, thickening of Bruch's membrane, retinal degeneration, choroidal neovascularization, or a combination thereof in at least one eye.

22. The method of claim 7 wherein the candidate drug is administered intravitreously by injection or by sustained delivery implant, to at least one eye of the mouse.

23. The method of claim 7 wherein the candidate drug is administered transsclerally to at least one eye of the mouse.

24. The method of claim 11 wherein candidate drug is administered intravitreously by injection or by sustained delivery implant, to at least one eye of the mouse.

25. The method of claim 11 wherein the candidate drug is administered transsclerally to at least one eye of the mouse.

26. The method of claim 18 wherein, the candidate drug is administered transsclerally to at least one eye of the mouse.

27. The method of claim 1 wherein the candidate drug comprises stem cells obtained from a wild-type mouse and intravitreously injected into the Ccl2−/−/Ccr 2−/− dual knockout mouse.

28. The method of claim 11 wherein the candidate drug comprises stem cells obtained from a wild-type mouse and injected intravitreously into the Ccl2−/−/Ccr2−/− dual knockout mouse.

* * * * *

SEQUENCE LISTING

```
<160> NUMBER OF SEQ ID NOS: 10

<210> SEQ ID NO 1
<211> LENGTH: 757
<212> TYPE: DNA
<213> ORGANISM: Homo sapiens

<400> SEQUENCE: 1

ggaaccgaga ggctgagact aacccagaaa catccaattc tcaaactgaa gctcgcactc      60

tcgcctccag catgaaagtc tctgccgccc ttctgtgcct gctgctcata gcagccacct     120
```

tcattcccca agggctcgct cagccagatg caatcaatgc cccagtcacc tgctgttata 180
acttcaccaa taggaagatc tcagtgcaga ggctcgcgag ctatagaaga atcaccagca 240
gcaagtgtcc caaagaagct gtgatcttca agaccattgt ggccaaggag atctgtgctg 300
accccaagca gaagtgggtt caggattcca tggaccacct ggacaagcaa acccaaactc 360
cgaagacttg aacactcact ccacaaccca agaatctgca gctaacttat tttcccctag 420
ctttccccag acaccctgtt ttattttatt ataatgaatt ttgtttgttg atgtgaaaca 480
ttatgcctta agtaatgtta attcttattt aagttattga tgttttaagt ttatctttca 540
tggtactagt gtttttttaga tacagagact tggggaaatt gcttttcctc ttgaaccaca 600
gttctacccc tgggatgttt tgagggtctt tgcaagaatc attaatacaa agaatttttt 660
ttaacattcc aatgcattgc taaaatatta ttgtggaaat gaatattttg taactattac 720
accaaataaa tatatttttg tacaaaaaaa aaaaaaa 757

<210> SEQ ID NO 2
<211> LENGTH: 743
<212> TYPE: DNA
<213> ORGANISM: Homo sapiens

<400> SEQUENCE: 2
agactaaccc agaaacatcc aattctcaaa ctgaagctcg cactctcgcc tccagcatga 60
aagtctctgc cgcccttctg tgcctgctgc tcatagcagc caccttcatt ccccaagggc 120
tcgctcagcc agatgcaatc aatgccccag tcacctgctg ttataacttc accaatagga 180
agatctcagt gcagaggctc gcgagctata gaagaatcac cagcagcaag tgtcccaaag 240
aagctgtgat cttcaagacc attgtggcca aggagatctg tgctgacccc aagcagaagt 300
gggttcagga ttccatggac cacctggaca agcaaaccca aactccgaag acttgaacac 360
tcactccaca acccaagaat ctgcagctaa cttattttcc cctagctttc cccagacacc 420
ctgttttatt ttattataat gaattttgtt tgttgatgtg aaacattatg ccttaagtaa 480
tgttaattct tatttaagtt attgatgttt taagtttatc tttcatggta ctagtgtttt 540
ttagatacag agacttgggg aaattgcttt tcctcttgaa ccacagttct acccctggga 600
tgttttgagg gtctttgcaa gaatcattaa tacaaagaat ttttttaac attccaatgc 660 attgctaaaa tattattgtg gaaatgaata ttttgtaact attacaccaa ataaatatat 720
ttttgtacaa aaaaaaaaaa aaa 743

<210> SEQ ID NO 3
<211> LENGTH: 3221
<212> TYPE: DNA
<213> ORGANISM: Homo sapiens

<400> SEQUENCE: 3
ccgagatgtt cccagcacag ccccatgtga gagctccctg gctccgggcc cagtatctgg 60
aatgcaggct ccagccaaat gcattctctt ctacgggatc tgggaacttc caaagctgcc 120
tcctcagagt gggaatttcc actcacttct ctcacgccag cactgacctc ccagcggggg 180
agggcatctt ttcttgacag agcagaagtg ggaggcagac agctgtcact ttccagaaga 240
ctttcttttc tgattcatac ccttcacctt ccctgtgttt actgtctgat atatgcaaag 300
gccaagtcac tttccagaga tgacaactcc ttcctgaagt agagacatgc ttccaacact 360
cagaagccta tgtgaacact cagccagcaa agctgggaag tttttctctg tgaccatggg 420
ctaattggtc tccttctctg gattgtggct ttatcagata aaaacaagtg gtcatgccac 480
aggatgtcta taagcccatt gattctggga ttctatgagt gatgctgata tgactaagcc 540
aggagagact tatttaaaga tctcagcatc tttcagcttg ttaacctaga gaaaacccga 600
agcatgactg gattataaag ggaaattgaa tgcggtccac caagttcatg gtaaaggatg 660
cactaacaga ttagagagag gtttcccctg atatgaggaa aacttcttgg aagatgaggt 720
gagatggcct aggaagaaat tcctacacaa aattgcacag tctctagtcc tggaaacatt 780
ttattcattg gataagaatg gattgaggca tgagcagagg actgagacaa acacagagaa 840
gtttcaacac tggttgggga gaaaaggagt aactagtgag attcaggcag aacaagaata 900
aggctcctca agaggcacaa gcaaagcagg gctcgagttg atttgttctc tcttcatcct 960
gctttttgta attccaccag agtctgaaat gaccactcca tagagtctct gctctgggat 1020
tctccaggaa accaatatcc atcatgagac atcaagtcta gtcccaggaa gaagagattc 1080
tggaatggaa acatcctggg tgggagtctc agcacatcta ctattctgtc tgagttactg 1140
gacaaataac ttcagtttta acctaacgaa agctgggttg gttggaggac tgggcaggca 1200
gcgctggaaa gtatgtcagc accatacctg actccctgaa tgcactcaac aatgccatta 1260
ctgaccactt actagaaata aaacagtcat ttgttgaata caacccgttt ctttttacaa 1320
gtgtagtgaa aagtgttttc tttcaagaaa ccccatgcat ttatagacat tgcctcagtg 1380
accctttatg aaagaagtca ctagtctttg tatgcccatt gggcaagggc accgcaaggc 1440
tcagaaggag gaggcagtgg gctaggagaa tggagagatc agaattttaa actcagccca 1500
gccattaaca tgcctcaagt actcctatca tatttgtaag agacaacagt tcactgaaat 1560
gaattctaag gtctttgggt ttttatcagt gtgcttctgt agtttctgag gaaatctaag 1620
gcacaactga ggaatgaagt caggctttcc aattcccgaa atactcctcc actgcttact 1680
catgtccctt ggaaattaag aaggaagcca ggagaatagc tgccataacc agggatgaac 1740
ttcttgtcca ctgctgcctg ctatgctagc aacagcctcc taactcataa tgacttagcc 1800
atgaggaatg tttctagatt ctcctttagc tgtctgccca tttggaagat gctgaggaca 1860
gagagaggac ccaagcaggc aactagttgg aggacttgta cacgtttcct tccagcagta 1920
tgtcagagag gtgagcagcc cactggggac agggctgcct gggttctgtg ctcgagggga 1980
ccttgagcag gctatttaac ccttctgtgc ctcagttgcc tgatctataa catgaaaatt 2040
agcaatccct actagataaa gttggggaat ttacagagtt aatatttgta aaggtctgag 2100
aatattcctg gcagagtaag cactctgtga gtatgacact ggcatttctt ctgcagcact 2160
acatgctgtc tatgcctttg tccaagtctg aaaccctaga actcttagaa ttcagttcaa 2220
tgtttacaca atcctacagt tctgctaggc ttctatgatg ctactattct gcatttgaat 2280
gagcaaatgg atttaatgca ttgtcaggga gccggccaaa gcttgagagc tccttcctgg 2340
ctgggaggcc ccttggaatg tggcctgaag gtaagctggc agcgagcctg acatgctttc 2400
atctagtttc ctcgcttcct tccttttctg cagttttcgc ttcacagaaa gcagaatcct 2460
taaaaataac cctcttagtt cacatctgtg gtcagtctgg gcttaatggc accccatcct 2520
ccccatttgc tcatttggtc tcagcagtga atggaaaaag tgtctcgtcc tgaccccctg 2580
cttccctttc ctacttcctg gaaatccaca ggatgctgca tttgctcagc agatttaaca 2640
gcccacttat cactcatgga agatccctcc tcctgcttga ctccgccctc tctccctctg 2700
cccgctttca ataagaggca gagacagcag ccagaggaac cgagaggctg agactaaccc 2760
agaaacatcc aattctcaaa ctgaagctcg cactctcgcc tccagcatga aagtctctgc 2820
cgcccttctg tgcctgctgc tcatagcagc caccttcatt ccccaagggc tcgctcagcc 2880

-continued aggtaaggcc ccctcttctt ctccttgaac cacattgtct tctctctgag ttatcatgga 2940
ccatccaagc agacgtggta cccacagtct tgctttaacg ctacttttcc aagataaggt 3000
gactcagaaa aggacaaggg gtgagcccaa ccacacagct gctgctcggc agagcctgaa 3060
ctagaattcc agctgtgaac cccaaatcca gctccttcca ggattccagc tctgggaaca 3120
cactcagcgc agttactccc ccagctgctt ccagcagagt ttggggatca gggtaatcaa 3180
agagagggtg ggtgtgtagg ctgtttccag acacgctgga g 3221

<210> SEQ ID NO 4
<211> LENGTH: 11793
<212> TYPE: DNA
<213> ORGANISM: Homo sapiens

<400> SEQUENCE: 4
ggtacctcct ccagccttgg ccacagtgtc atccttgggc cccctaggtt tcagcctctt 60
gagtttgcac ttgcaggttt ggctgttgct ctcaaagcag gactattgca tcaacatggc 120
aggtgcagag gtcttcccgc ctcaatcgtc acccactgat ttctctgcca tggccttgaa 180
ctcaggcgac caatccagtt ggaacctccc cacactctcc gtggctaata attttggact 240
cagaagaaaa agcctcaatt tctctcctct caggaggtct cttggtcctt gagcaaatgt 300
atccatttct tctcctatct ccagtctttg ggccccccaaa ggtttttttc tccctttctc 360
caggacaatg agtgcctatt tacaagtgcc tgtttctact tgaataaggt ttctataaac 420
taagaagtgt tccttaggga cacaagtaac tggcactcct gttggaaaat gctaagatct 480
aggtcacgcg cacttccccc aacagacaca tacacacatt cacacacaca cacacacaca 540
cacacacaca cacacacaca cacacataca gcttgtctgc actctagcac tggcactgac 600
gctaacgcta taatcctggg caactttatt tccccatctt acattaagca gtggtgcagg 660
gattttcaac tctgggatct ctatcacacc tcccagctct gattgcttcc taatttacat 720
atttattgag catctgatgc taggtcctca tgctggtgat gcaggagtaa actagacaga 780
caaaagtccg tgccccacat tgtctgacac ctacacacct gctgttcgga ctccattaca 840
aacagctcca aggggaacag tgcacttgta aagtttctct cattaccatg gccacatccg 900
tgagcaataa ataagttgca tagttgaatt atttgataat gctttgtttt taactccctg 960
cacttaagtc agagatgtgt gtgctttgga aaactatttc tcctgactca ttagacaaat 1020
actatttgca tttttattca gcttccttcc tcagactcta atttacagta aaggcaagag 1080
gatttttgaa tggagccagt gctttgcaat gtggggctcc accagctagc cgactgaaat 1140
cattaataaa gaagcctttt taagtggctg aagtttcccc tttttggcat gcaacatttt 1200
gcaaccaagc ggaagaaaca tcatccgcaa agaagaatcc atgtggcccc tgaaaatcac 1260
tctctctgct acaggctccc cactccccag tgctcccctt agccctgcca ctatctctcc 1320
tccagatgga aaaagtgagg aactcaggga accaaaagtc ttgcttcttt actaatttcc 1380
ctgtctgaca ttaaatcatc ctacagttca gatatctggg ggaagtgact agagattctt 1440
gaactgttaa taattaattt aaatgatatt tgttaagaac ctacgacatg gaagatactg 1500
taccaggtgc tggggtccag catgggcaaa ggcctcaagg tggaatggag ctatggtgtg 1560
ttctggaagc agagagtggg gctgagggtg acatgaggtg aggagacagg agagggcctg 1620
gcagggtggg accttctggt gagagctggc tgctgtgtga ggagctgagg ccctggcttg 1680
attctggggt tacttctttg accttcagct ttttgtcatg ggcagacaga atggggatga 1740
aaaaaagctt aggaaatgga aacctcccta tgcattatat aataaaaatg gccaacacat 1800

-continued

```
tttcatagca agaaatcaca gcagaagctt gtactgggca tcaggactgt aggcatccaa   1860

tgcccagaaa ctggcatgtg ccctgggaca tcccctgaga aggcatgcca cgagccctca   1920

gactgacaca gctctttaca agttgcttac agagcactct tggtttatta attcatacaa   1980

gtctcatgac aatgtcagaa gcagctgtct tactaatccc ctttgacaga agaggcccag   2040

agaggtcaag ggacttgctc aaggccacac agctagaaag aggcagagcc aggcctttgg   2100

ccctggtgtt ctgacaccac ctggggctcc ttctgttatt ccatgctacc tcttctttct   2160

cttccgtatt cccttctcgt tcccttcctt cttgtgtctt gcttcttatc tgcctgtact   2220

tattcctgtt ggtgcctccc agctcagcca gcatagctct gtcttcaaat accccatgct   2280

tcattctggg gtcccataca cagtctgaca atcatctgag gggctgtgg gaggacatag    2340

aaaaaataca gctttacata gaaaaaaatg caaattgtag ccaggcgcag tggctcatgc   2400

ctgtaacccc agcactttgg gaggccgagg caggtggatc acctgaggtc aggagtctga   2460

gaccagcctg gccaatgtag taaaactcct tctctactaa aaatataaaa attagccagg   2520

cgtgatgtca tgtgcctgta gtcccagcta ctcgggaggc tgaggcagga gaacctcttg   2580

aatccaggag gcgcaggttg cagtgagcag agatagtgcc actgcactcc agcctgggtg   2640

acagagtgag actctgtctc aaaaaaataa aataaaataa aaaatgcaga ctgtgattca   2700

gcaggtctgg gttgaagccc agaactctct gataaattca atggcactta actacttgga   2760

ggtcatggat gcctttgcta atctaataga agctactgac cctctctcca gaaaaatgca   2820

caaaaacata aatgtggaag acaactcctg atggatctgg gagcctatcc aagggccaca   2880

gacaagagtc ctggtctgga caaaatgagc tgctcagtat tttcccacct ggccagcatt   2940

tcctatccaa agacaaatgt taaagttgtt ctagcagagc catgcaccag cagcagtatc   3000

atcacctggg aaccggttag caatgcagaa ccgcaggccc accccaaacc tacagtcaga   3060

atctctactt tagcaagatc ctaaggagat gggtaagcac attacaattt gcaacctttg   3120

taagtttgcc caaaatgtga cccctccttc acccaccgat cgccaaggtt caaaaatctg   3180

cccaaccctt gagcccatct taaatgtacc atcacgagcc ttccctgggc cctcagctg    3240

ggactctcac cgctctgtat ctttctggtt aatgcaatta ttctgttccc ttagatgacc   3300

ccagcacagg tgctaaagga gtcaacaaaa ggctattgtc aaaaaagtgt ttctgtctcc   3360

actccatctg atctctgttt ccctaagacc tgcccatccc cctctcccag ttcggcacct   3420

tgaccccctc atcacactgc tcaggccacc ttgtacaatg caagccccaa atgaggaaag   3480

cattttctcc cccaatgtgt aacacgaaag tgctgtagag tggctcacgc tgcctttagc   3540

ctaagaattt atttaactct tacccccaac ccacatcagt ctcctccctc tagggctcag   3600

gtgctaatct gtgagggctg gctcagaaga caatctaaag aacaagcctc ttgcttcctc   3660

aggcatcact actcctcacc accatcaccc ccacccacca actcaggcca ctactctttc   3720

tgttctcata tgctatgccc atcgccaccc ctattcccat gctcaggagt attcttggct   3780

actgcatgca attagacctg gggcagatcc aatccagaaa gcaagaaatc ttagatgctg   3840

gaagcttggg gtaagtactg atcagattta ttcctaaatt cagtcctact ttccatggat   3900

tcttacttta gcatctcttc tgaaaaggaa gcatcatgtc taattcactt ctccctccct   3960

gtgcagtcct ctacctggtg ctctgcacag ggtatgtgct aattgtatga atgttataat   4020

aaagagatag tgcagtagat gacaaagggc actacattga gagcccagaa ataagcaaac   4080

cagcacaaat gtagccattc gtcttctatc tcaccttgag cctgtcacta acctgttcat   4140

ggcctcagtc tccccatcag agaaacaggt agatggtctc taaggtctcg ttcattttct   4200
```

-continued

```
gacattctgt gaaaaattaa ggaaagattt tcatccttga caggaaaggg attgcagagt   4260
agcggccctg ggaaaatggg ctctattcta cctggagcta gcctggagga gaggccttga   4320
gtgggggttg tctagaaagg acatggtgag tgcagagcta cggtgcatct ctcttgaagg   4380
ctgagtgaag ggagcaccag caagggagcc tgcactaggt ggggagggac aagtgaaccg   4440
cagaagttgg tgggagccca ggcagtggct tcagatcttt ccagagagct cacttttact   4500
tcctcttttt ttcacccctg acactgagtg ggagtctgca gcgatgacca aggttcatgc   4560
agaggatctt agtggtgggg tcagaccccg ggaggaatga agaaagcatt attcaccaag   4620
aggagctttt ccattcttta tctatgagtt gatagagagg aggccccggg gtaactgagg   4680
attctggaca gcatcagagc attgaccctc attttcccca tagcccctct gggggccttt   4740
cccttgtgtg tccccaagcg agagtccaac caaggtttgt gccagagcct aacccaggct   4800
tgtgccgaga tgttcccagc acagccccat gtgagagctc cctggctccg ggcccagtat   4860
ctggaatgca ggctccagcc aaatgcattc tcttctacgg gatctgggaa cttccaaagc   4920
tgcctcctca gagtgggaat ttccactcac ttctctcacg ccagcactga cctcccagcg   4980
ggggagggca tcttttcttg acagagcaga agtgggaggc agacagctgt cactttccag   5040
aagactttct tttctgattc atacccttca ccttccctgt gtttactgtc tgatatatgc   5100
aaaggccaag tcactttcca gagatgacaa ctccttcctg aagtagagac atgcttccaa   5160
cactcagaag cctatgtgaa cactcagcca gcaaagctgg gaagtttttc tctgtgacca   5220
tgggctaatt ggtctccttc tctggattgt ggctttatca gataaaaaca agtggtcatg   5280
ccacaggatg tctataagcc cattgattct gggattctat gagtgatgct gatatgacta   5340
agccaggaga gacttattta aagatctcag catctttcag cttgttaacc tagagaaaac   5400
ccgaagcatg actggattat aaagggaaat tgaatgcggt ccaccaagtt catggtaaag   5460
gatgcactaa cagattagag agaggtttcc cctgatatga ggaaaacttc ttggaagatg   5520
aggtgagatg gcctaggaag aaattcctac acaaagttgc acagtctcta gtcctggaaa   5580
cattttattc attggataag aatggattga ggcatgagca gaggactgag acaaacacag   5640
agaagtttca acactggttg gggagaaaag gagtaactag tgagattcag gcagaacaag   5700
aataaggctc ctcaagaggc acaagcaaag cagggctcga gttgatttgt tctctcttca   5760
tcctgctttt tgtaattcca ccagagtctg aaatggccac tccatagagt ctctgctctg   5820
ggattctcca ggaaaccaat atccatcatg agacatcaag tctagtccca ggaagaagag   5880
attctggaat ggaaacatcc tgggtgggag tctcagcaca tctactattc tgtctgagtt   5940
actggacaaa taacttcagt tttaacctaa cgaaagctgg gttggttgga ggactgggca   6000
ggcagcgctg gaaagtatgt cagcaccata cctgactccc tgaatgcact caacaatgcc   6060
attactgacc acttactaga aataaaacag tcatttgttg aatacaaccc gtttcttttt   6120
acaagtgtag tgaaaagtgt tttctttcaa gaaaccccat gcatttatag acattgcctc   6180
agtgaccctt tatgaaagaa gtcactagtc tttgtatgcc cattgggcaa gggcaccgca   6240
aggctcagaa ggaggaggca gtgggctagg agaatcgaga gatcagaatt ttaaactcag   6300
cccagccatt aacatgcctc aagtactcct atcatatttg taagagacaa cagttcactg   6360
aaatgaattc taaggtcttt gggtttttat cagtgtgctt ctgtagtttc tgaggaaatc   6420
taaggcacaa ctgaggaatg aagtcaggct ttccaattcc cgaaatactc ctccactgct   6480
tactcatgtc ccatggaaat taagaaggaa gccaggagaa tagctgccat aaccagggat   6540
gaacttcttg tccactgctg cctgctatgc tagcaacagc ctcctaactc ataatgactt   6600
```

-continued

```
agccatgagg aatgtttcta gattctcctt tagctgtctg cccatttgga agatgctgag   6660
gacagagaga ggacccaagc aggcaactag ttggaggact tgtacacgtt tccttccagc   6720
agtatgtcag agaggtggca gcccactggg gacagggctg cctgggttct gtgctcgagg   6780
ggaccttgag caggctattt aacccttctg tgcctcagtt gcctgatcta taacatgaaa   6840
attagcaatc cctactagat aaagttgggg aatttacaga gttaatattt gtaaaggtct   6900
gagaatattc ctggcagagt aagcactctg tgagtatgac actggcattt cttctgcagc   6960
actacatgct gtctatgcct ttgtccaagt ctgaaaccct agaactctta gaattcagtt   7020
caatgtttac acaatcctac agttctgcta ggcttctatg atgctactat tctgcatttg   7080
aatgagcaaa tggatttaat gcattgtcag ggagccggcc aaagcttgag agctccttcc   7140
tggctgggag gccccttgga atgtggcctg aaggtaagct ggcagcgagc ctgacatgct   7200
ttcatctagt ttcctcgctt ccttcctttt ctgcagtttt cgcttcacag aaagcagaat   7260
ccttaaaaat aaccctctta gttcacatct gtggtcagtc tgggcttaat ggcaccccat   7320
cctccccatt tgctcatttg gtctcagcag tgaatggaaa aagtgtctcg tcctgacccc   7380
ctgcttccct ttcctacttc ctggaaatcc acaggatgct gcatttgctc agcagattta   7440
acagcccact tatcactcat ggaagatccc tcctcctgct tgactccgcc ctctctccct   7500
ctgcccgctt tcaataagag gcagagacag cagccagagg aaccgagagg ctgagactaa   7560
cccagaaaca tccaattctc aaactgaagc tcgcactctc gcctccagca tgaaagtctc   7620
tgccgccctt ctgtgcctgc tgctcatagc agccaccttc attccccaag ggctcgctca   7680
gccaggtaag gcccccctctt cttctccttg aaccacattg tcttctctct gagttatcat   7740
ggaccatcca agcagacgtg gtacccacag tcttgcttta acgctacttt tccaagataa   7800
ggtgactcag aaaaggacaa ggggtgagcc caaccacaca gctgctgctc ggcagagcct   7860
gaactagaat tccagctgtg aaccccaaat ccagctcctt ccaggattcc agctctggga   7920
acacactcag cgcagttact cccccagctg cttccagcag agtttgggga tcagggtaat   7980
caaagagagg gtgggtgtgt aggctgtttc cagacacgct ggagacccag aatctggtct   8040
gtgcttcatt caccttagct tccagagacg gtgactctgc agaggtaatg agtatcaggg   8100
aaactcatga ccaggcatag cctattcaga gtctaaaagg aggctcatag tggggctccc   8160
cagctgatct tccctggtgc tgatcatctg gattattggt ccgtcttaat gacacttgta   8220
ggcattatct agctttaact ctgtccatta tcaatgttat atacccattt tacagcatag   8280
gaaactgagt cattgggtca aagatcacat tctagctctg aggtataggc agaagcactg   8340
ggatttaatg agctctttct cttctcctgc ctgccttttg ctttttcctc atgactcttt   8400
tctgctctta agatcagaat aatccagttc atcctaaaat gctttttctt tgtggtttat   8460
tttccagatg caatcaatgc cccagtcacc tgctgctata acttcaccaa taggaagatc   8520
tcagtgcaga ggctcgcgag ctatagaaga atcaccagca gcaagtgtcc caaagaagct   8580
gtgatgtgag ttcagcacac caaccttccc tggcctgaag ttcttccttg tggagcaagg   8640
gacaagcctc ataaacctag agtcagagag tgcactattt aacttaatgt acaaaggttc   8700
ccaatgggaa aactgaggca ccaagggaaa aagtgaaccc caacatcact ctccacctgg   8760
gtgcctattc agaacacccc aatttcttta gcttgaagtc aggatggctc cacctggaca   8820
cctataggag cagtttgccc tgggttccct ccttccacct gcgttcctcc tctagctccc   8880
atggcagccc tttggtgcag aatgggctgc acttctagac caaaactgca aaggaacttc   8940
atctaactct gtcctccctc cccacagctt caagaccatt gtggccaagg agatctgtgc   9000
```

```
tgaccccaag cagaagtggg ttcaggattc catggaccac ctggacaagc aaacccaaac   9060
tccgaagact tgaacactca ctccacaacc caagaatctg cagctaactt attttcccct   9120
agctttcccc agacaccttg ttttatttta ttataatgaa ttttgtttgt tgatgtgaaa   9180
cattatgcct taagtaatgt taattcttat ttaagttatt gatgttttaa gtttatcttt   9240
catggtacta gtgtttttta gatacagaga cttggggaaa ttgcttttcc tcttgaacca   9300
cagttctacc cctgggatgt tttgagggtc tttgcaagaa tcattaatac aaagaatttt   9360
ttttaacatt ccaatgcatt gctaaaatat tattgtggaa atgaatattt tgtaactatt   9420
acaccaaata aatatatttt tgtacaaaac ctgacttcca gtgttttctt gaaggaaatt   9480
acaaagctga gagtatgagc ttggtggtga caaaggaaca tgatttcaga gggtggggct   9540
tacattttga aggaatggga aagtggattg gccccggtct tctccactgg gtggtctcct   9600
ctgagtctcc gtagaagaat ctttatggca ggccagttag gcattaaagc accacccttc   9660
cagtcttcaa cataagcagc ccagagtcca atgaccctgg tcacccattt agcaagagcc   9720
caacccccat tccttttctc acagaccctg acccctgcat gcaattcttc ccttaacata   9780
ttgcaactgc cccctaactg ggctacccac cccccaatct gtacctctcc aattaatacc   9840
ccaacctgga gtaatacaga cactgccagt attaggaaat aaggaaagag ttaatcacca   9900
tagataagat gattagattg aagtttcata gagatgatga gacctgaact tattatttat   9960
gaatgaagaa ggcttttcta ggaaaattat aggatcatta agaaaggaga aggaagagtg  10020
ggagcaaata cctggaggta gaaatggtga tgatgtgtac atcaagcagg gagaaaacca  10080
atgaaccaga tgcgaattcg ggcccacacc aatgtcaagg gatgacaatt agaaaggaag  10140
gttgagtcaa gggatttgaa tgttagggtg aaaagttact actcaactct gtaggttaaa  10200
aggaaacgtt gagaatcttc agtccaatga ggagggatgt gccatgttta gagattcaga  10260
gataagtttc aggaaatgta acttatagat tttatacata cacagagaaa tacggactag  10320
tgagaagcta ttgccatggt ccaagcaaga gatgatgaag gcctaaatat ggagccaaag  10380
aggcagcaat gaagaatgag ccatgcaggg tgaaatgctg catgttgtaa atggaggaga  10440
aagacctgtg acttcagata tgaaaacctc atcttcaacc cacattttaa gggggcagct  10500
tccctgaaac cagaatgtgt ttccctccat tactataccc ccatcccaat ctcaggcacc  10560
tggaatcatc catttaaaca gatgagcctt ctattcctaa atagccacct gaagtgtgta  10620
ttcctttgca tgatatttgt cccacctaaa gcattcgacc tgcctgggca cccacaccac  10680
gccaacactc aggaaagcag atgtcttgct ctgttgaata aactgcatgg ttcttaactt  10740
cccagtctgg tggggaaatg accactgtgt caacctagag caggcagtgc ttttggcagc  10800
atgaggtgct ggggacaact ttgactggca agaagcacac tcaggttctc accccgcatc  10860
cagcgctgac tcgctttgtc agtcaagaca ggtcagatat tctgagccta catcgatcat  10920
acaggtatga taatgtgtta caaataggaa cccagaggaa aggttccctt tcggatctgg  10980
gagcacatct gttggaaaac ttccatttct actaactgga gttgcagagg gagagaaggg  11040
attctgcttc tacattcctg agccagtcca gggtccctga atcagactac cgaatccctt  11100
caaagctcca agtaccctga tatatcagtc agcagacaat ttattgacag ctatttagaa  11160
aactcactga ccctcactcc aggtcaagca gcgtcccctg cctctcctct accccctacat  11220
tccctggcct tgatcaccag tcaggagtga aatctcaaat tgcagtagat gccaagaggc  11280
aaaaagagaa tagaatgcaa acaaatgaga cctcatcata tggcttccga gcagcaacct  11340
tttgacgcca ggcagatttg aggcagacag tctgggagga gaggaggcag agaaaggggg  11400
```

-continued gatccacatg ctcaaacccc aaattaatct gcttacattc cccttgcagg ccacatctct 11460
tcattttcag gaagtcttga ctccatactg ttttccaccc aagcatggaa ttcctttcat 11520
gatgaaactg aacacagggc attggcagtg gtgagactct gttttagaag aaagtgccaa 11580
gtgcaatgca ttcatttcct gttgctgcca acaatcagtt ccaggaaatc taggcttttt 11640
atgtcatgct caaaattctt ccagcctatg ctcattattc aaatccaaag ccacatccac 11700
atctgtaggt gttagttaca gaagcaccat atttccaggt accaaaatct gtattagttt 11760
cttattgtta ctgtaacaaa ttcccataag ctt 11793

<210> SEQ ID NO 5
<211> LENGTH: 2273
<212> TYPE: DNA
<213> ORGANISM: Homo sapiens

<400> SEQUENCE: 5
caggactgcc tgagacaagc cacaagctga acagagaaag tggattgaac aaggacgcat 60
ttccccagta catccacaac atgctgtcca catctcgttc tcggtttatc agaaatacca 120
acgagagcgg tgaagaagtc accacctttt ttgattatga ttacggtgct ccctgtcata 180
aatttgacgt gaagcaaatt ggggcccaac tcctgcctcc gctctactcg ctggtgttca 240
tctttggttt tgtgggcaac atgctggtcg tcctcatctt aataaactgc aaaaagctga 300
agtgcttgac tgacatttac ctgctcaacc tggccatctc tgatctgctt tttcttatta 360
ctctcccatt gtgggctcac tctgctgcaa atgagtgggt ctttgggaat gcaatgtgca 420
aattattcac agggctgtat cacatcggtt attttggcgg aatcttcttc atcatcctcc 480
tgacaatcga tagatacctg gctattgtcc atgctgtgtt tgctttaaaa gccaggacgg 540
tcacctttgg ggtggtgaca agtgtgatca cctggttggt ggctgtgttt gcttctgtcc 600
caggaatcat ctttactaaa tgccagaaag aagattctgt ttatgtctgt ggcccttatt 660
ttccacgagg atggaataat ttccacacaa taatgaggaa cattttgggg ctggtcctgc 720
cgctgctcat catggtcatc tgctactcgg gaatcctgaa aaccctgctt cggtgtcgaa 780
acgagaagaa gaggcatagg gcagtgagag tcatcttcac catcatgatt gtttactttc 840
tcttctggac tccctataac attgtcattc tcctgaacac cttccaggaa ttcttcggcc 900
tgagtaactg tgaaagcacc agtcaactgg accaagccac gcaggtgaca gagactcttg 960
ggatgactca ctgctgcatc aatcccatca tctatgcctt cgttggggag aagttcagaa 1020
gcctttttca catagctctt ggctgtagga ttgccccact ccaaaaacca gtgtgtggag 1080
gtccaggagt gagaccagga aagaatgtga aagtgactac acaaggactc ctcgatggtc 1140
gtggaaaagg aaagtcaatt ggcagagccc ctgaagccag tcttcaggac aaagaaggag 1200
cctagagaca gaaatgacag atctctgctt tggaaatcac acgtctggct tcacagatgt 1260
gtgattcaca gtgtgaatct tggtgtctac gttaccaggc aggaaggctg agaggagaga 1320
gactccagct gggttggaaa acagtatttt ccaaactacc ttccagttcc tcatttttga 1380
atacaggcat agagttcaga cttttttttaa atagtaaaaa taaaattaaa gctgaaaact 1440
gcaacttgta aatgtggtaa agagttagtt tgagttgcta tcatgtcaaa cgtgaaaatg 1500
ctgtattagt cacagagata attctagctt tgagcttaag aattttgagc aggtggtatg 1560
tttgggagac tgctgagtca acccaatagt tgttgattgg caggagttgg aagtgtgtga 1620
tctgtgggca cattagccta tgtgcatgca gcatctaagt aatgatgtcg tttgaatcac 1680
agtatacgct ccatcgctgt catctcagct ggatctccat tctctcaggc ttgctgccaa 1740

-continued aagccttttg tgttttgttt tgtatcatta tgaagtcatg cgtttaatca cattcgagtg 1800
tttcagtgct tcgcagatgt ccttgatgct catattgttc cctaatttgc cagtgggaac 1860
tcctaaatca aattggcttc taatcaaagc ttttaaaccc tattggtaaa gaatggaagg 1920
tggagaagct ccctgaagta agcaaagact ttcctcttag tcgagccaag ttaagaatgt 1980
tcttatgttg cccagtgtgt ttctgatctg atgcaagcaa gaaacactgg gcttctagaa 2040
ccaggcaact tgggaactag actcccaagc tggactatgg ctctactttc aggccacatg 2100
gctaaagaag gtttcagaaa gaagtgggga cagagcagaa ctttcacctt catatatttg 2160
tatgatccta atgaatgcat aaaatgttaa gttgatggtg atgaaatgta aatactgttt 2220
ttaacaacta tgatttggaa aataaatcaa tgctataact atgttgataa aag 2273

<210> SEQ ID NO 6
<211> LENGTH: 1979
<212> TYPE: DNA
<213> ORGANISM: Homo sapiens

<400> SEQUENCE: 6
caggactgcc tgagacaagc cacaagctga acagagaaag tggattgaac aaggacgcat 60
ttccccagta catccacaac atgctgtcca catctcgttc tcggtttatc agaaatacca 120
acgagagcgg tgaagaagtc accacctttt ttgattatga ttacggtgct ccctgtcata 180
aatttgacgt gaagcaaatt ggggcccaac tcctgcctcc gctctactcg ctggtgttca 240
tctttggttt tgtgggcaac atgctggtcg tcctcatctt aataaactgc aaaaagctga 300
agtgcttgac tgacatttac ctgctcaacc tggccatctc tgatctgctt tttcttatta 360
ctctcccatt gtgggctcac tctgctgcaa atgagtgggt ctttgggaat gcaatgtgca 420
aattattcac agggctgtat cacatcggtt attttggcgg aatcttcttc atcatcctcc 480
tgacaatcga tagatacctg gctattgtcc atgctgtgtt tgctttaaaa gccaggacgg 540
tcacctttgg ggtggtgaca agtgtgatca cctggttggt ggctgtgttt gcttctgtcc 600
caggaatcat ctttactaaa tgccagaaag aagattctgt ttatgtctgt ggcccttatt 660
ttccacgagg atggaataat ttccacacaa taatgaggaa cattttgggg ctggtcctgc 720
cgctgctcat catggtcatc tgctactcgg gaatcctgaa aaccctgctt cggtgtcgaa 780
acgagaagaa gaggcatagg gcagtgagag tcatcttcac catcatgatt gtttactttc 840
tcttctggac tccctataac attgtcattc tcctgaacac cttccaggaa ttcttcggcc 900
tgagtaactg tgaaagcacc agtcaactgg accaagccac gcaggtgaca gagactcttg 960
ggatgactca ctgctgcatc aatcccatca tctatgcctt cgttggggag aagttcagaa 1020
ggtatctctc ggtgttcttc cgaaagcaca tcaccaagcg cttctgcaaa caatgtccag 1080
ttttctacag ggagacagtg gatggagtga cttcaacaaa cacgccttcc actggggagc 1140
aggaagtctc ggctggttta taaaacgagg agcagtttga ttgttgttta taaagggaga 1200
taacaatctg tatataacaa caaacttcaa gggtttgttg aacaatagaa acctgtaaag 1260
caggtgccca ggaacctcag ggctgtgtgt actaatacag actatgtcac ccaatgcata 1320
tccaacatgt gctcagggaa taatccagaa aaactgtggg tagagacttt gactctccag 1380
aaagctcatc tcagctcctg aaaaatgcct cattaccttg tgctaatcct ctttttctag 1440
tcttcataat ttcttcactc aatctctgat tctgtcaatg tcttgaaatc aagggccagc 1500
tggaggtgaa gaagagaatg tgacaggcac agatgaatgg gagtgaggga tagtggggtc 1560
agggctgaga ggagaaggag ggagacatga gcatggctga gcctggacaa agacaaaggt 1620

-continued gagcaaaggg ctcacgcatt cagccaggag atgatactgg tccttagccc catctgccac 1680
gtgtatttaa ccttgaaggg ttcaccaggt cagggagagt ttgggaactg caataacctg 1740
ggagttttgg tggagtccga tgattctctt ttgcataagt gcatgacata tttttgcttt 1800
attacagttt atctatggca cccatgcacc ttacatttga aatctatgaa atatcatgct 1860
ccattgttca gatgcttctt aggccacatc cccctgtcta aaaattcaga aaatttttgt 1920
ttataaaaga tgcattatct atgatatgct aatatatgta tatgcaatat aaaatttag 1979

<210> SEQ ID NO 7
<211> LENGTH: 10073
<212> TYPE: DNA
<213> ORGANISM: Homo sapiens

<400> SEQUENCE: 7
gtttatgaaa ttacagggct ggagacaaag atcacaatgt gaagacaaaa ttggagagcg 60
gtcctaatca gccagagcaa aatttctggc tcttgctctt ccccatcctg ggttgaatca 120
taggaacagg tggcaagatg ccagggtcag gagattccag aagtggcagc aagctcagtg 180
ttaccaggtc agggatgacc tgtcttatta ttgaaatctc agagatatgc tccaattccg 240
gcccagagac acattgagag acaactgggg aacttgctat gttcctgaac aggcaatgag 300
ctgtcttcca agaaaaaacc tgagaccctt caagtctcag gtcttactta gcacatatac 360
caggtcttac acaggacaca tggttacaac tgactgaaat ctgggctggg tgtaggagct 420
cacacctgta atcccagccc ttcaggaggc tgaggcaggc agattgcctg agcccaggag 480
ttcgagacca gcccgggcaa catgacaaaa ccccatctct acaaaaaata gtcaggcatg 540
gtggcatgca cctgtagtct cagctacttg ggaggctgag atgagaggat tgcttgaggt 600
tgagactgca gtgaagcatg atcatgccac cgcactccag cctaggcaac agagcaagat 660
cttgtcgcaa aagaaagcaa aaacacaaca taacacaaca acaacaacaa caacaacaac 720
agcaaaaaag ccaacttctt gaaatctgga aaggacacct ggactgccct gagcatttga 780
ttgttgttgg ctctagcagt ggatgcatcc ttcaacctct ggcactctgc agggctcaga 840
ctgttctgtt ctgtttgtta cctgtggagt gcctgccaga ccctgctcta gctgctttag 900
gtccatttac cctcatagac ccccagtctt gttattcata tttcatattt gggaaatgga 960
aacttagaaa cttgccaagt ccacagcatg agatcctgcc tccggtgtct gctggattcc 1020
agaaagtgcc aggggccaac ttagatgaca ccatgttctc tgcacaatct taggaatgct 1080
cctagtctga tgtccccatt gcaaaattta cattatcttt taacaaaacg tctttccaag 1140
gaggggcatt taaaataact gaggttcttc ttgctaagga agttcctgac acaagagata 1200
atttagcatt tccttttcat taaaaagttt gaaatcctgt aatttgtgat aatgtggatg 1260
aacctagagg atgttaagtg aaataagcca cacacagata gacaaatacc acgtgatctc 1320
actcttatgt ggaatttttt tttaaataag ttgcttagcc gggcatgatg gcacacacct 1380
gtaatcctag ctactcagga ggctgaggtg ggaggatggc ttgaactcag aaggtggagg 1440
ttgcagtgag ctgagactgt gccagtgcac tccggtctgg gtgacagaat gaaacccaat 1500
ttaaaaaaaa aaaaaaagtt gctatcttag aaaaagacag tagagcagtg gttaccagag 1560
actggggagg aaagagagga ggtgagaatg ggcagcagtt gatcaacggg tacaaagtta 1620
ccatgagata ggagaaacaa gtgctggtgc tctgctccaa gtagggtgac ggtagttaat 1680
aatgaattct gtatatataa atagctagaa gagagggttt tcaatatcat tattatttca 1740
aaagaaatga taaatgtttc agaggatgga tatgtaatta ccctgatttg atcattgcac 1800
aatgtataca tgtagcaaaa catcacattg tgtcccataa atatatacaa ttattatgtg 1860
aattaaataa aaaaaaattt taaagtctta tctaaatgaa atttctaacc agattctgaa 1920
tccatgatac cactgaaacc agcacacatg atcgcagtaa aacctcatta tacttcctcc 1980
actatcacca ataccctttta ttctctggaa catgaaacat tctgttgtgc tcatatcatg 2040
caaattatca ctagtaggag agcagagagt ggaaatgttc caggtataaa gacccacaag 2100
ataaagaagc tcagagtcgt tagaaacagg agcagatgta cagggtttgc ctgactcaca 2160
ctcaaggttg cataagcaag atttcaaaat taatcctatt ctggagacct caacccaatg 2220
tacaatgttc ctgactggaa aagaagaact atatttttct gattttttt tttcaaatct 2280
ttaccattag ttgccctgta tctccgcctt cactttctgc aggaaacttt atttcctact 2340
tctgcatacc aagtttctac ctctagatct gtttggttca gttgctgaga agcctgacat 2400
accaggactg cctgagacaa gccacaagct ggtgagttgt aggcattttt tccattactt 2460
tctgattcat aggctcaacg cacctcaaag ctggaaatgc cgggtctggg tacaccctgg 2520
ggaactgcaa agcctgcaca cttgggggga atgatcaaga tgagaggcag gggtggggat 2580
ggcatgtgca ccaggagatg ttagagaaac cctgaggaag agcagcgtgc agcaggtgat 2640
gggggagagt gggcagcaag cgaggccagg acagccactc tgctcagtca ccagtccaca 2700
cacccagggg ctcactctgc ccctctgagc acccaaggac gttaaagagc tggaactgtt 2760
agtctaaata taggaccatc caagctctga accaaaatgt gtcccttgcc tcaactcagg 2820
agatccacag aggcagaagt aaggaattta ttttctgaaa gatagatttc tatcagttct 2880
gggtgacatg ttctgacact tgaaatgaca cctaggacag cacatttcag gcatcttgct 2940
cattgttcac tgtagtagaa gctacatgct agccagttgt aaaaatgaaa ttaagtaatg 3000
tgtgcacagc atttaacata gcatctgagc ttcaggagca ctcaattaat gaccacagtt 3060
gtgattcttt aggcagatgc atttttttcc aactttgatc agaggtctta tttagcttct 3120
ccagatttca agaatctggc tcagtgatat gaaatacaag acttgtgaaa agtgtcaatt 3180
gcaagagaaa tggaaggata aagtatacag gtgggtggaa aagaaattca cagtcactgc 3240
cagaaaaaaa attcttgaga atcaagtcct gatgatgtta gggcttatag ttcttattat 3300
aaagagtttt atgtactcat tcagtgaaca tttattggtg cctcctttag ccaggtacta 3360
tcataagagc tgaaaataga agcataatcc agtccttgat cttgaggaac atgctgtgtg 3420
tagcagataa cataataagt gcttatctag atgcatgcag tgttatgtga taagagtaat 3480
atgacagagg atacagatta ggcttcacag agaaggggga tttgagcagg aggtattgaa 3540
gggtgaatag aagctcacca atcattttgg gcagaggggc aaggacctgc aaaaccactg 3600
aagcatgaag gaaatggtga gtttagggaa aatgaagaga agatggctgt gactgaagca 3660
caggatttgg gattggagaa gggactggag gtgaggctga aaagaggcaa actcagaaaa 3720
gatgttgtgc tgggcagtct ggacattatc tttgaagccc accacatata agtcataggg 3780
ctactggagg ttttaagcta agagtgacta ttcaatttca acttaagaga agataggttg 3840
agagggaaca tggcttgaga tgagccatga gcaaaggaaa gactacaaca aagccaggag 3900
tgaggagtgt gtgaagcaag aaagtgacag ttgaaagcag tgcagagggg atgaatctga 3960
gaggcatcta tgaggtggaa ctcaaatgac atgataataa tacagggcat ttctctgtgt 4020
cagatgctgt cctaagtcct tactccattg atcttcacag caactcagca tagttaatat 4080
tttatgcata aagaaatcgg cacttgaagg agtaattggc cccagattac actgcctata 4140
aggattcaaa tccaggtttg tttggctcca aaaactggct cctaattttc agaaggagaa 4200
gcgacccagg gcaatgccca attttgcttc ttaggcaatg gaggaatcca caatcggaag 4260
gagttttcag cagtgcccca tttggggtgg gttgaatttg aggtccctgc atgatacca 4320 ctttgctcac ttcagtgcct aaaactgagt atggttcata gtaggtgttc aataagtgtt 4380
gatgcagtga atacatgcat ggggagatat gcatcaggca atgggaaatt caactctaag 4440
gcttagggga aagctggagc ttgaagacag agctttagaa aacagtagca tagaagggag 4500
taggaaccat gagtttagac aatacaattc aggaagaact ttgtagcaag gataaagagg 4560
caaaaaatta aagaggtgag agctaagtgt ggtgcctggg gaatcttaag gtgtgggcac 4620
ggggaggaga tgccagcaaa gaacatgaat aaaaagcggt agcacagccc ctcccatctg 4680
gaagccaaaa agaattgtaa atggaggaag ttagcagaag gatcaaatac ttgaagaggg 4740
tggaattgga ataaaaccag ggcatttgaa aaattgggtt gtcactgcaa tcttaacaag 4800
agaagttttg gcaggatgat ggaggcagaa agctgagaga atcatcagtt agaacgtttt 4860
tgacttcaga gaacagaaaa tgcagttcat aatggcttta aaacaggggc ttgtttttct 4920
cccagcaatt tgagaggcca aggcgggtgc atcaggaggt caagagaccg agaccatcct 4980
ggccaacatg gtgaatcccc atctctacta aaaatacaaa aattagcggg gcatggtggt 5040
gcacgcctat agtcccatct actcaggagg ctgaggcagg agaatcactt gaacccagga 5100
ggtggaggtt gcagtgagct gagatcatgg ccactgcact atagcctgga gacacagcga 5160
gactccgtct ccaaaaaaaa aaaaaaagaa ggcagaaggt gaatagttca agggtgggtt 5220
taggactcag tgataatagg attctgcctg gcttctcatg gttctctagg tcttccattc 5280
atggcaccat gccctcacta ggcatgctgc cagagcagga ggggcaggtg gagggttctc 5340
ttgtgtctgt cttatcaggg aagaagagct ttctcagaag cccccagcag actccctttt 5400
catattatgg tccagcaatg agtcacagac ctatgcacca cctgcaaagg agccagagaa 5460
aacaaacgcc cagcgctttt agcctgaaaa tgagaatctg gtttgctggg gaagataaag 5520
ggtgtcggaa aatggctgtt gggtaaatca ttgatgtctg ccactaggaa tgaaaggcaa 5580
atcaggaact ggcacacatg ctttcaggga gatggctgca agggagaggg caaagactgg 5640
gaagttgctt atgtggtgcc agactatttg gaagatcatg gattgcggtg tttgtgttgt 5700
gtggtcatca ttttgttctt tgtttacaga acagagaaag tggattgaac aaggacgcat 5760
ttccccagta catccacaac atgctgtcca catctcgttc tcggtttatc agaaatacca 5820
acgagagcgg tgaagaagtc accacctttt ttgattatga ttacggtgct ccctgtcata 5880
aatttgacgt gaagcaaatt ggggcccaac tcctgcctcc gctctactcg ctggtgttca 5940
tctttggttt tgtgggcaac atgctggtcg tcctcatctt aataaactgc aaaaagctga 6000
agtgcttgac tgacatttac ctgctcaacc tggccatctc tgatctgctt tttcttatta 6060
ctctcccatt gtgggctcac tctgctgcaa atgagtgggt ctttgggaat gcaatgtgca 6120
aattattcac agggctgtat cacatcggtt attttggcgg aatcttcttc atcatcctcc 6180
tgacaatcga tagatacctg gctattgtcc atgctgtgtt tgctttaaaa gccaggacgg 6240
tcacctttgg ggtggtgaca agtgtgatca cctggttggt ggctgtgttt gcttctgtcc 6300
caggaatcat ctttactaaa tgccagaaag aagattctgt ttatgtctgt ggcccttatt 6360
ttccacgagg atggaataat ttccacacaa taatgaggaa cattttgggg ctggtcctgc 6420
cgctgctcat catggtcatc tgctactcgg gaatcctgaa aaccctgctt cggtgtcgaa 6480
acgagaagaa gaggcatagg gcagtgagag tcatcttcac catcatgatt gtttactttc 6540
tcttctggac tccctataat attgtcattc tcctgaacac cttccaggaa ttcttcggcc 6600
tgagtaactg tgaaagcacc agtcaactgg accaagccac gcaggtgaca gagactcttg 6660
ggatgactca ctgctgcatc aatcccatca tctatgcctt cgttggggag aagttcagaa 6720
ggtatctctc ggtgttcttc cgaaagcaca tcaccaagcg cttctgcaaa caatgtccag 6780
ttttctacag ggagacagtg gatggagtga cttcaacaaa cacgccttcc actggggagc 6840
aggaagtctc ggctggttta taaaacgagg agcagtttga ttgttgttta taaagggaga 6900
taacaatctg tatataacaa caaacttcaa gggtttgttg aacaatagaa acctgtaaag 6960
caggtgccca ggaacctcag ggctgtgtgt actaatacag actatgtcac ccaatgcata 7020
tccaacatgt gctcagggaa taatccagaa aaactgtggg tagagacttt gactctccag 7080
aaagctcatc tcagctcctg aaaaatgcct cattaccttg tgctaatcct ctttttctag 7140
tcttcataat ttcttcactc aatctctgat tctgtcaatg tcttgaaatc aagggccagc 7200
tggaggtgaa gaagagaatg tgacaggcac agatgaatgg gagtgaggga tagtggggtc 7260
agggctgaga ggagaaggag ggagacatga gcatggctga gcctggacaa agacaaaggt 7320
gagcaaaggg ctcacgcatt cagccaggag atgatactgg tccttagccc catctgccac 7380
gtgtatttaa ccttgaaggg ttcaccaggt cagggagagt ttgggaactg caataacctg 7440
ggagttttgg tggagtccga tgattctctt ttgcataagt gcatgacata tttttgcttt 7500
attacagttt atctatggca cccatgcacc ttacatttga aatctatgaa atatcatgct 7560
ccattgttca gatgcttctt aggccacatc cccctgtcta aaaattcaga aaatttttgt 7620
ttataaaaga tgcattatct atgatatgct aatatatgta tatgcaatat atataggctc 7680
ttgcttgatc tctccaggag gtagtgatta tgagaagggg gtggagaatg atgagttcct 7740
tcaccaggag caaaggacgg ggatcgtgtg gaaccactgc agaactattt ccgaaatcaa 7800
ctaagtggag agagccagga aggctgcatc agaacccagt aaagcttctt gtctggatct 7860
gagctggttt gttttgtgct tgcttttccc tgccttgcca ctcccctcac tcttctcttt 7920
tccccacagc ctttttcaca tagctcttgg ctgtaggatt gccccactcc aaaaaccagt 7980
gtgtggaggt ccaggagtga gaccaggaaa gaatgtgaaa gtgactacac aaggactcct 8040
cgatggtcgt ggaaaaggaa agtcaattgg cagagcccct gaagccagtc ttcaggacaa 8100
agaaggagcc tagagacaga aatgacagat ctctgctttg gaaatcacac gtctggcttc 8160
acagatgtgt gattcacagt gtgaatcttg gtgtctacgt taccaggcag gaaggctgag 8220
aggagagaga ctccagctgg gttggaaaac agtattttcc aaactacctt ccagttcctc 8280
atttttgaat acaggcatag agttcagact ttttttaaat agtaaaaata aaattaaagc 8340
tgaaaactgc aacttgtaaa tgtggtaaag agttagtttg agttactatc atgtcaaacg 8400
tgaaaatgct gtattagtca cagagataat tctagctttg agcttaagaa ttttgagcag 8460
gtggtatgtt tgggagactg ctgagtcaac ccaatagttg ttgattggca ggagttggaa 8520
gtgtgtgatc tgtgggcaca ttagcctatg tgcatgcagc atctaagtaa tgatgtcgtt 8580
tgaatcacag tatacgctcc atcgctgtca tctcagctgg atctccattc tctcaggctt 8640
gctgccaaaa gccttttgtg ttttgttttg tatcattatg aagtcatgcg tttaatcaca 8700
ttcgagtgtt tcagtgcttc gcagatgtcc ttgatgctca tattgttccc tattttgcca 8760
gtgggaactc ctaaatcaag ttggcttcta atcaaagctt ttaaacccta ttggtaaaga 8820
atggaaggtg gagaagctcc ctgaagtaag caaagacttt cctcttagtc gagccaagtt 8880
aagaatgttc ttatgttgcc cagtgtgttt ctgatctgat gcaagcaaga aacactgggc 8940
ttctagaacc aggcaacttg ggaactagac tcccaagctg gactatggct ctactttcag 9000

```
gccacatggc taaagaaggt ttcagaaaga agtggggaca gagcagaact ttcaccttca   9060

tatatttgta tgatcctaat gaatgcataa aatgttaagt tgatggtgat gaaatgtaaa   9120

tactgttttt aacaactatg atttggaaaa taaatcaatg ctataactat gttgataaaa   9180

gatttaaaaa caactggctg tttttttaca ctgtggtgtg gaagattgtg ttgtgttcac   9240

aacttttcac ttcttcccct gtgtgattac acacacctgc ccttgtggtg tgacttgcag   9300

tgcgccctac aggccacaca accccatgcc ctccaccact ggctctgctg ctggaatgtg   9360

agcagaagtg acatctgcct catccaagca gagcctcttg ctcagccaca ggaaggccca   9420

ttccagatca cacccgtcag cccgtgcgcc ctggtgaatg agaagacaca gggagctgca   9480

gccacatata acatgagcaa gaagtctgtg tttgctgtga taagccactg agttttaggg   9540

gttgtttgtt aagaagcaca aaaaccgatt aagacatgtg gtatatagtg acttcatata   9600

tagaatctgg aaaactatcc atttattttc aatcatggaa ttcaatatga caagcatccc   9660

ggagggtcta cctatgccag actgggttgg aaacagaaag acagatgtta atgccagtgt   9720

cctttacacc tccaagtcca gggccagctg tggagtggga ggggtagaga aggtcctgtg   9780

cacagtcaca gtgcgctgtg cagagcagga acagaggcat ctgtgaaaag tgctgagagc   9840

ctggaggaca gagtgactaa tgcaatgaca gtcttgcatc ataggaataa cagccacagc   9900

aggattttat tgctgccaaa gaaactgcca tttaaaaatt gccagccatc cgggaggctg   9960

aggcaggaga atggcatgaa tccaggaggc ggagcttgca gtgagccgag atcgggccac  10020

tgcactccag cctgggcaac agagccagac tccatctcaa aaaaaaaaaa aaa         10073
```

<210> SEQ ID NO 8
<211> LENGTH: 2082
<212> TYPE: DNA
<213> ORGANISM: Homo sapiens

<400> SEQUENCE: 8

```
gcacacctgt aatcccagcc cttcaggagg ctgaggcagg cagattgcct gagcccagga     60

gttcgagacc agcccgggca acatgacaaa accccatctc tacaaaaaat agtcaggcat    120

ggtggcatgc acctgtagtc tcagctactt gggaggctga gatgagagga ttgcttgagg    180

ttgagactgc actgaagcat gatcatgcca ccgcactcca gcctaggcaa cagagcaaga    240

tcttgtcgca aaagaaagca aaaatacaac ataacacaac aacaacaaca acaacaacaa    300

cagcaaaaaa gccaacttct tgaaatctgg aaaggacacc tccactgccc tcagcatttg    360

attgttgttg gctctagcag tggatgcatc cttcaacctc tggcactctg caggggctca    420

gactgttctg ttctgtttgt tacctgtgga gtgcctgcca gaccctgctc tagctgcttt    480

aggtccattt accctcatag acccccagtc ttgttattca tatttcatat ttgggaaatg    540

gaaacttaga aacttgccaa gtccacagca tgagatcctg cctccggtgt ctgctggatt    600

ccagaaagtg ccaggggcca acttagatga caccatgttc tctgcacaat cttaggaatg    660

ctcctagtct gatgtcccca ttgcaaaatt tacattatct tttaacaaaa cgtctttcca    720

aggaggggca tttaaaataa ctgaggttct tcttgctaag gacgttcctg acacaagaga    780

taatttagca tttccttttc attaaaaagt ttgaaatcct gtaatttgtg ataatgtgga    840

tgaacctaga ggatgttaag tgaaataagc cacacacaga tagacaaata ccacgtgatc    900

tcactcttat gtggaatttt tttttaaata agttgcttag ccgggcatga tggcacacac    960

ctgtaatcct agctactcag gaggctgagg tgggaggatg gcttgaactc agaaggtgga   1020

ggtagcagtg agctgagact gtgccagtgc actccggtct gggtgacaga atgaaaccca   1080
```

-continued atttaaaaaa aaaaaaaaag ttgctatctt agaaaaagac agtagagcag tggttaccag 1140
agactgggga ggaaagagag gaggtgagaa tgggcagcag ttgatcaacg ggtacaaagt 1200
taccatgaga taggagaaac aagtgctggt gctctgctcc aagtagggtg acggtagtta 1260
ataatgaatt ctgtatatat aaatagctag aagagagggt tttcaatatc attattattt 1320
caaaagaaat gataaatgtt tcagaggatg gatatgtaat taccctgatt tgatcattgc 1380
acaatgtata catgtagcaa aacatcacat tgtgtcccat aaatatatac aattattatg 1440
tgaattaaat aaaaaaaaat tttaaagtct tatctaaatg aaatttctaa ccagattctg 1500
aatccatgat accactgaaa ccagcacaca tgatcgcagt aaaacctcat tatacttcct 1560
ccactatcac caataccctt tattctctgg aacatgaaac attctgttgt gctcatatca 1620
tgcaaattat cactagtagg agagcagaga gtggaaatgt tccaggtata aagacccaca 1680
agataaagaa gctcagagtc gttagaaaca ggagcagatg tacagggttt gcctgactca 1740
cactcaaggt tgcataagca agatttcaaa attaatccta ttctggagac ctcaacccaa 1800
tgtacaatgt tcctgactgg aaaagaagaa ctatattttt ctgatttttt ttttcaaatc 1860
tttaccatta gttgccctgt atctccgcct tcactttctg caggaaactt tatttcctac 1920
ttctgcatgc caagtttcta cctctagatc tgtttggttc agttgctgag aagcctgaca 1980
taccaggact gcctgagaca agccacaagc tggtgagttg taggcatttt ttccattact 2040
ttctgattca taggctcaac gcacctcaaa gctggaaatg cc 2082

<210> SEQ ID NO 9
<211> LENGTH: 5444
<212> TYPE: DNA
<213> ORGANISM: Homo sapiens

<400> SEQUENCE: 9
ctacctccaa ccatgggcct tttgggaata ctttgttttt taatcttcct ggggaaaacc 60
tggggacagg agcaaacata tgtcatttca gcaccaaaaa tattccgtgt tggagcatct 120
gaaaatattg tgattcaagt ttatggatac actgaagcat ttgatgcaac aatctctatt 180
aaaagttatc ctgataaaaa atttagttac tcctcaggcc atgttcattt atcctcagag 240
aataaattcc aaaactctgc aatcttaaca atacaaccaa aacaattgcc tggaggacaa 300
aacccagttt cttatgtgta tttggaagtt gtatcaaagc atttttcaaa atcaaaaaga 360
atgccaataa cctatgacaa tggatttctc ttcattcata cagacaaacc tgtttatact 420
ccagaccagt cagtaaaagt tagagtttat tcgttgaatg acgacttgaa gccagccaaa 480
agagaaactg tcttaacctt catagatcct gaaggatcag aagttgacat ggtagaagaa 540
attgatcata ttggaattat ctcttttcct gacttcaaga ttccgtctaa tcctagatat 600
ggtatgtgga cgatcaaggc taaatataaa gaggactttt caacaactgg aaccgcatat 660
tttgaagtta aagaatatgt cttgccacat ttttctgtct caatcgagcc agaatataat 720
ttcattggtt acaagaactt taagaatttt gaaattacta taaaagcaag atatttttat 780
aataaagtag tcactgaggc tgacgtttat atcacatttg gaataagaga agacttaaaa 840
gatgatcaaa aagaaatgat gcaaacagca atgcaaaaca caatgttgat aaatggaatt 900
gctcaagtca catttgattc tgaaacagca gtcaaagaac tgtcatacta cagtttagaa 960
gatttaaaca acaagtacct ttatattgct gtaacagtca tagagtctac aggtggattt 1020
tctgaagagg cagaaatacc tggcatcaaa tatgtcctct ctccctacaa actgaatttg 1080
gttgctactc ctcttttcct gaagcctggg attccatatc ccatcaaggt gcaggttaaa 1140

-continued

```
gattcgcttg accagttggt aggaggagtc ccagtaatac tgaatgcaca aacaattgat   1200
gtaaaccaag agacatctga cttggatcca agcaaaagtg taacacgtgt tgatgatgga   1260
gtagcttcct ttgtgcttaa tctcccatct ggagtgacgg tgctggagtt taatgtcaaa   1320
actgatgctc cagatcttcc agaagaaaat caggccaggg aaggttaccg agcaatagca   1380
tactcatctc tcagccaaag ttacctttat attgattgga ctgataacca taaggctttg   1440
ctagtgggag aacatctgaa tattattgtt acccccaaaa gcccatatat tgacaaaata   1500
actcactata attacttgat tttatccaag ggcaaaatta tccattttgg cacgagggag   1560
aaattttcag atgcatctta tcaaagtata aacattccag taacacagaa catggttcct   1620
tcatcccgac ttctggtcta ttatatcgtc acaggagaac agacagcaga attagtgtct   1680
gattcagtct ggttaaatat tgaagaaaaa tgtggcaacc agctccaggt tcatctgtct   1740
cctgatgcag atgcatattc tccaggccaa actgtgtctc ttaatatggc aactggaatg   1800
gattcctggg tggcattagc agcagtggac agtgctgtgt atggagtcca aagaggagcc   1860
aaaaagccct tggaaagagt atttcaattc ttagagaaga gtgatctggg ctgtggggca   1920
ggtggtggcc tcaacaatgc caatgtgttc cacctagctg gacttacctt cctcactaat   1980
gcaaatgcag atgactccca agaaaatgat gaaccttgta aagaaattct caggccaaga   2040
agaacgctgc aaaagaagat agaagaaata gctgctaaat ataaacattc agtagtgaag   2100
aaatgttgtt acgatggagc ctgcgttaat aatgatgaaa cctgtgagca gcgagctgca   2160
cggattagtt tagggccaag atgcatcaaa gctttcactg aatgttgtgt cgtcgcaagc   2220
cagctccgtg ctaatatctc tcataaagac atgcaattgg gaaggctaca catgaagacc   2280
ctgttaccag taagcaagcc agaaattcgg agttattttc cagaaagctg gttgtgggaa   2340
gttcatcttg ttcccagaag aaaacagttg cagtttgccc tacctgattc tctaaccacc   2400
tgggaaattc aaggcattgg catttcaaac actggtatat gtgttgctga tactgtcaag   2460
gcaaaggtgt tcaaagatgt cttcctggaa atgaatatac catattctgt tgtacgagga   2520
gaacagatcc aattgaaagg aactgtttac aactatagga cttctgggat gcagttctgt   2580
gttaaaatgt ctgctgtgga gggaatctgc acttcggaaa gcccagtcat tgatcatcag   2640
ggcacaaagt cctccaaatg tgtgcgccag aaagtagagg gctcctccag tcacttggtg   2700
acattcactg tgcttcctct ggaaattggc cttcacaaca tcaatttttc actggagact   2760
tggtttggaa aagaaatctt agtaaaaaca ttacgagtgg tgccagaagg tgtcaaaagg   2820
gaaagctatt ctggtgttac tttggatcct aggggtattt atggtaccat tagcagacga   2880
aaggagttcc catacaggat acccttagat ttggtcccca aaacagaaat caaaaggatt   2940
ttgagtgtaa aaggactgct tgtaggtgag atcttgtctg cagttctaag tcaggaaggc   3000
atcaatatcc taacccacct ccccaaaggg agtgcagagg cggagctgat gagcgttgtc   3060
ccagtattct atgtttttca ctacctggaa acaggaaatc attggaacat ttttcattct   3120
gacccattaa ttgaaaagca gaaactgaag aaaaaattaa aagaagggat gttgagcatt   3180
atgtcctaca gaaatgctga ctactcttac agtgtgtgga agggtggaag tgctagcact   3240
tggttaacag cttttgcttt aagagtactt ggacaagtaa ataaatacgt agagcagaac   3300
caaaattcaa tttgtaattc tttattgtgg ctagttgaga attatcaatt agataatgga   3360
tctttcaagg aaaattcaca gtatcaacca ataaaattac agggtacctt gcctgttgaa   3420
gcccgagaga acagcttata tcttacagcc tttactgtga ttggaattag aaaggctttc   3480
gatatatgcc ccctggtgaa aatcgacaca gctctaatta aagctgacaa ctttctgctt   3540
```

-continued gaaaatacac tgccagccca gagcaccttt acattggcca tttctgcgta tgctctttcc 3600
ctgggagata aaactcaccc acagtttcgt tcaattgttt cagctttgaa gagagaagct 3660
ttggttaaag gtaatccacc catttatcgt ttttggaaag acaatcttca gcataaagac 3720
agctctgtac ctaacactgg tacggcacgt atggtagaaa caactgccta tgctttactc 3780
accagtctga acttgaaaga tataaattat gttaacccag tcatcaaatg gctatcagaa 3840
gagcagaggt atggaggtgg cttttattca acccaggaca ccatcaatgc cattgagggc 3900
ctgacggaat attcactcct ggttaaacaa ctccgcttga gtatggacat cgatgtttct 3960
tacaagcata aaggtgcctt acataattat aaaatgacag acaagaattt ccttgggagg 4020
ccagtagagg tgcttctcaa tgatgacctc attgtcagta caggatttgg cagtggcttg 4080
gctacagtac atgtaacaac tgtagttcac aaaaccagta cctctgagga agtttgcagc 4140
ttttatttga aaatcgatac tcaggatatt gaagcatccc actacagagg ctacggaaac 4200
tctgattaca aacgcatagt agcatgtgcc agctacaagc ccagcaggga agaatcatca 4260
tctggatcct ctcatgcggt gatggacatc tccttgccta ctggaatcag tgcaaatgaa 4320
gaagacttaa aagcccttgt ggaaggggtg gatcaactat tcactgatta ccaaatcaaa 4380
gatggacatg ttattctgca actgaattcg attccctcca gtgatttcct ttgtgtacga 4440
ttccggatat ttgaactctt tgaagttggg tttctcagtc ctgccacttt cacagtttac 4500
gaataccaca gaccagataa acagtgtacc atgttttata gcacttccaa tatcaaaatt 4560
cagaaagtct gtgaaggagc cgcgtgcaag tgtgtagaag ctgattgtgg gcaaatgcag 4620
gaagaattgg atctgacaat ctctgcagag acaagaaaac aaacagcatg taaaccagag 4680
attgcatatg cttataaagt tagcatcaca tccatcactg tagaaaatgt tttttgtcaag 4740 tacaaggcaa cccttctgga tatctacaaa actggggaag ctgttgctga gaaagactct 4800
gagattacct tcattaaaaa ggtaacctgt actaacgctg agctggtaaa aggaagacag 4860
tacttaatta tgggtaaaga agccctccag ataaaataca atttcagttt caggtacatc 4920
taccctttag attccttgac ctggattgaa tactggccta gagacacaac atgttcatcg 4980
tgtcaagcat tttagctaa tttagatgaa tttgccgaag atatcttttt aaatggatgc 5040
taaaattcct gaagttcagc tgcatacagt ttgcacttat ggactcctgt tgttgaagtt 5100 cgttttttg ttttcttctt tttttaaaca ttcatagctg gtcttatttg taaagctcac 5160
tttacttaga attagtggca cttgctttta ttagagaatg atttcaaatg ctgtaacttt 5220
ctgaaataac atggccttgg agggcatgaa gacagatact cctccaaggt tattggacac 5280
cggaaacaat aaattggaac acctcctcaa acctaccact caggaatgtt tgctggggcc 5340
gaaagaacag tccattgaaa gggagtatta caaaaacatg gcctttgctt gaaagaaaat 5400
accaaggaac aggaaactga tcattaaagc ctgagtttgc tttc 5444

<210> SEQ ID NO 10
<211> LENGTH: 222
<212> TYPE: DNA
<213> ORGANISM: Homo sapiens

<400> SEQUENCE: 10
ctacctccaa ccatgggcct tttgggaata ctttgttttt taatcttcct ggggaaaacc 60
tggggacagg agcaaacata tgtcatttca gcaccaaaaa tattccgtgt tggagcatct 120
gaaaatattg tgattcaagt ttatggatac actgaagcat ttgatgcaac aatctctatt 180
aaaagttatc ctgataaaaa atttagttac tcctcaggcc at 222